(12) United States Patent
Pyle et al.

(10) Patent No.: US 11,649,457 B2
(45) Date of Patent: May 16, 2023

(54) METHODS FOR TREATING SARS-COV-2 INFECTION

(71) Applicant: YALE UNIVERSITY, New Haven, CT (US)

(72) Inventors: Anna Marie Pyle, Guilford, CT (US);
Akiko Iwasaki, Guilford, CT (US);
Tianyang Mao, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 17/709,282

(22) Filed: Mar. 30, 2022

(65) Prior Publication Data

US 2022/0340902 A1    Oct. 27, 2022

Related U.S. Application Data

(63) Continuation-in-part of application No. PCT/US2021/062632, filed on Dec. 9, 2021, which is a continuation-in-part of application No. 17/115,968, filed on Dec. 9, 2020.

(60) Provisional application No. 63/158,726, filed on Mar. 9, 2021, provisional application No. 63/210,869, filed on Jun. 15, 2021.

(51) Int. Cl.
*C12N 15/113* (2010.01)
*A61P 31/14* (2006.01)

(52) U.S. Cl.
CPC .......... *C12N 15/113* (2013.01); *A61P 31/14* (2018.01); *C12N 2310/14* (2013.01); *C12N 2310/531* (2013.01); *C12N 2320/30* (2013.01)

(58) Field of Classification Search
CPC .............. C12N 15/113; C12N 2310/14; C12N 2310/531; C12N 2320/30
USPC .................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 2007/0224186 A1 | 9/2007 | Kulaksiz et al. |
| 2007/0269448 A1 | 11/2007 | Schramm et al. |
| 2007/0270360 A1 | 11/2007 | McSwiggen et al. |
| 2008/0293053 A1 | 11/2008 | Keller et al. |
| 2009/0123501 A1 | 5/2009 | Levitt et al. |
| 2009/0247613 A1 | 10/2009 | McSwiggen et al. |
| 2011/0097390 A1 | 4/2011 | Ambati |
| 2011/0123520 A1 | 5/2011 | Manoharan et al. |
| 2011/0165123 A1 | 7/2011 | Hartmann et al. |
| 2011/0251258 A1 | 10/2011 | Samarsky et al. |
| 2012/0088815 A1 | 4/2012 | Liang |
| 2012/0329857 A1 | 12/2012 | Ge et al. |
| 2014/0024819 A1 | 1/2014 | Ludwig et al. |
| 2016/0040161 A1 | 2/2016 | Packard et al. |
| 2016/0046943 A1 | 2/2016 | Pyle et al. |
| 2019/0184006 A1* | 6/2019 | Chan .................... A61K 39/145 |

OTHER PUBLICATIONS

WHO (Tracking SARS-CoV-2 Variants (Jan. 2021)) (Year: 2021).*
Jiang et al (J. Expt'l Med., vol. 216, No. 12, pp. 2854-2868 (2019)) (Year: 2019).*
5'ppp-dsRNA, Technical Data Sheet, Invivogen (http://www.invivogen.com/PDF/5pppRNA TDS.pdf), accessed Jan. 2013.
Abdullah, et al., "RIG-I detects infection with live Listeria by sensing secreted bacterial nucleic acids", EMBO J. 31(21), Nov. 2012, 4153-4164.
Ablasser, et al., "RIG-I-dependent sensing of poly(dA:dT) through the induction of an RNA polymerase III-transcribed RNA intermediate", Nat Immunol. 10(10), Oct. 2009, 1065-1072.
Bamming, et al., "Regulation of signal transduction by enzymatically inactive antiviral RNA helicase proteins MDA5, Rig-I, and LGP2", J Biol Chem. 284(15), Apr. 2009, 9700-9712.
Beckham, et al., "Conformational rearrangements of RIG-I receptor on formation of a multiprotein:dsRNA assembly", Nucleic Acids Res. 41(5), Mar. 2013, 3436-3445.
Berke, et al., "MDA5 assembles into a polar helical filament on dsRNA", Proc Natl Acad Sci U S A 109(45), Nov. 2012, 18437-18441.
Berke, et al., "MDA5 cooperatively forms dimers and ATP-sensitive filaments upon binding double-stranded RNA", EMBO J. 31(7), Apr. 2012, 1714-1726.
Binder, et al., "Molecular mechanism of signal perception and integration by the innate immune sensor retinoic acid-inducible gene-I (RIG-I)", J Biol Chem. 286(31), Aug. 2011, 27278-27287.
Chiu, et al., "RNA polymerase III detects cytosolic DNA and induces type 1 interferons through the RIG-I pathway", Cell 138(3), Aug. 2009, 576-591.
Civril, et al., "The RIG-I ATPase domain structure reveals insights into ATP-dependent antiviral signalling", EMBO Rep. 12(11), Oct. 2011, 1127-1134.
Deguzman, et al., "Sequence-dependent gating of an ion channel by DNA hairpin molecules", Nucleic Acids Res. 34(22), 2006, 6425-6437.

(Continued)

*Primary Examiner* — Jane J Zara
(74) *Attorney, Agent, or Firm* — Saul Ewing LLP

(57) ABSTRACT

The present disclosure provides small hairpin nucleic acid molecules capable of stimulating interferon production. The nucleic acid molecules of the present disclosure has a double-stranded section of less than 19 base pairs and at least one blunt end. In certain embodiments, the molecule comprises at least one 5'-triphosphate and/or at least one 5'-diphosphate. In certain embodiments, compounds and/or compositions of the disclosure are useful for treating, ameliorating, and/or preventing SARS-CoV-2 viral infection, and/or ameliorating, minimizing, reversing, and/or preventing persistent SARS-CoV-2 viral infection, and/or minimizing or preventing SARS-CoV-2 viral infection-derived mortality and/or lethality, in a subject. In certain embodiments, compounds and/or compositions of the disclosure are useful for treating, ameliorating, and/or preventing SARS-CoV-2 viral infection in a tumor-bearing subject. In certain embodiments, compounds and/or compositions of the disclosure are useful for treating, ameliorating, and/or preventing SARS-CoV-2 viral infection in an immune-compromised and/or immunodeficient subject.

15 Claims, 64 Drawing Sheets

Specification includes a Sequence Listing.

(56) References Cited

OTHER PUBLICATIONS

Feng, et al., "Structural and biochemical studies of RIG-I antiviral signaling", Protein Cell 4(2), Feb. 2013, 142-154.
Gack, et al., "TRIM25 RING-finger E3 ubiquitin ligase is essential for RIG-I-mediated antiviral activity", Nature 446(7138), Apr. 2007, 916-920.
Ge, et al., "Effects of chemical modification on the potency, serum stability, and immunostimulatory properties of short shRNAs", RNA 16(1), Jan. 2010, 118-130.
Ge, et al., "Minimal-length short hairpin RNAs: the relationship of structure and RNAi activity", RNA 16(1), Jan. 2010, 106-117.
Guo, et al., "Transfection reagent Lipofectamine triggers type I interferon signaling activation in macrophages", Immunol Cell Biol. 97(1), Jan. 2019, 92-96.
Hwang, et al., "5'-Triphosphate-RNA-independent activation of RIG-I via RNA aptamer with enhanced antiviral activity", Nucleic Acids Res. 40(6), Mar. 2012, 2724-2733.
Jiang, et al., "Structural basis of RNA recognition and activation by innate immune receptor RIG-I", Nature 479(7373), Sep. 2011, 423-427.
Jiang, et al., "Ubiquitin-induced oligomerization of the RNA sensors RIG-I and MDA5 activates antiviral innate immune response", Immunity 36(6), Jun. 2012, 959-973.
Kageyama, et al., "55 Amino acid linker between helicase and carboxyl terminal domains of RIG-I functions as a critical repression domain and determines inter-domain conformation", Biochem Biophys Res Commun. 415(1), Nov. 2011, 75-81.
Kato, et al., "Length-dependent recognition of double-stranded ribonucleic acids by retinoic acid-inducible gene-I and melanoma differentiation-associated gene 5", J Exp Med. 205(7), Jul. 2008, 1601-1610.
Kato, et al., "RIG-I-like receptors: cytoplasmic sensors for non-self RNA", Immunol Rev. 243(1), Sep. 2011, 91-98.
Kohlway, et al., "Defining the functional determinants for RNA surveillance by Rig-I", EMBO Rep. 14(9), Sep. 2013, 772-779.
Kolakofsky, et al., "A structure-based model of RIG-I activation", RNA 18(12), Dec. 2012, 2118-2127.
Kowalinski, et al., "Structural basis for the activation of innate immune pattern-recognition receptor RIG-I by viral RNA", Cell 147(2), Oct. 2011, 423-435.
Li, et al., "Adjuvant effects of plasmid-generated hairpin RNA molecules on DNA vaccination", Vaccine 25(39-40), Sep. 2007, 6992-7000.
Lu, et al., "Crystal structure of RIG-I C-terminal domain bound to blunt-ended double-strand RNA without 5' triphosphate", Nucleic Acids Res. 39(4), Mar. 2011, 1565-1575.
Lu, et al., "The structural basis of 5' triphosphate double-stranded RNA recognition by RIG-I C-terminal domain", Structure 18(8), Aug. 2010, 1032-1043.
Luo, et al., "Duplex RNA activated ATPases (DRAs): platforms for RNA sensing, signaling and processing", RNA Biol. 10(1), Jan. 2013, 111-120.
Luo, et al., "Structural insights into RNA recognition by RIG-I", Cell 147(2), Oct. 2011, 409-422.
Luo, et al., "Visualizing the determinants of viral RNA recognition by innate immune sensor RIG-I", Structure 20(11), Nov. 2012, 1983-1988.
Malathi, et al., "RNase L releases a small RNA from HCV RNA that refolds into a potent PAMP", RNA 16(11), Nov. 2010, 2108-2119.
Malathi, et al., "Small self-RNA generated by RNase L amplifies antiviral innate immunity", Nature 448(7155), Aug. 2007, 816-819.
Martínez-Gil, et al., "A Sendai virus-derived RNA agonist of RIG-I as a virus vaccine adjuvant", J Virol. 87(3), Feb. 2013, 1290-1300.
Peisley, et al., "Cooperative assembly and dynamic disassembly of MDA5 filaments for viral dsRNA recognition", Proc Natl Acad Sci USA. 108(52), Dec. 2011, 21010-21015.
Poeck, et al., "5'-Triphosphate-siRNA: turning gene silencing and Rig-I activation against melanoma", Nat Med. 14(11), Nov. 2008, 1256-1263.
Pyle, "Translocation and unwinding mechanisms of RNA and DNA helicases", Annu Rev Biophys. 37, 2008, 317-336.
Ramos, et al., "RIG-I like receptors and their signaling crosstalk in the regulation of antiviral immunity", Curr Opin Virol. 1(3), Sep. 2011, 167-176.
Saito, et al., "Regulation of innate antiviral defenses through a shared repressor domain in RIG-I and LGP2", Proc Natl Acad Sci USA 104(2), Jan. 2007, 582-587.
Satoh, et al., "LGP2 is a positive regulator of RIG-I- and MDA5-mediated antiviral responses", Proc Natl Acad Sci U S A. 107(4), Jan. 2010, 1512-1517.
Schlee, et al., "Recognition of 5' triphosphate by RIG-I helicase requires short blunt double-stranded RNA as contained in panhandle of negative-strand virus", Immunity 31(1), Jul. 2009, 25-34.
Schlee, et al., "The chase for the RIG-I ligand—recent advances", Mol Ther. 18(7), Jul. 2010, 1254-1262.
Schmidt, et al., "5'-triphosphate RNA requires base-paired structures to activate antiviral signaling via RIG-I", Proc Natl Acad Sci U S A 106(29), Jul. 2009, 12067-12072.
Vela, et al., "The thermodynamic basis for viral RNA detection by the RIG-I innate immune sensor", J Biol Chem. 287(51), Dec. 2012, 42564-42573.
Wang, et al., "Structural and functional insights into 5'-ppp RNA pattern recognition by the innate immune receptor RIG-I", Nat Struct Mol Biol. 17(7), Jul. 2010, 781-787.
Phetsouphanh, et al. "Immunological dysfunction persists for 8 months following initial mild-to-moderate SARS-CoV-2 infection." Nature immunology 23.2 (2022): 210-216.
Park, et al. "Type I and type III interferons-induction, signaling, evasion, and application to combat COVID-19." Cell host & microbe 27.6 (2020): 870-878.
Wang, et al. "Retrospective multicenter cohort study shows early interferon therapy is associated with favorable clinical responses in COVID-19 patients." Cell host & microbe 28.3 (2020): 455-464.
Faria, et al. "Genomics and epidemiology of the P. 1 SARS-CoV-2 lineage in Manaus, Brazil." Science 372.6544 (2021): 815-821.
Jiang, et al. "Intratumoral delivery of RIG-I agonist SLR14 induces robust antitumor responses." Journal of Experimental Medicine 216.12 (2019): 2854-2868.

\* cited by examiner

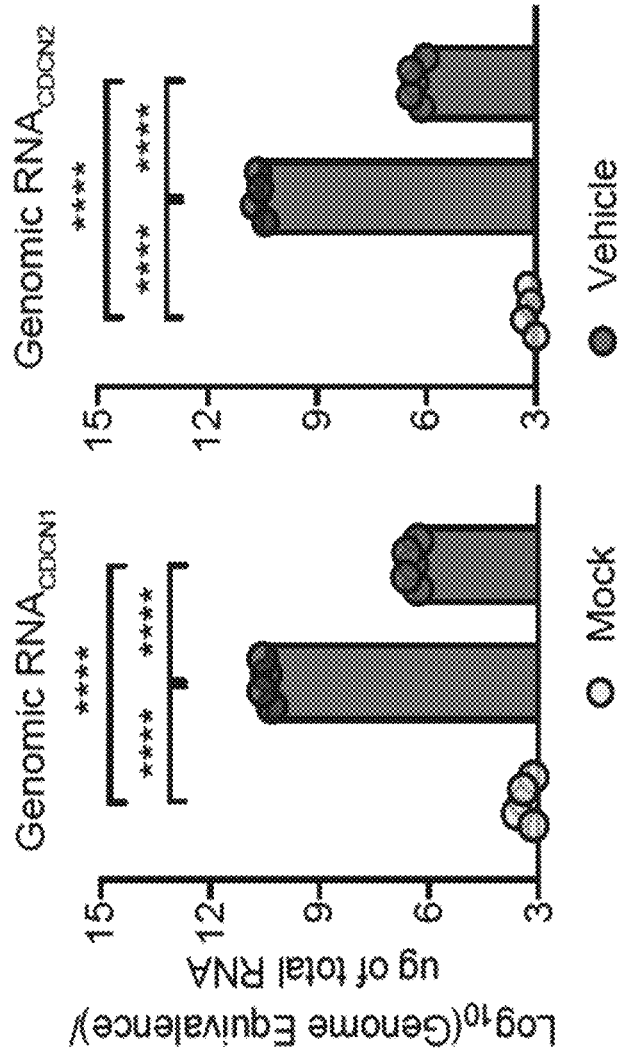

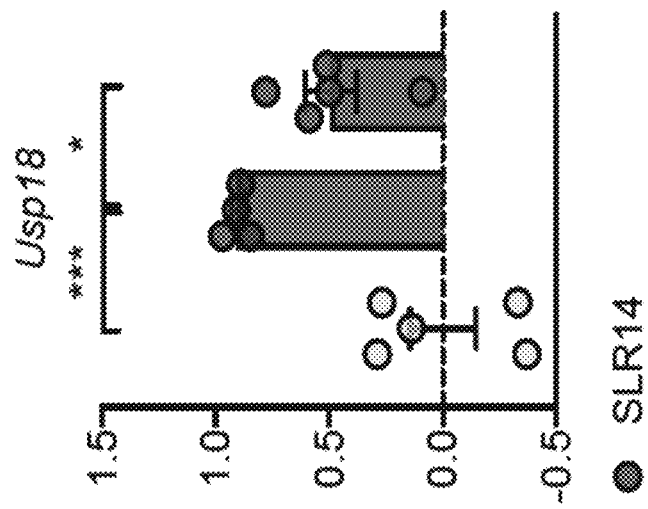
FIG. 5G  FIG. 5H  FIG. 5I
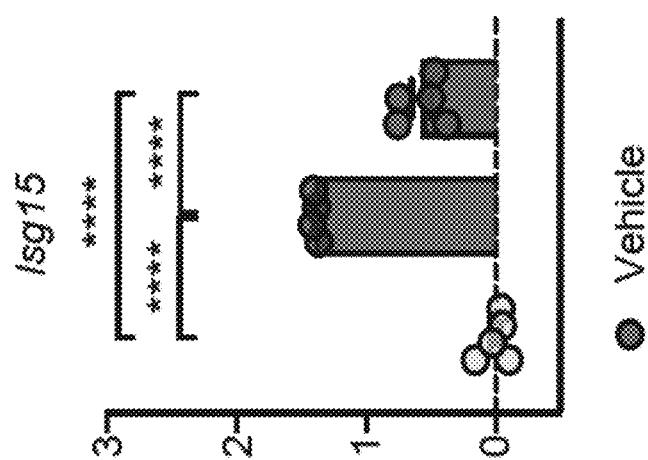
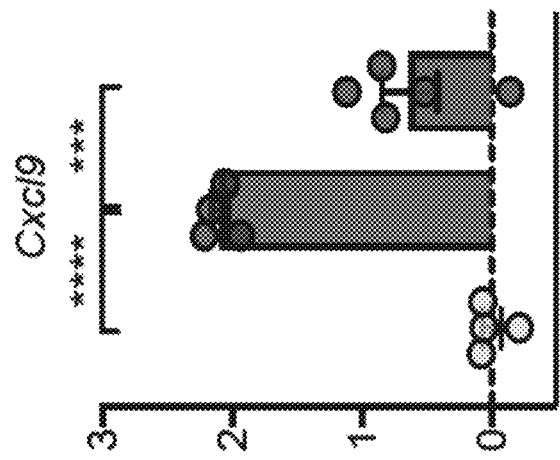

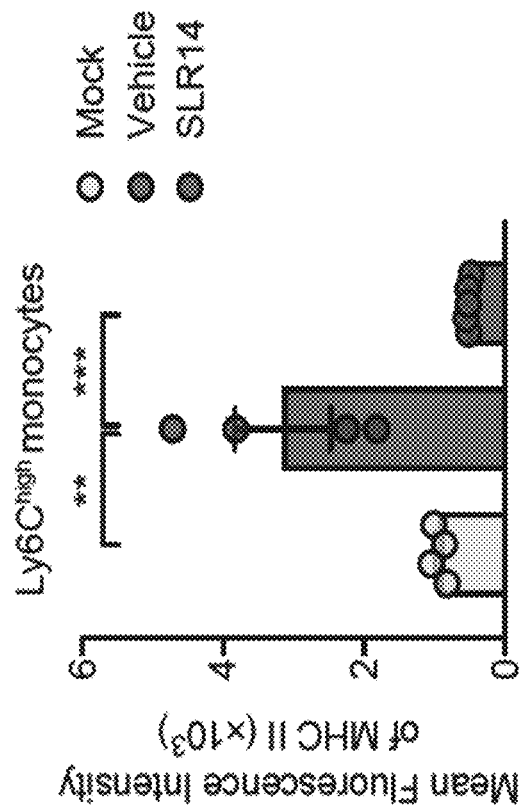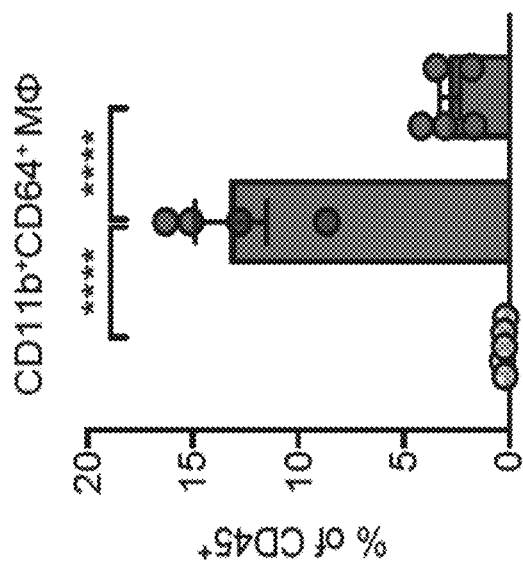
FIG. 5K
FIG. 5J

Intranasal infection of $10^3$ PFU SARS-CoV-2 in K18hACE2 mice

Intranasal infection of $10^3$ PFU SARS-CoV-2 in K18hACE2 mice

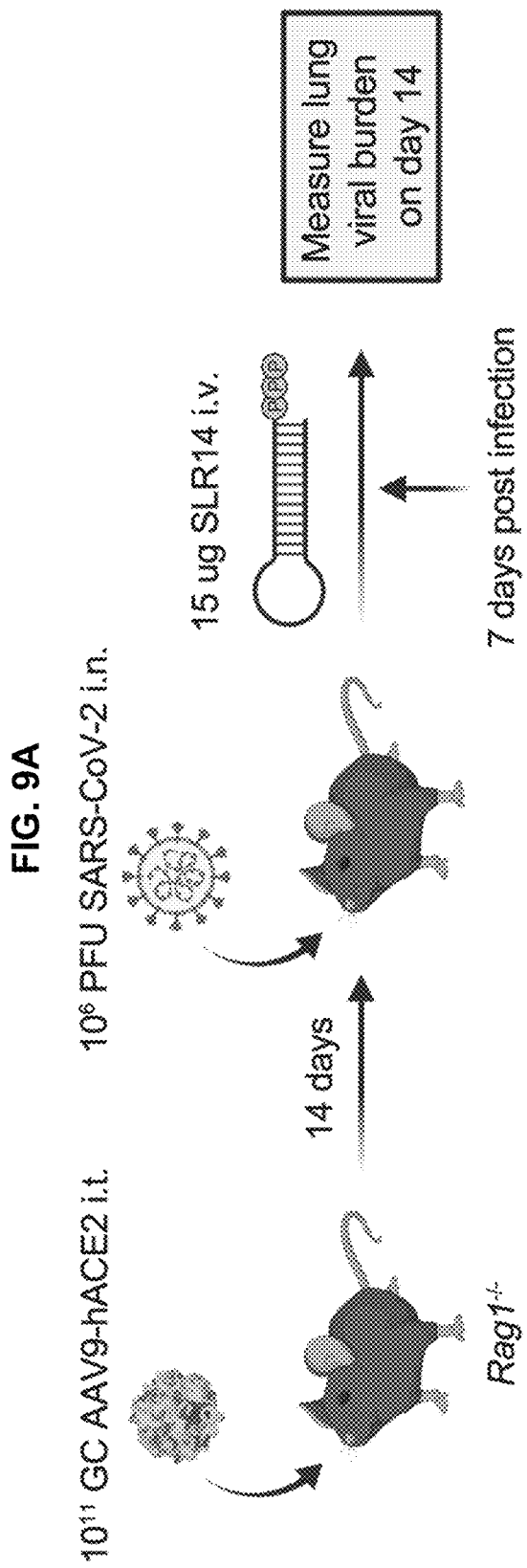

Intranasal infection of $10^6$ PFU SARS-CoV-2 in AAV-hACE2 transduced C57BL/6J and $Rag1^{-/-}$ mice

CDC N1

○ *Rag1*[-/-]+Vehicle

Infectious viruses

● *Rag1*[-/-]+SLR14

Intranasal infection of $10^6$ PFU SARS-CoV-2 in AAV-hACE2 transduced *Rag1*[-/-] mice

FIG. 12F
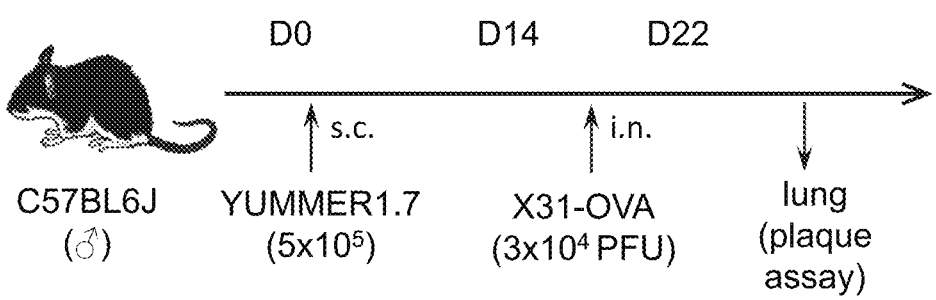
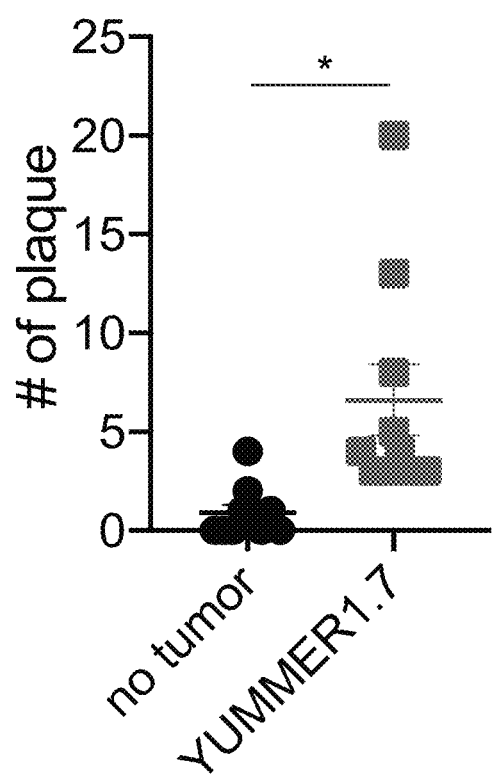

1. pre-treated: 25 ug SLR14 5 hours before PR8 challenge
2. post-treated: 25 ug SLR14 5 hours after PR8 challenge
3. vehicle: vehicle 5 hours before PR8 challenge

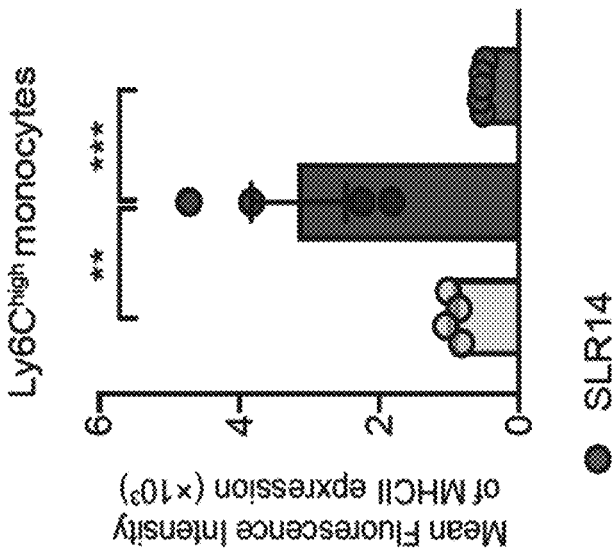
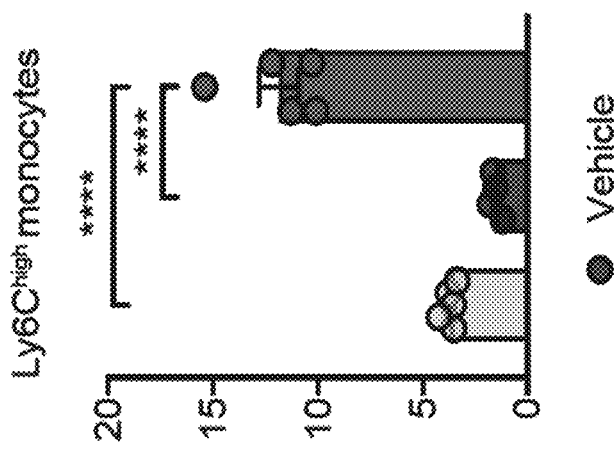
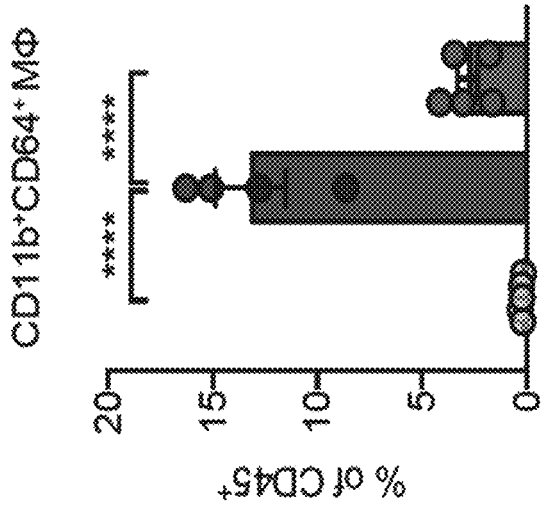

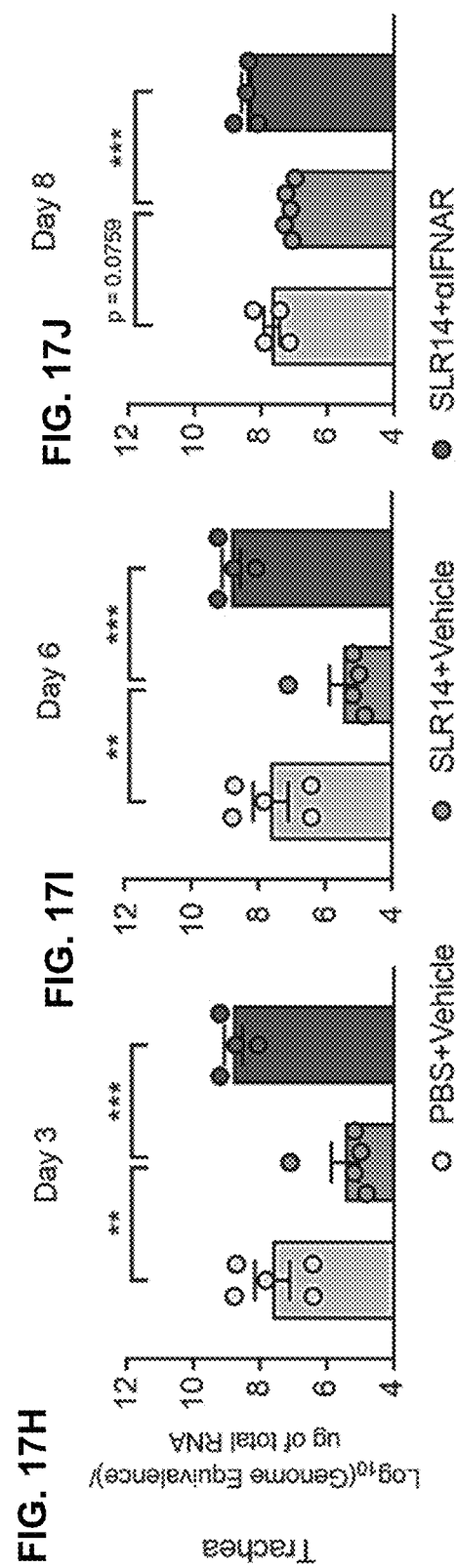

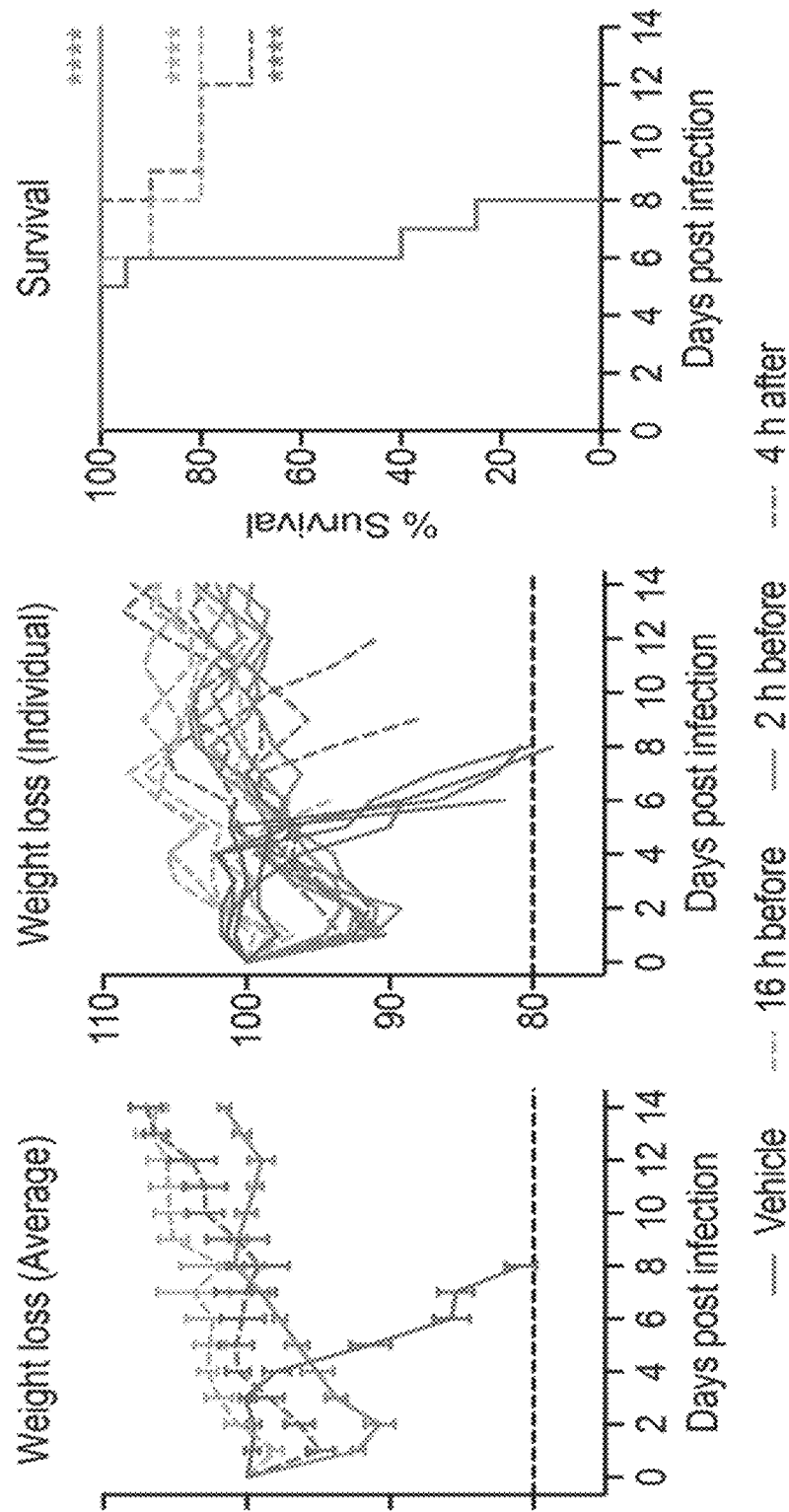

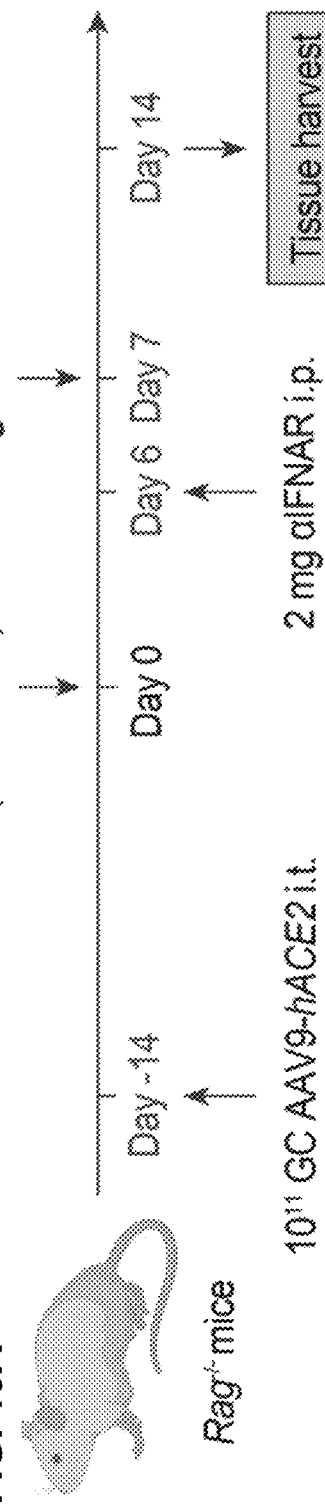
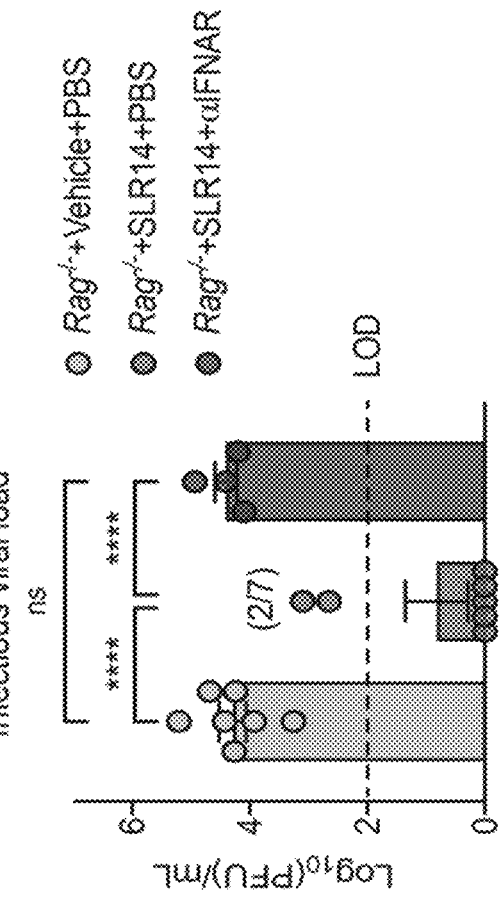
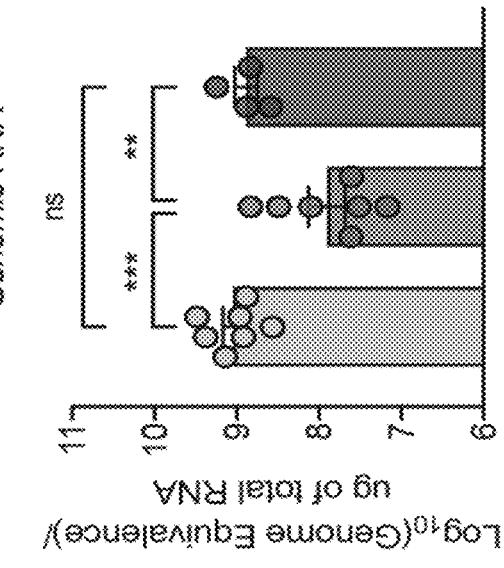
FIG. 19A
FIG. 19B
FIG. 19C

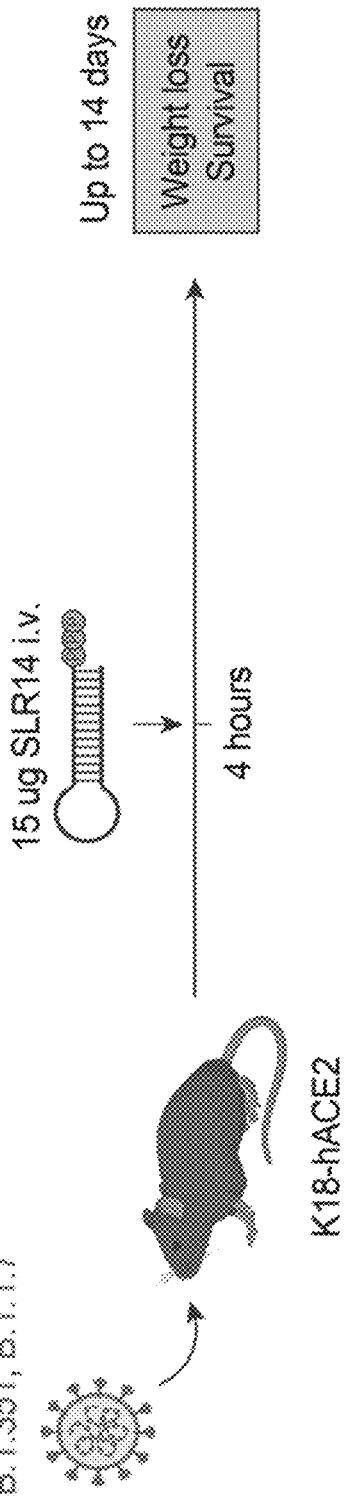
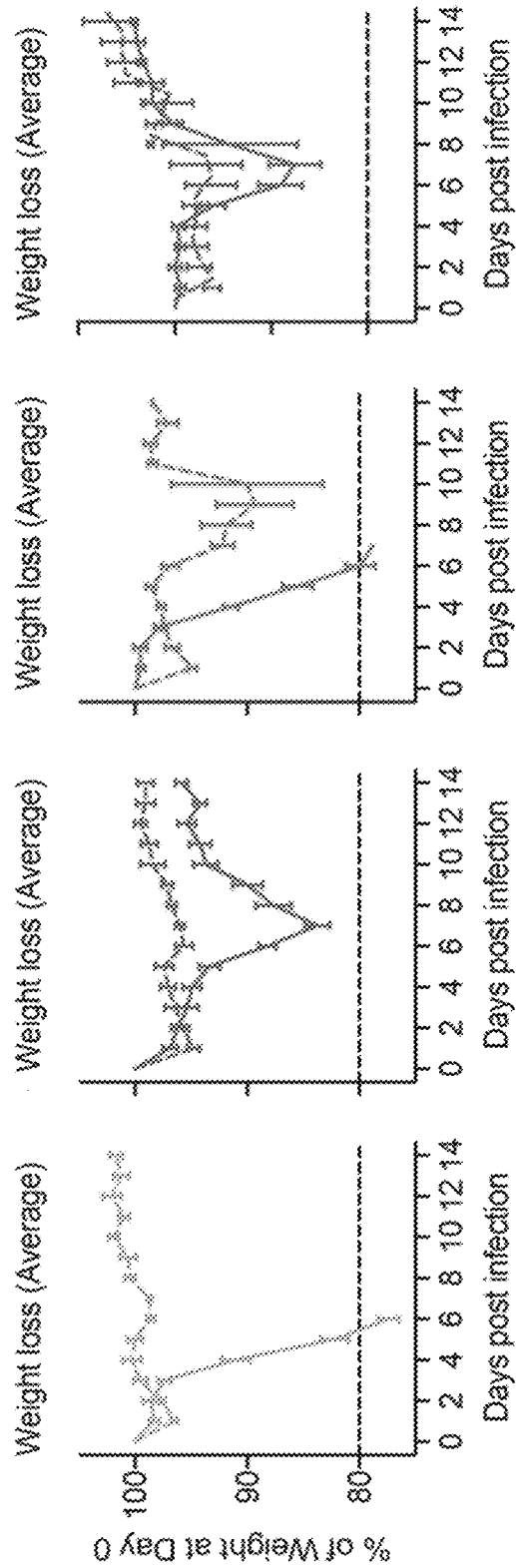

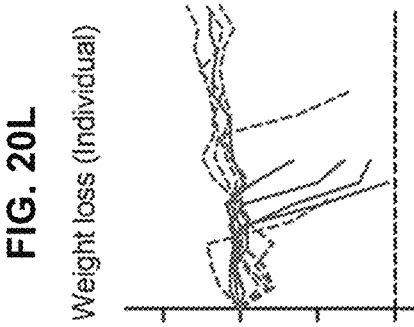
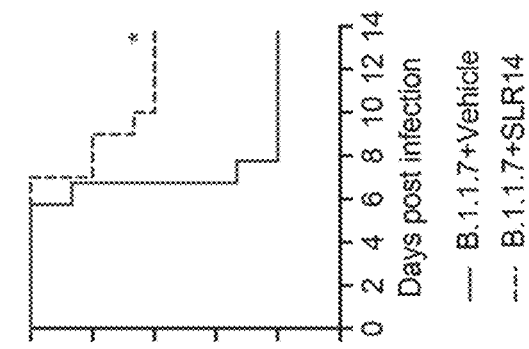
FIG. 20C  FIG. 20F  FIG. 20I  FIG. 20L
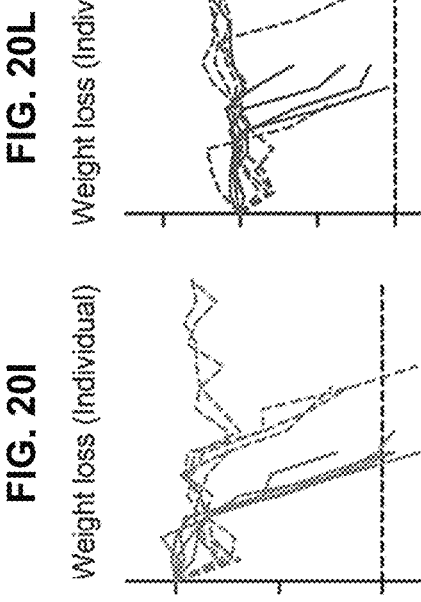
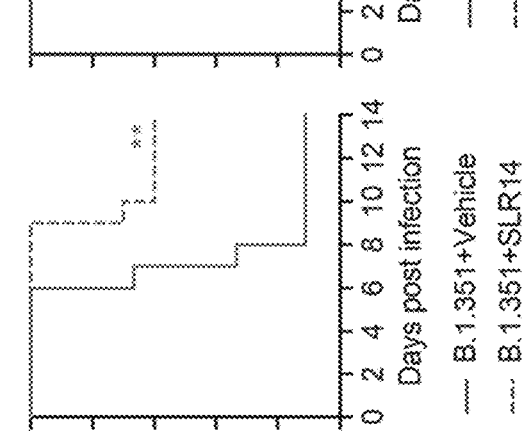
FIG. 20D  FIG. 20G  FIG. 20J  FIG. 20M
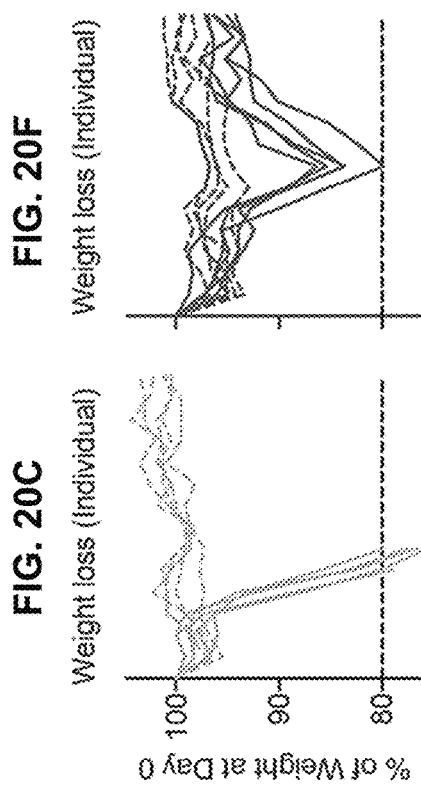
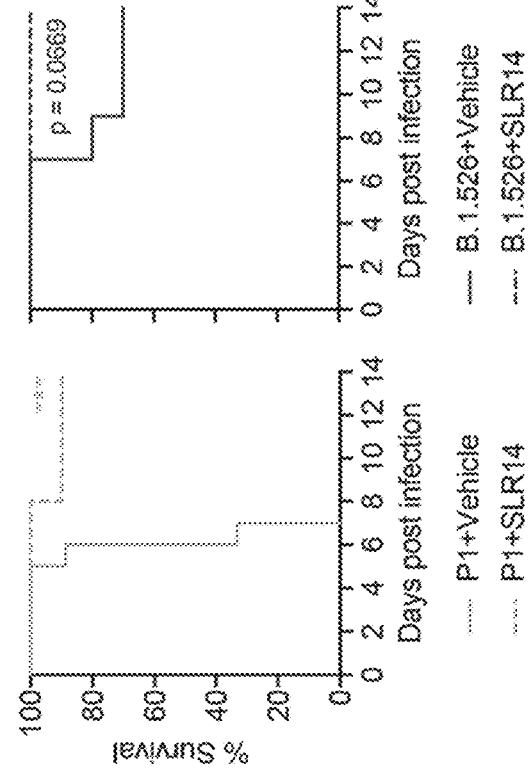

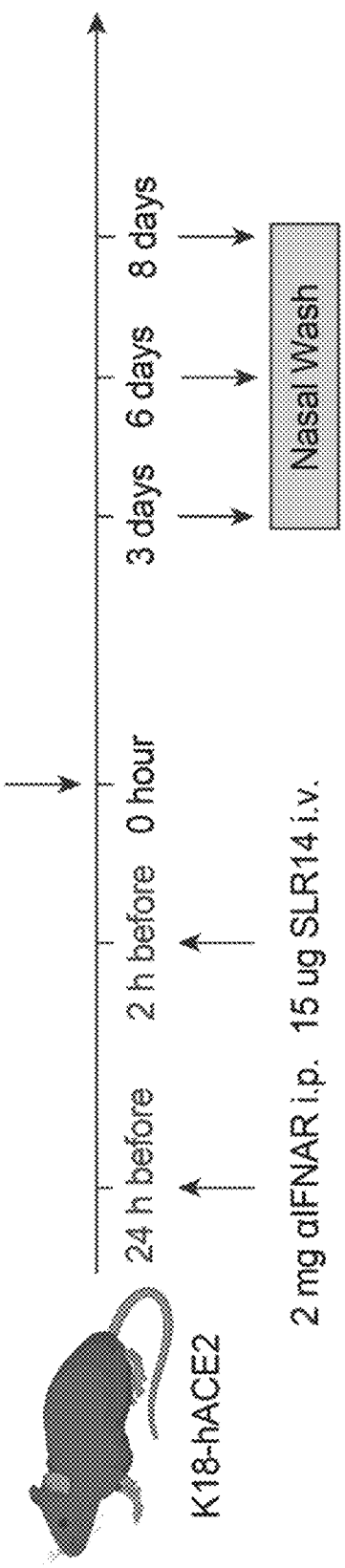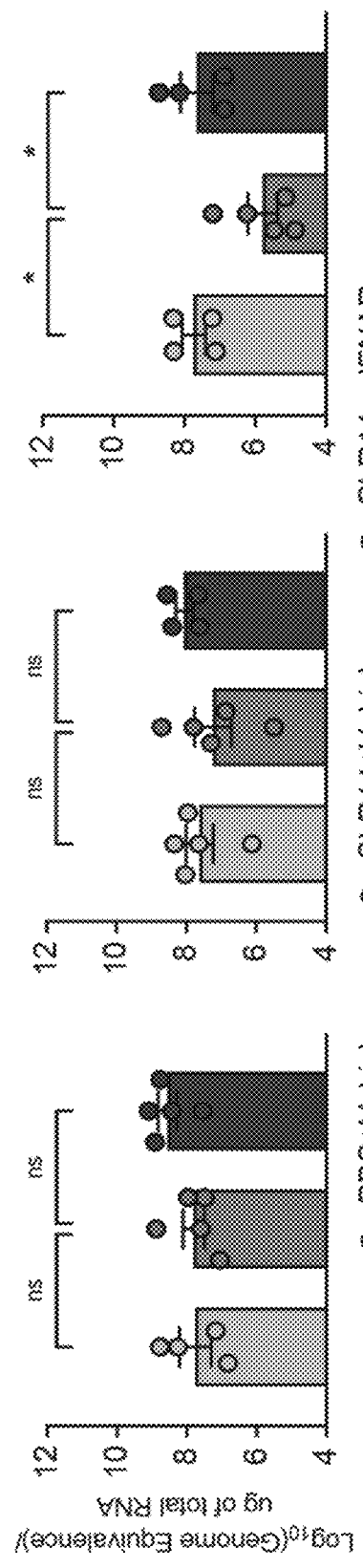
FIG. 21A
FIG. 21B
FIG. 21C
FIG. 21D

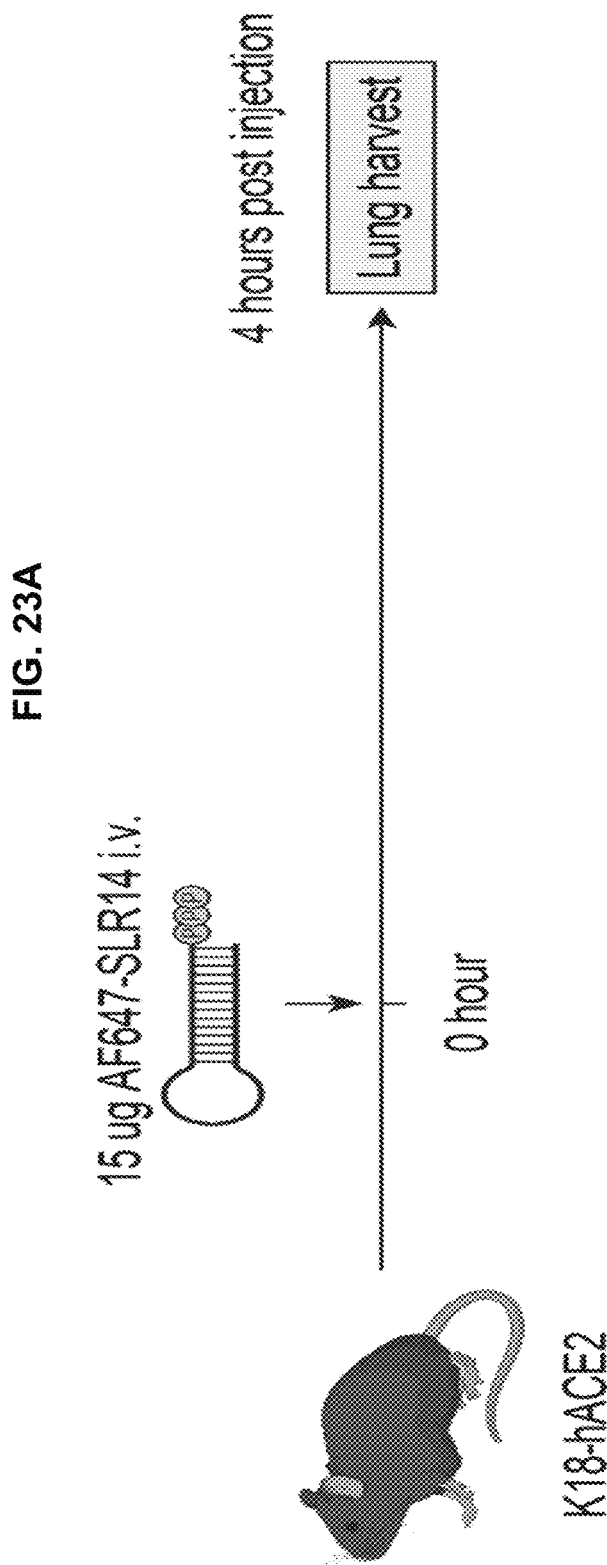

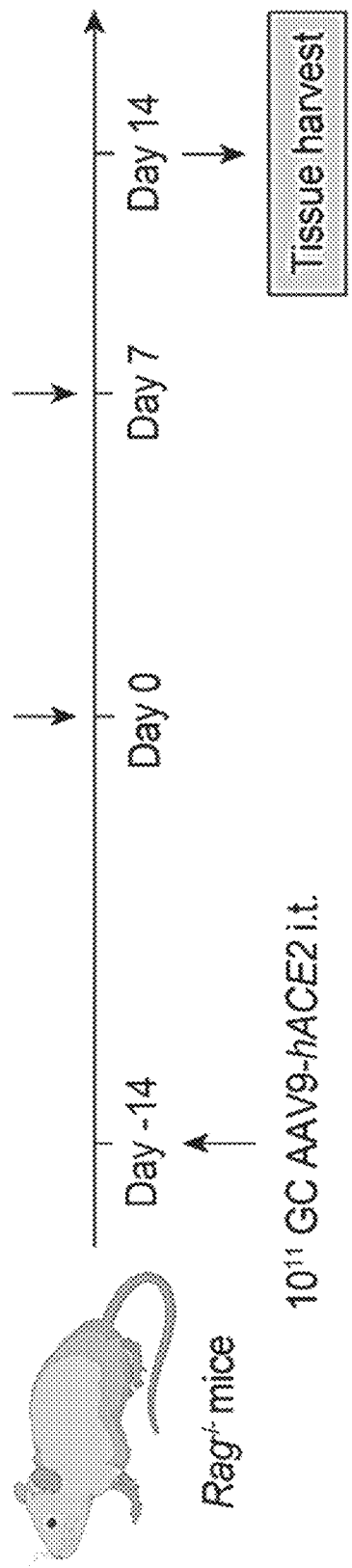
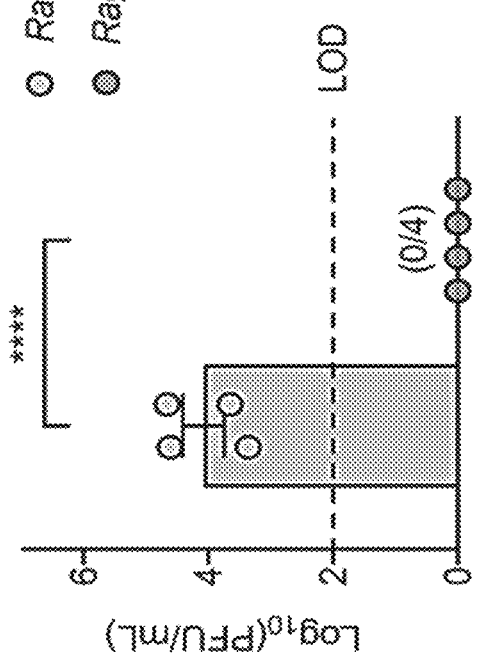
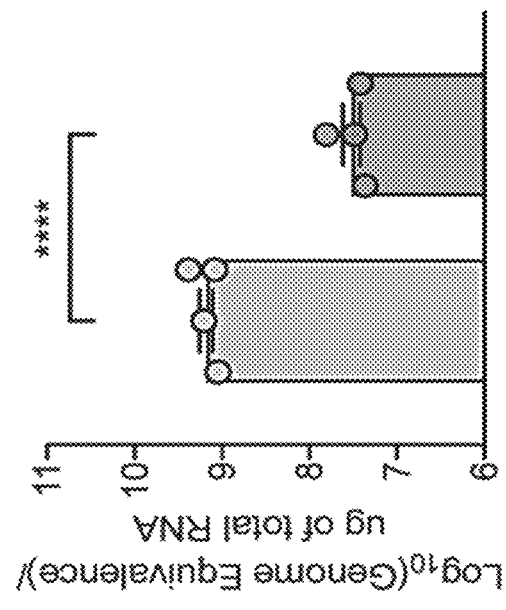

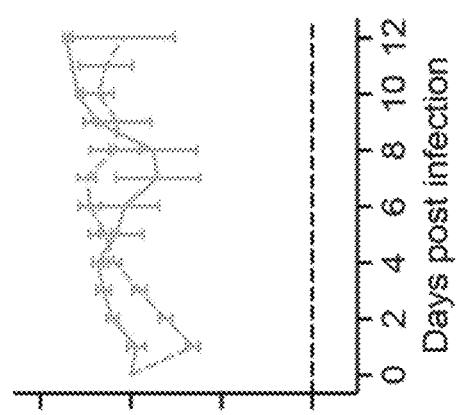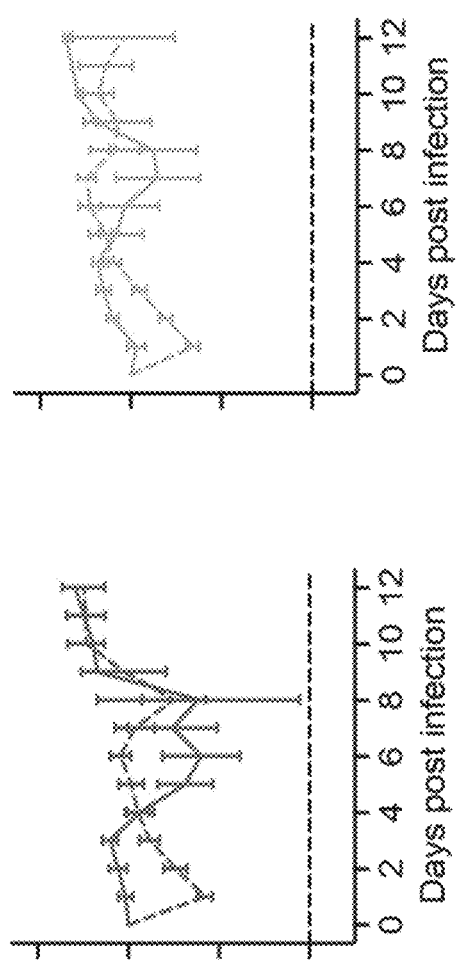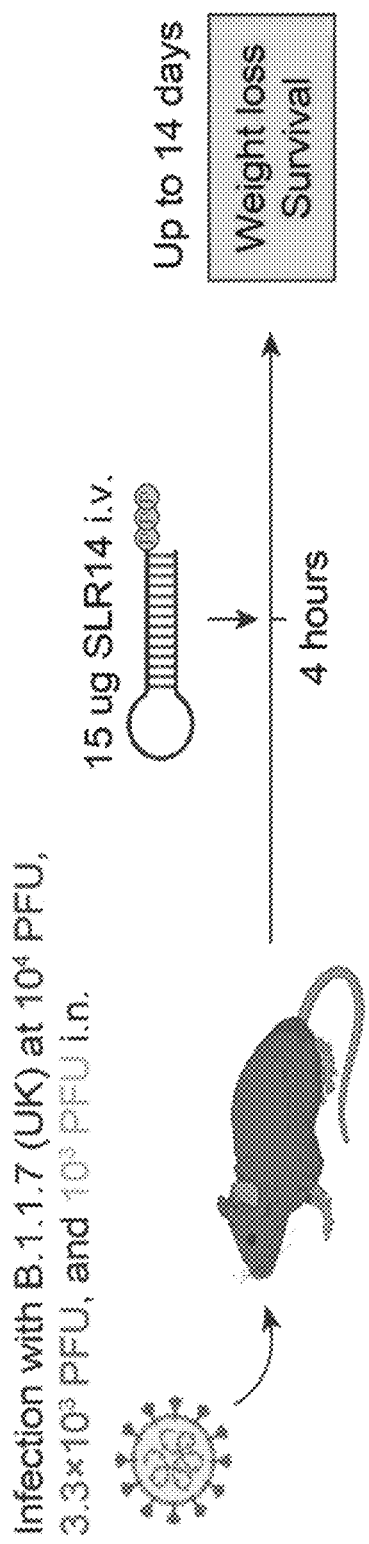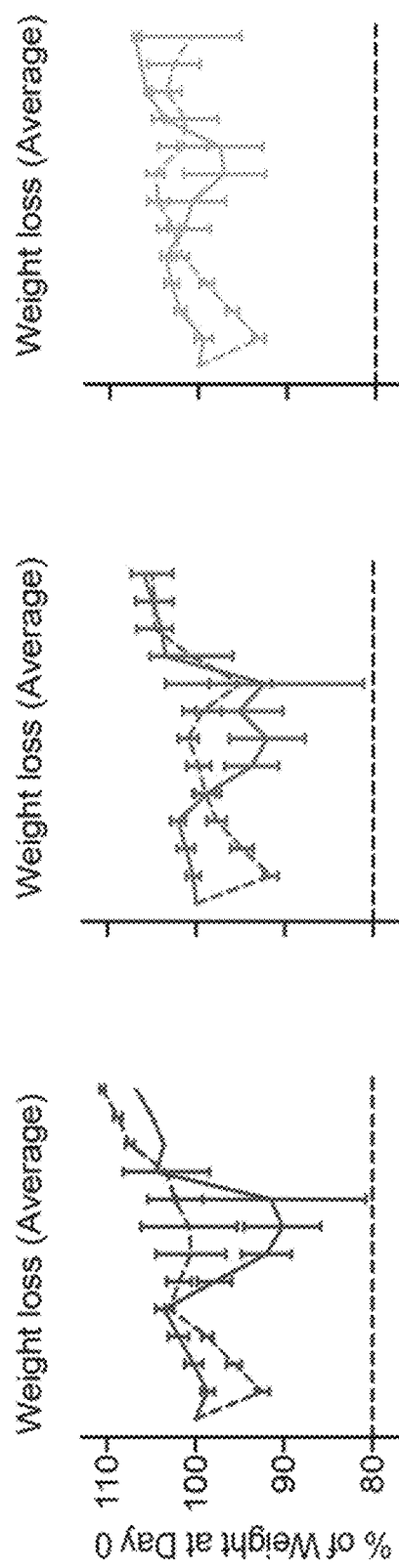

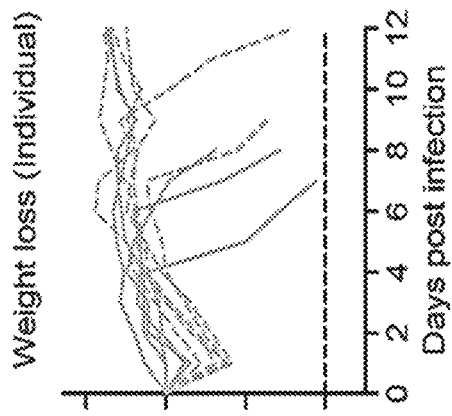
FIG. 26C
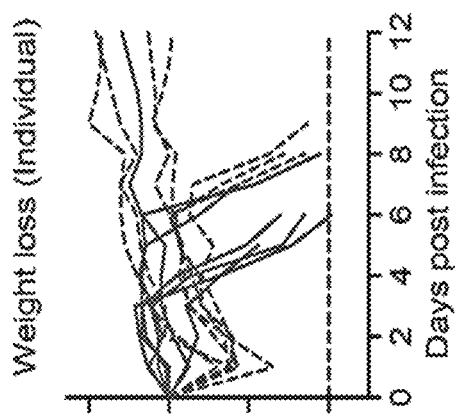
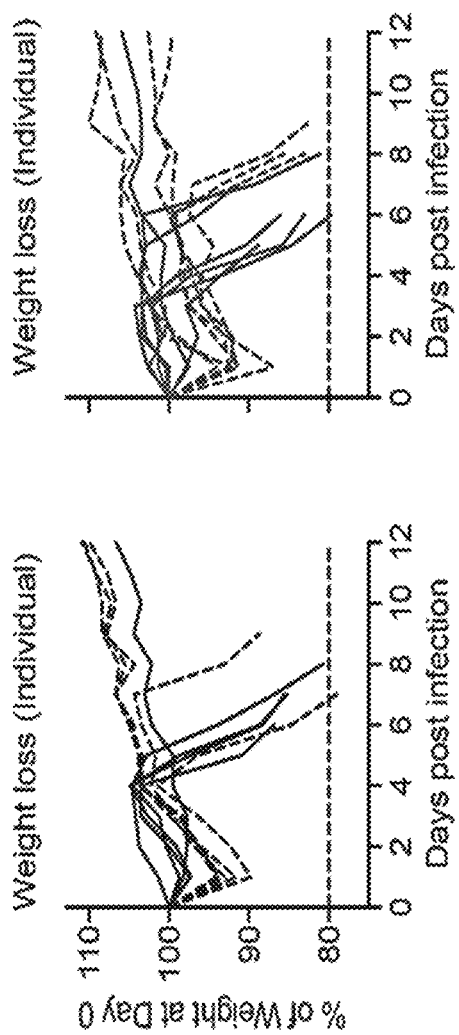
FIG. 26D
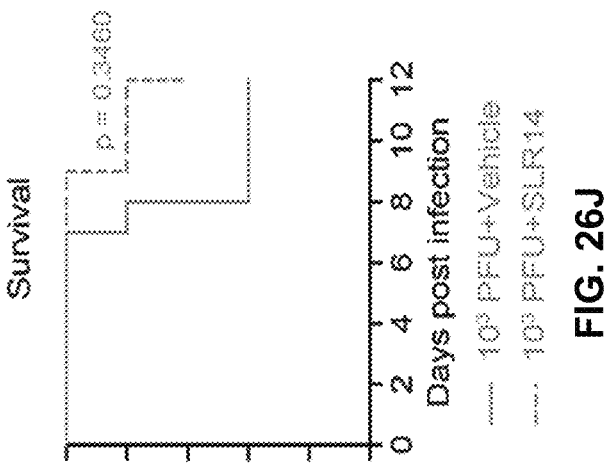
FIG. 26F
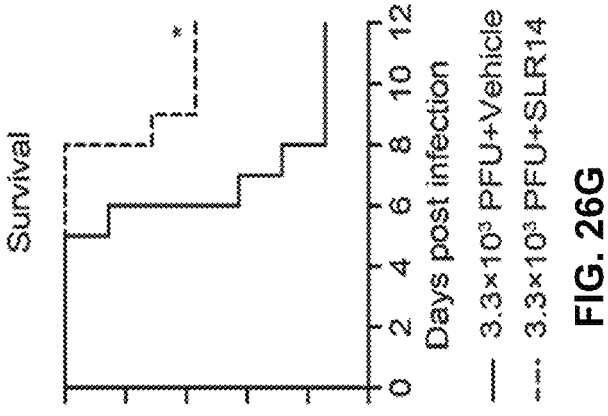
FIG. 26G
FIG. 26I
FIG. 26J
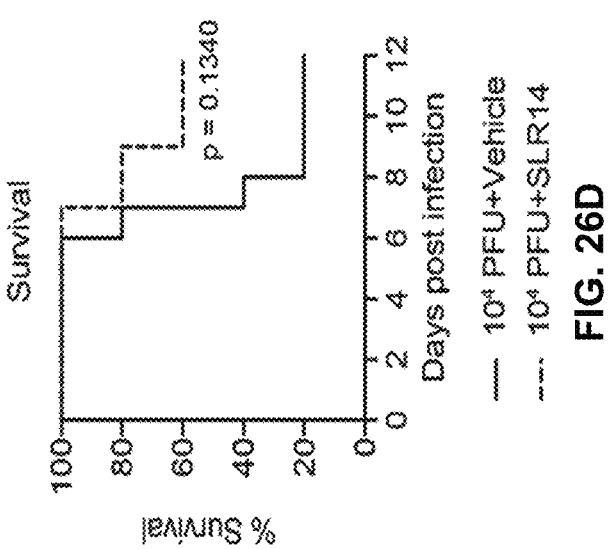

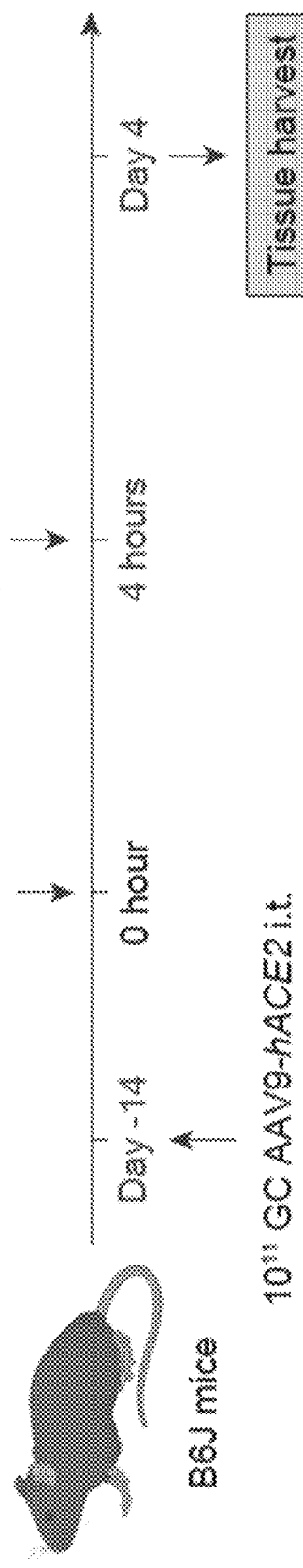
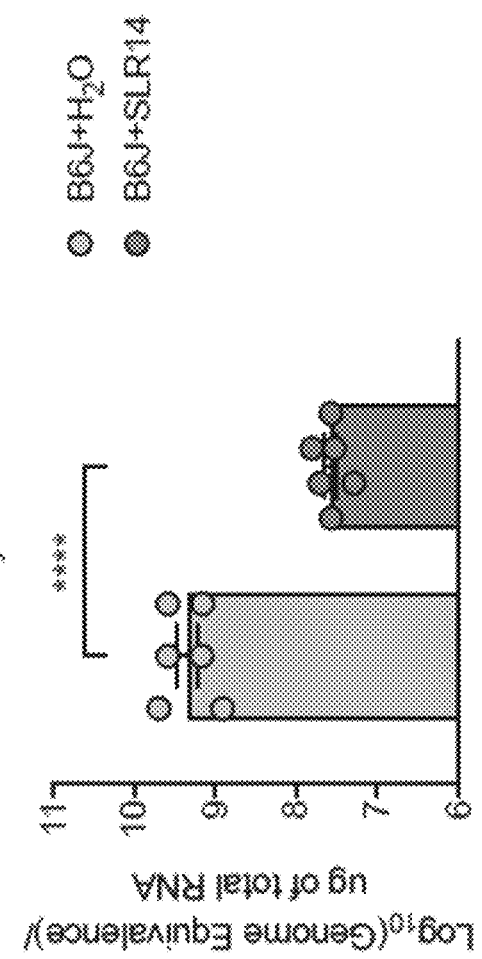
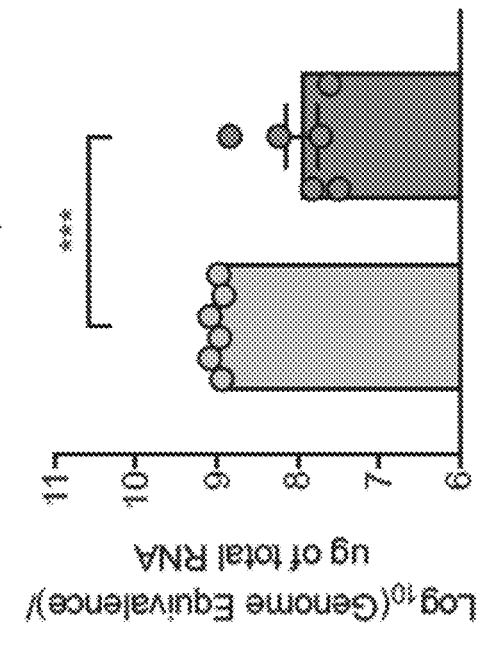
FIG. 29A
FIG. 29B
FIG. 29C

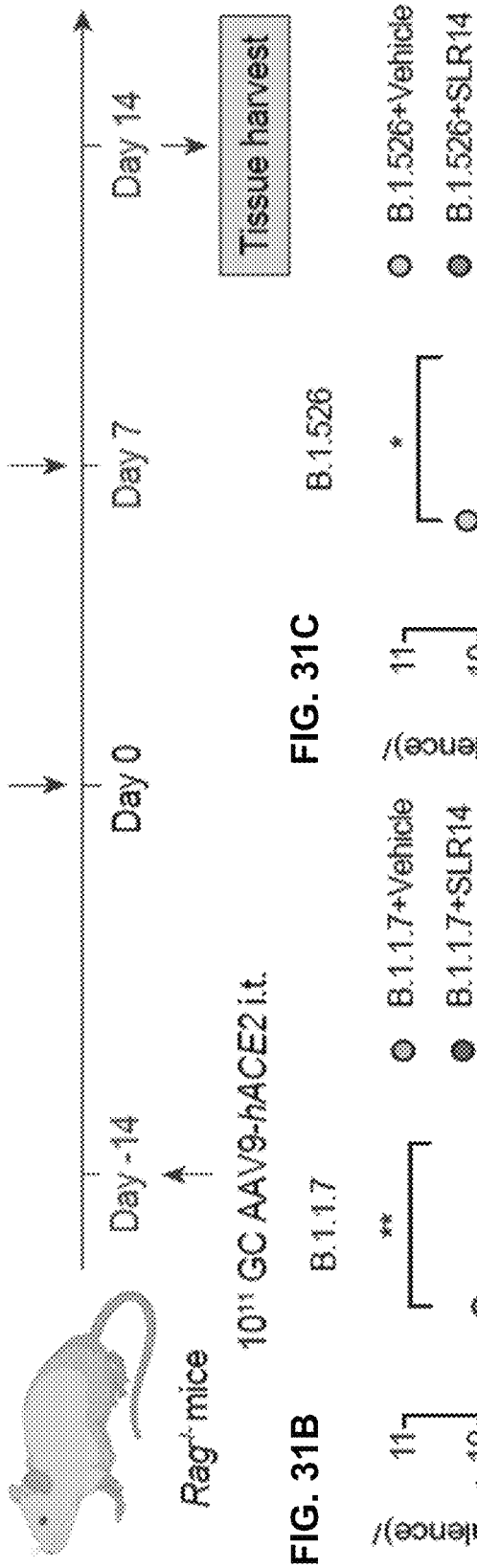
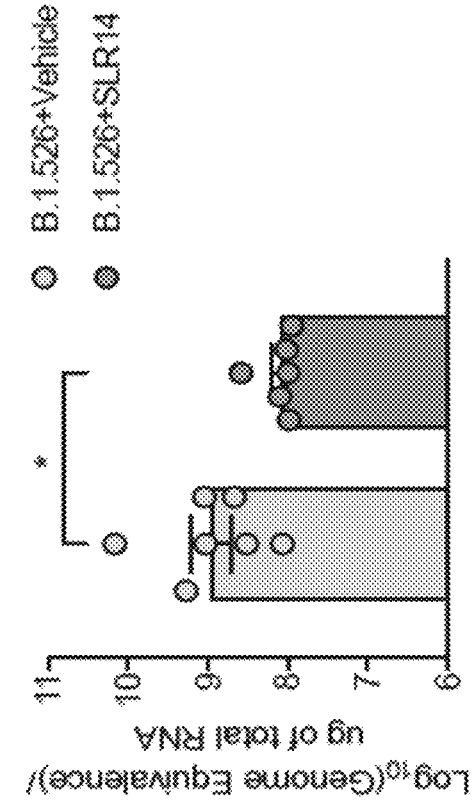
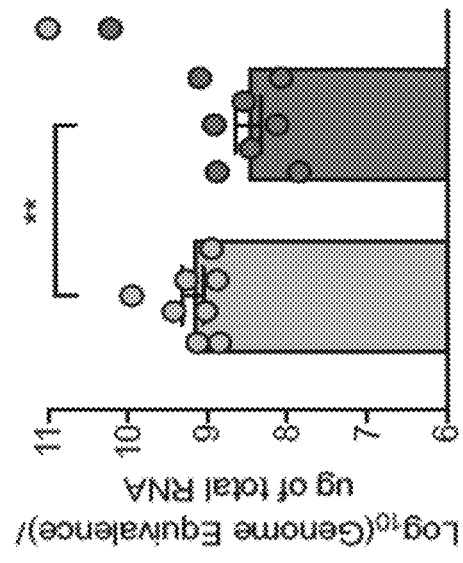
FIG. 31A
FIG. 31B
FIG. 31C

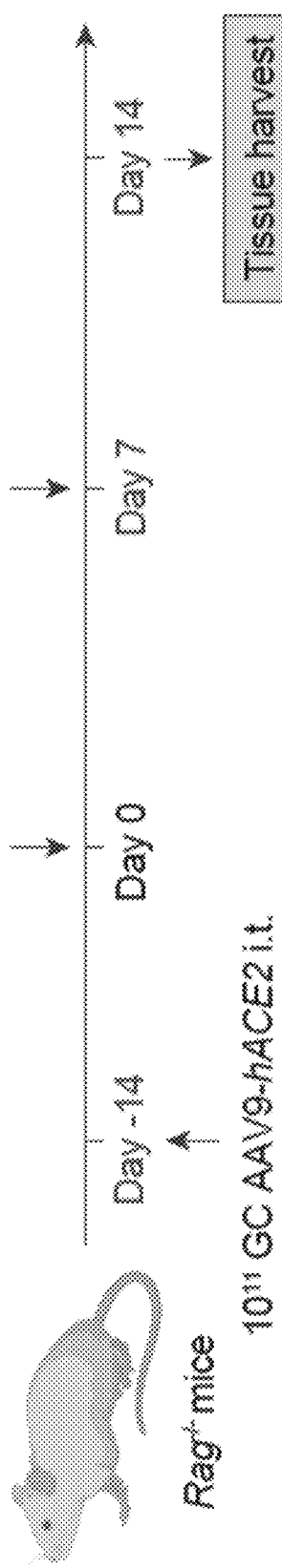
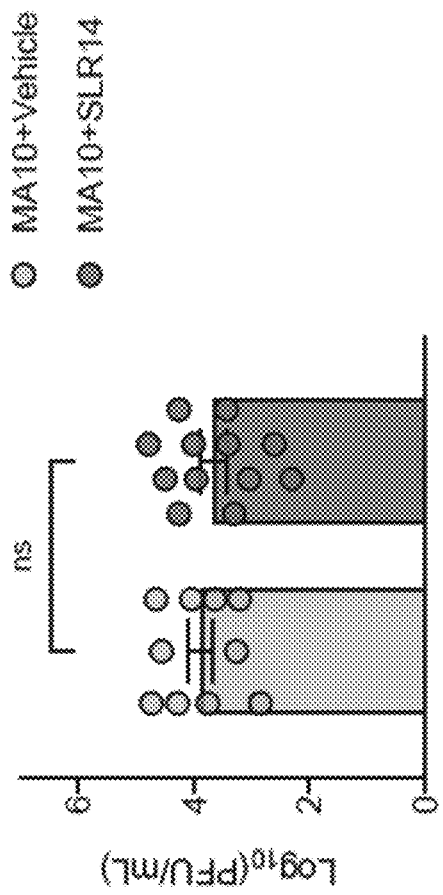
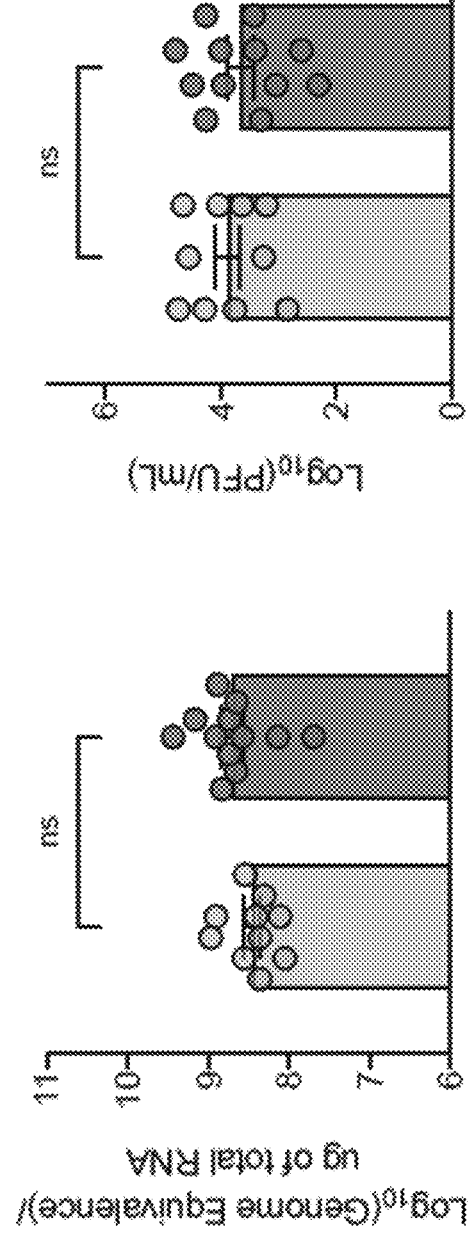
FIG. 32A
FIG. 32B
FIG. 32C

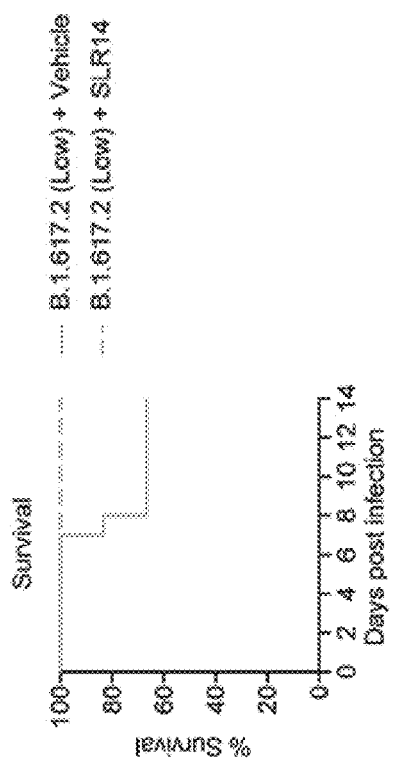
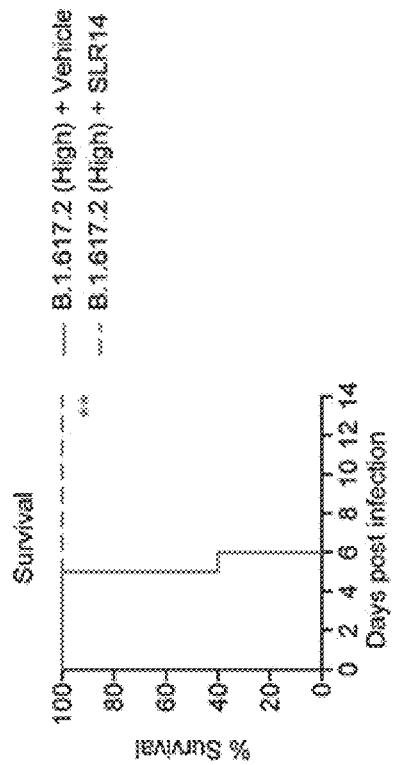
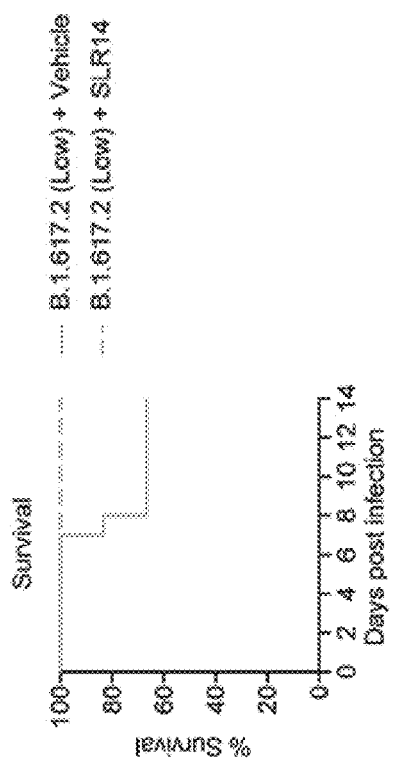
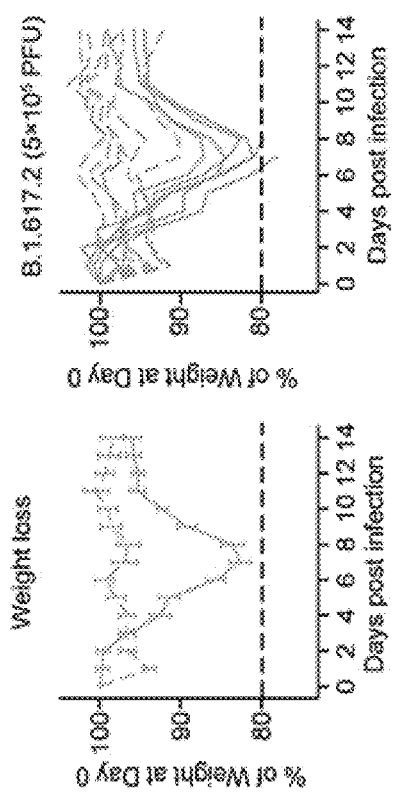
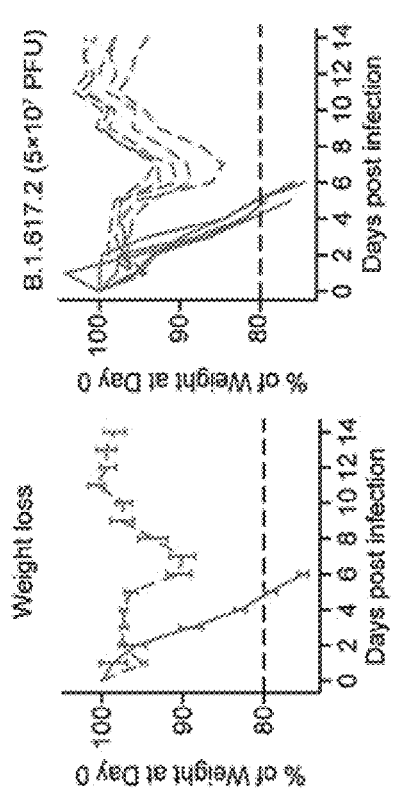

METHODS FOR TREATING SARS-COV-2 INFECTION

CROSS-REFERENCE TO RELATED APPLICATIONS

This application is a continuation-in-part of, and claims priority under 35 U.S.C. § 111(a) to, International Application No. PCT/US2021/062632 filed Dec. 9, 2021, which claims priority under 35 U.S.C. § 120 to U.S. application Ser. No. 17/115,968 filed Dec. 9, 2020, and claims priority under 35 U.S.C. § 119(e) to U.S. Provisional Applications No. 63/158,726 filed Mar. 9, 2021 and No. 63/210,869 filed Jun. 15, 2021, all of which are hereby incorporated by reference in their entireties.

STATEMENT REGARDING FEDERALLY SPONSORED RESEARCH OR DEVELOPMENT

This invention was made with government support under RO1 AI089826-03 awarded by the National Institutes of Health (NIH). The government has certain rights in the invention.

SEQUENCE LISTING

The ASCII text file named "047162-7317US3(01620)_Seq Listing_ST25" created on Jun. 13, 2022, comprising 1.36 Kbytes, is hereby incorporated by reference in its entirety.

BACKGROUND OF THE DISCLOSURE

RIG-I (retinoic acid-inducible gene I) is a cytosolic pattern recognition receptor (PRR) responsible for the type-1 interferon (IFN1) response. RIG-I plays a key role in the innate immune system response to infection by a foreign organism, such as a bacterium or a virus. RIG-I is a helical ATP-dependent DExD/H box RNA helicase, that recognizes short viral double-stranded RNA (dsRNA) in the cytosol during a viral infection or other irregular RNAs (i.e., non-coding RNAs). Once activated by the dsRNA, the N-terminus caspase activation and recruitment domains (CARDs) migrate and bind with CARDs attached to mitochondrial antiviral signaling protein (MAVS) to activate the signaling pathway for IFN1. IFN1s have three main functions: to limit the virus from spreading to nearby cells, promote an innate immune response, including inflammatory responses, and help activate the adaptive immune system.

Orthomyxoviridae is a family of negative-sense RNA viruses. It includes 7 genera: Alphainfluenzavirus, Betainfluenzavirus, Deltainfluenzavirus, Gammainfluenzavirus, Isavirus, Thogotovirus, and Quaranjavirus. The first 4 genera contain viruses that cause influenza in vertebrates, including humans, birds (see also avian influenza), and other mammals. Isaviruses infect salmon, while the thogotoviruses and quaranjaviruses are arboviruses. Alphainfluenzaviruses infect humans, other mammals, and birds, and cause all flu pandemics. Influenza A, influenza B, and influenza C viruses are influenza genera known to infect humans. Influenza A viruses are further classified, based on the viral surface proteins hemagglutinin (HA or H) and neuraminidase (NA or N). Sixteen H subtypes (or serotypes) and nine N subtypes of influenza A virus have been identified, with the highest virulence strains among humans including H1N1, H2N2, H3N2, H5N1, H7N7, H1N2, H9N2, H7N2, H7N3, and H10N7.

Coronavirus disease 2019 (COVID-19) is an infectious disease caused by a recently isolated virus known as severe acute respiratory syndrome Coronavirus 2 (SARS-CoV-2). COVID-19 is now an ongoing global pandemic, sickening about 4.5 million people and causing more than 300,000 deaths worldwide. Currently there are no available vaccines or antiviral treatments for the treatment or prevention of COVID-19.

Common symptoms of COVID-19 include fever, cough, fatigue, shortness of breath, and loss of smell and taste. Most COVID-19 infections result in mild symptoms and resolve on their own, but some cases progress to acute respiratory distress syndrome (ARDS), which is associated with dangerously low blood oxygen levels. Further COVID-19 complications include pneumonia, multi-organ failure, septic shock, heart failure, arrhythmias, heart inflammation, and/or blood clots.

While most individuals effectively clear SARS-CoV-2 infection, growing evidence suggests that infection in immunocompromised patients, such as those with severe forms of B cell and antibody deficiency, can become chronic. In these patients, persistent infection can also foster continuous intra-host viral evolution and lead to further emergence of immune-evasive variants, likely as a result of selective pressure driven by insufficient natural or transferred antibodies. While some patient case reports have used convalescent plasma to treat chronic SARS-CoV-2 infection, currently there are no approved therapeutic options. Although vaccines currently approved against SARS-CoV-2 are effective at preventing severe disease and death in individuals with an intact immune system, their immunogenicity is significantly attenuated in immunocompromised patients, eliciting suboptimal humoral immune responses. Therefore, therapeutic strategies that exert strong antiviral effect independent of adaptive immunity in the setting of immunosuppression are in dire need.

Since the initial outbreak, several SARS-CoV-2 variants have rapidly emerged with enhanced transmissibility and altered immunogenicity. The B.1.1.7 variant is more transmissible than other variants (~50% increase) and is spreading rapidly around the globe. While mutations accumulated by B.1.1.7 seem to have negligible impact on infection- and vaccine-induced antibody immunity, other variants have been found to acquire mutations on their spike proteins that can evade antibody targeting. Notably, variant B.1.351 and P.1 have both demonstrated considerable resistance to antibody binding and neutralization. The more recent variant B.1.526 has also exhibited some level of antibody evasion. In addition, these variants harbor mutations outside the spike protein that may enable strong antagonism of the host antiviral innate immunity. In this context, the containment of COVID-19 will require prophylactic and/or therapeutic antiviral strategies that afford cross-variant protection.

There still remains a need in the art for compositions and method for treating, ameliorating, and/or preventing viral infections, including treating and/or ameliorating the infection, providing pre-exposure prophylaxis, providing post-exposure prophylaxis, preventing onset of the infection, and/or reducing severity of the infection. The present disclosure satisfies this need in the art.

SUMMARY OF THE DISCLOSURE

In some aspects, the instant specification is directed to the following non-limiting embodiments:

Embodiment 1: A method for treating, ameliorating, and/or preventing viral infection, and/or ameliorating, minimizing, reversing, and/or preventing persistent viral infection, and/or minimize or prevent viral infection-derived mortality and/or lethality, in a subject, the method comprising administering to the subject a therapeutically effective amount of a nucleic acid molecule, wherein the nucleic acid molecule comprises a double-stranded section of less than 19 base pairs, and wherein the administering induces type I interferon production in at least one cell of the subject.

Embodiment 2: A method for treating, ameliorating, and/or preventing viral infection in a tumor-bearing subject, the method comprising administering to the tumor-bearing subject a therapeutically effective amount of a nucleic acid molecule, wherein the nucleic acid molecule comprises a double-stranded section of less than 19 base pairs, and wherein the administering induces type I interferon production in at least one cell of the subject.

Embodiment 3: A method for treating, ameliorating, and/or preventing viral infection in an immune-compromised and/or immunodeficient subject, the method comprising administering to the tumor-bearing subject a therapeutically effective amount of a nucleic acid molecule, wherein the nucleic acid molecule comprises a double-stranded section of less than 19 base pairs, and wherein the administering induces type I interferon production in at least one cell of the subject.

Embodiment 4: The method of any one of embodiments 1-3, wherein the administering takes place before the subject is exposed to the virus.

Embodiment 5: The method of any one of embodiments 1-3, wherein the administering takes place after the subject is exposed to the virus.

Embodiment 6: The method of any one of embodiments 1-3, wherein the administering reduces, minimizes, and/or prevents viral replication in the subject.

Embodiment 7: The method of any one of embodiments 1-3, wherein the administering reduces recovery time for, eliminates, or minimizes at least one complication from the viral infection.

Embodiment 8: The method of embodiment 7, wherein the at least one complication comprises at least one of weight loss, fever, cough, fatigue, muscle and/or body ache, nausea, vomiting, diarrhea, shortness of breath, loss of smell and/or taste, acute respiratory distress syndrome (ARDS), low blood oxygen levels, pneumonia, multi-organ failure, septic shock, heart failure, arrhythmias, heart inflammation, blood clots, and death.

Embodiment 9: The method of any one of embodiment 1-3, wherein the virus comprises at least one of hepatitis C virus, hepatitis B virus, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV), and smallpox virus.

Embodiment 10: The method of any one of embodiments 1-3, wherein the virus comprises an Orthomyxoviridae virus.

Embodiment 11: The method of embodiment 10, wherein the Orthomyxoviridae virus comprises at least one of an Alphainfluenzavirus, Betainfluenzavirus, Deltainfluenzavirus, Gammainfluenzavirus, Isavirus, Thogotovirus, and Quaranjavirus.

Embodiment 12: The method of embodiment 11, wherein the Alphainfluenzavirus comprises at least one of Influenza A virus, Influenza B virus, and Influenza C virus.

Embodiment 13: The method of any one of embodiment 1-3, wherein the virus comprises a Coronavirus.

Embodiment 14: The method of embodiment 13, wherein the Coronavirus comprises at least one of an Alphacoronavirus, a Betacoronavirus, a Gammacoronavirus, and a Deltacoronavirus.

Embodiment 15: The method of embodiment 14, wherein the Coronavirus comprises at least one of MERS-CoV, SARS-CoV, and SARS-CoV 2.

Embodiment 16: The method of embodiment 14, wherein the SARS-CoV-2 infection is caused by at least one variant strain of SARS-CoV-2; in certain embodiments, the SARS-CoV-2 comprises at least one variant selected from B.1.1.7 (Alpha), B.1.351 (Beta), P.1 (Gamma), B.1.617.2 (Delta), B.1.429/B.1.427 (Epsilon), B.1.617.1 (Kappa), B.1.525 (Eta), B.1.526 (Iota), P.3 (Theta), P.2 (Zeta), and B.1.1.529 (Omicron).

Embodiment 17: The method of any one of embodiments 15-16, wherein the SARS-CoV-2 comprises at least one variant selected from A.1-A.6, B.3-B.7, B.9, B.10, B.13-B.16, B.2, B.1 lineage, P.1, P.2, P.3, and R.1.

Embodiment 18: The method of embodiment 17, wherein the B.1 lineage comprises at least one of (including, but not limited to, B.1, B.1.1, B.1.1.7, B.1.1.7 with E484K, B.1.2, B.1.5-B.1.72, B.1.9, B.1.13, B.1.22, B.1.26, B.1.37, B.1.3-B.1.66, B.1.177, B.1.243, B.1.313, B.1.351, B.1.427, B.1.429, B.1.525, B.1.526, B.1.526.1, B.1.526.2, B.1.617, B.1.617.1, B.1.617.2, B.1.617.3, B.1.619, B.1.620, and B.1.621.

Embodiment 19: The method of embodiment 1, wherein the subject suffers from long COVID.

Embodiment 20: The method of embodiment 2, wherein the tumor comprises a cancer selected from biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer, or renal cancer.

Embodiment 21: The method of embodiment 2, wherein the tumor comprises a cancer selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basalioma, colon carcinoma, cervical dysplasia, and Kaposi's sarcoma (AIDS-related and non-AIDS related).

Embodiment 22: The method of any one of embodiments 1-3, wherein the nucleic acid molecule is a ribonucleic acid (RNA) molecule.

Embodiment 23: The method of any one of embodiments 1-3, wherein the nucleic acid molecule is single stranded and comprises a first nucleotide sequence, which 5'-end is conjugated to one end of an element selected from the group consisting of a loop and a linker, wherein the other end of the element is conjugated to the 3'-end of a second nucleotide sequence, wherein the first nucleotide sequence is substantially complementary to the second nucleotide sequence, wherein the first nucleotide sequence and the second nucleotide sequence can hybridize to form a double-stranded section, whereby the nucleic acid molecule forms a hairpin structure.

Embodiment 24: The method of embodiment 23, wherein the nucleic acid molecule forms a hairpin structure with a 3'-overhang.

Embodiment 25: The method of embodiment 24, wherein the overhang comprises one, two, or three non-base pairing nucleotides.

Embodiment 26: The method of embodiment 23, wherein the linker is free of a nucleoside, nucleotide, deoxynucleoside, or deoxynucleotide, or any surrogates or modifications thereof.

Embodiment 27: The method of embodiment 23, wherein the linker is free of a phosphate backbone, or any surrogates or modifications thereof.

Embodiment 28: The method of embodiment 23, wherein the linker comprises at least one selected from the group consisting of an ethylene glycol group, an amino acid, and an alkylene chain.

Embodiment 29: The method of embodiment 23, wherein the linker comprises —(OCH2CH2)n-, wherein n is an integer ranging from 1 to 10.

Embodiment 30: The method of embodiment 23, wherein the nucleic acid molecule forms a hairpin structure with a blunt end.

Embodiment 31: The method of any one of embodiment 1-3, wherein the nucleic acid molecule comprises a double chain molecule and two blunt ends.

Embodiment 32: The method of any one of embodiment 1-3, wherein the nucleic acid molecule comprises a 5'-terminus group selected from the group consisting of a 5'-triphosphate and a 5'-diphosphate.

Embodiment 33: The method of any one of embodiment 1-3, wherein the nucleic acid molecule comprises a modified phosphodiester backbone.

Embodiment 34: The method of any one of embodiment 1-3, wherein the nucleic acid molecule comprises at least one 2'-modified nucleotide.

Embodiment 35: The method of embodiment 34, wherein the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

Embodiment 36: The method of any one of embodiments 1-3, wherein the nucleic acid molecule comprises at least one modified phosphate group.

Embodiment 37: The method of any one of embodiments 1-3, wherein the nucleic acid molecule comprises at least one modified base.

Embodiment 38: The method of any one of embodiments 1-3, wherein the double-stranded section comprises one or more mispaired bases.

Embodiment 39: The molecule of any one of embodiment 1-3, wherein the nucleic acid molecule comprises at least one abasic nucleotide.

BRIEF DESCRIPTION OF THE DRAWINGS

The following detailed description of non-limiting embodiments of the disclosure will be better understood when read in conjunction with the appended drawings. For the purpose of illustrating the disclosure, certain embodiments are shown in the drawings. It should be understood, however, that the disclosure is not limited to the precise arrangements and instrumentalities of the embodiments shown in the drawings.

FIG. 3A: Naïve C57BL/6J mice (male, 8 weeks) received SLR14 intravenous (i.v.) treatment 5 hours before (pre-treated) or after (post-treated) intranasal (i.n.) challenge with PR8. The mice treated intravenously with vehicle (jetPEI) were used as controls. FIG. 3B: Body weight loss in SLR14- or vehicle-treated mice after PR8 challenge. FIG. 3C: Survival of SLR14- or vehicle-treated mice after PR8 challenge.

FIG. 4A illustrates a non-limiting treatment scheme: K18 mice were intranasally infected with 10' PFU SARS-CoV-2. 15 μg SLR14 or vehicle were intravenously administered either 16 hours before, 4 hours post, or 24 hours post infection. Weight loss and survival were monitored daily. FIG. 4B illustrates weight changes compared to day 0 (day of infection) of SLR14- and vehicle-treated K18 mice from day 0 to day 14. FIG. 4C illustrates survival, defined as 20% weight loss compared to day 0, of SLR14- and vehicle-treated K18 mice from day 0 to day 14. Mean±s.e.m., log-rank Mantel-Cox test (c); *P≤0.05, P≤0.01, *P≤0.001, ****P≤0.0001.

FIG. 5A-5K illustrate the finding that a single dose of SLR14 confers protection against lethal SARS-CoV-2 infection in human ACE2 transgenic K18 mice. FIG. 5A: Experimental scheme: K18-hACE2 mice were intranasally infected with $10^3$ PFU SARS-CoV-2 (2019n-CoV/USA_WA1/2020). 4 hours post infection, 15 μg SLR14 or vehicle were intravenously administered. Weight loss and survival were monitored daily up to 14 DPI. Death was recorded when mice were found dead in the cage, moribund, or at 80% of original body weight. In a separate cohort, lung tissues were collected for virological and immunological analysis 5 DPI.

FIGS. 5B-5C: Weight loss (FIG. 5B) and survival (FIG. 5C) of SLR14- and vehicle-treated K18-hACE2 mice from 1 to 14 DPI. FIGS. 5D-5E: Measurement of genomic viral RNA in the lung 5 DPI by reverse-transcription quantitative PCR (RT-qPCR) against SARS-CoV-2 N gene using CDCN1 (FIG. 5D) or CDCN2 (FIG. 5E) primer-probe sets. FIG. 5F: Measurement of infectious virus titer in the lung 5 DPI by plaque assay. Limit of detection (LOD): $10^2$ PFU/mL. FIGS. 5G-5I: Measurement of expression of interferon stimulated genes (ISG) Cxcl9 (FIG. 5G), Isg15 (FIG. 5H) and Usp18 (FIG. 5I) in the lung 5 DPI by RT-qPCR. FIGS. 5J-5K: Frequency of CD11b$^+$CD64$^+$ macrophages of CD45$^+$ cells (FIG. 5J) and mean fluorescence intensity of MHCII on Ly6C$^{high}$ monocytes (FIG. 5K) in the lung 5 DPI by flow cytometry. Mean±s.e.m.; Statistical significance was calculated by log-rank Mantel-Cox test (FIG. 5C) or one-way ANOVA followed by Tukey correction (FIGS. 5D-5K); *$P \leq 0.05$, $P \leq 0.01$, *$P \leq 0.001$, ****$P \leq 0.0001$. Data are representative of two independent experiments.

FIG. 7A: Treatment scheme—K18 mice were intranasally infected with $10^3$ PFU SARS-CoV-2. 15 µg SLR14 or vehicle were intravenously administered either 16 hours before, 4 hours post, or 24 hours post infection. Weight loss and survival were monitored daily. FIG. 7B: Weight changes compared to day 0 (day of infection) of SLR14- and vehicle-treated K18 mice from day 0 to day 14 were measured. FIG. 7C: Survival, defined as 20% weight loss compared to day 0, of SLR14- and vehicle-treated K18 mice from day 0 to day 14 was measured. Mean±s.e.m., log-rank Mantel-Cox test (c); *$P \leq 0.05$, $P \leq 0.01$, *$P \leq 0.001$, ****$P \leq 0.0001$.

FIG. 8A: Treatment scheme—2 hours before infection, K18 mice were intraperitoneally treated with 2 mg of anti-IFNAR blocking antibodies or PBS, followed by intranasal infection with $10^3$ PFU SARS-CoV-2. 15 µg SLR14 or vehicle were intravenously administered 4 hours post infection. Weight loss and survival were monitored daily. FIG. 8B: Weight changes compared to day 0 (day of infection) of anti-IFNAR- and PBS-treated K18 mice from day 0 to day 14 were measured. FIG. 8C: Survival, defined as 10% weight loss compared to day 0, of anti-IFNAR- and PBS-treated K18 mice from day 0 to day 14 was measured. Mean±s.e.m., two-way ANOVA followed by Sidak correction (b), log-rank Mantel-Cox test (c); *$P \leq 0.05$, $P \leq 0.01$, *$P \leq 0.001$, ****$P \leq 0.0001$.

FIGS. 9A-9B illustrate a non-limiting experiment testing the effect of therapeutic SLR14 in treating persistent infection and long COVID.

FIG. 10A: Rag1$^{-/-}$ mice were first intratracheally transduced with $10^{11}$ genome copies of AAV9-hACE2, allowed to rest for 14 days, followed by intranasal infection with $10^6$ PFU SARS-CoV-2. 15 µg SLR14 or vehicle were intravenously administered 7 days post infection. Lungs were collected 7 days post SLR14 treatment for assessment of viral load. FIG. 10B: SARS-CoV-2 N gene expression from lung homogenates was measured 14 days post infection by quantitative PCR. FIG. 10C: Infectious viral burden from lung homogenates was measured 14 days post infection by plaque assays. Mean±s.e.m., Student's t-test (b-c); *$P \leq 0.05$, $P \leq 0.01$, *$P \leq 0.001$, ****$P \leq 0.0001$.

FIG. 11A: Naïve C57BL/6J mice (male, 8 weeks) received SLR14 intravenous (i.v.) treatment 5 hours before (pre-treated) or after (post-treated) intranasal (i.n.) challenge with PR8. The mice treated intravenously with vehicle (jetPEI) were used as controls. FIG. 11B: Body weight loss in SLR14- or vehicle-treated mice after influenza virus PR8 challenge. FIG. 11C: The survival of SLR14- or vehicle-treated mice after PR8 challenge.

FIGS. 12A-12F illustrate the finding that endogenous Flu-specific CD8+ T cell priming is impaired in tumor-bearing mice. FIG. 12A: Tumor-bearing mice (day 14) or the mice without tumor were intranasally (i.n.) infected with 150 PFU influenza virus PR8 in 30 µl PBS. PR8-specific CD8+ T cells in the blood at day 8 post infection were measured by using tetramer staining. FIGS. 12B-12C: Percentage of CD44+CD8+Tetramer+ T cells in the blood at day 8 post infection. FIG. 12D: Body weight change after PR8 infection. FIG. 12E: Survival of the mice after PR8 infection. FIG. 12F: Viral load (shown by the number of plaque) in the lung at day 8 post i.n. infection of 30 k PFU X31-OVA. *: $p<0.05$. **: $p<0.01$.

FIG. 13A: Tumor-bearing mice (day 14) were intravenously (i.v.) treated with 25 µg SLR14 5 hours before or after 150 PFU PR8 intranasal (i.n.) infection. Vehicle-treated mice were used as control. FIG. 13B: Body weight change of the mice after infection. FIG. 13C: Survival of the mice after infection.

FIG. 14A: Tumor-bearing mice (day 14) were intranasally (i.n.) infected with 8 k PFU SARS-CoV-2 in 50 µl PBS. FIG. 14B: Body weight change of the mice after infection. FIG. 14C: Survival of the mice after infection.

FIG. 15A: Tumor-bearing mice (day 14) were intravenously (i.v.) treated with 25 µg SLR14 12 hours before or after 20 k PFU SARS-CoV-2 intranasal (i.n.) infection. Vehicle-treated mice were used as control. FIG. 15B: Body weight change of the mice after infection. FIG. 15C: Survival of the mice after infection.

FIGS. 16A-16D illustrate that SLR14 alleviates inflammatory burden and reduces lung pathology in lethal SARS-CoV-2 infection. FIG. 16A: Treatment scheme—K18 mice were intranasally infected with $5 \times 10^4$ PFU SARS-CoV-2. 4 hours post infection, 15 µg SLR14 or vehicle were intravenously administered. 5 days post infection, lung tissues were collected. FIGS. 16B-16D: Pulmonary immune responses following SARS-CoV-2 infection. Frequency of CD11b$^+$CD64$^+$ macrophages (FIG. 16B), Ly6C$^{high}$ monocytes (FIG. 16C) as well as mean fluorescence intensity of MHCII on Ly6C$^{high}$ monocytes (FIG. 16D) were measured by flow cymetry. Mean±s.e.m., one-way ANOVA followed by Tukey correction (FIGS. 16B-16D); *$P \leq 0.05$, $P \leq 0.01$, *$P \leq 0.001$, ****$P \leq 0.0001$.

FIGS. 17A-17J illustrate the finding that SLR14-mediated protection against SARS-CoV-2 depends on IFN-I signaling. FIG. 17A: Experimental scheme: K18-hACE2 mice were intranasally infected with $10^3$ PFU SARS-CoV-2 (2019n-CoV/USA_WA1/2020). 2 hours before infection, 15 µg SLR14 or vehicle were intravenously administered. 24 hours before SLR14 injection, half of SLR14-treated mice was additionally given 2 mg anti-IFNAR antibodies. Weight loss and survival were monitored daily up to 14 DPI. Death was recorded when mice were found dead in the cage, moribund, or at 80% of original body weight. In a separate cohort, lung tissues were collected for virological analysis 3, 6, and 8 DPI. FIGS. 17B-17D: Weight loss (FIGS. 17B-17C) and survival (FIG. 17D) of SLR14- and vehicle-treated K18-hACE2 mice from 1 to 14 DPI. FIGS. 17E-17G: Measurement of genomic viral RNA in the lung parenchyma 3, 6, and 8 DPI by RT-qPCR using the CDCN2 primer-probe set. FIGS. 17H-17J: Measurement of genomic viral RNA in the trachea 3, 6, and 8 DPI by RT-qPCR using the CDCN2 primer-probe set. Mean±s.e.m.; Statistical significance was calculated by log-rank Mantel-Cox test (FIG. 17D) or one-way ANOVA followed by Tukey correction (FIGS. 17E-17J); $*P \leq 0.05$, $P \leq 0.01$, $*P \leq 0.001$, $****P \leq 0.0001$. Data are representative of two independent experiments.

FIGS. 18A-18G illustrate the finding that SLR14 treatment timing relative to SARS-CoV-2 infection determines protective activities. FIG. 18A: Experimental scheme: K18-hACE2 mice were intranasally infected with $10^3$ PFU SARS-CoV-2 (2019n-CoV/USA_WA1/2020). 15 µg SLR14 were intravenously administered at 16 hours before, 2 hours before, 4 hours after, 24 hours after, 48 hours after, or 72 hours after infection. Weight loss and survival were monitored daily up to 14 DPI. Death was recorded when mice were found dead in the cage, moribund, or at 80% of original body weight. FIGS. 18B-18D: Weight loss (FIGS. 18B-18C) and survival (FIG. 18D) of prophylactically SLR14- and vehicle-treated K18-hACE2 mice from 1 to 14 DPI. FIGS. 18E-18G: Weight loss (FIGS. 18E-18F) and survival (FIG. 18G) of therapeutically SLR14- and vehicle-treated K18-hACE2 mice from 1 to 14 DPI. Mean±s.e.m.; Statistical significance was calculated by log-rank Mantel-Cox test (FIGS. 18D & 18G); $*P \leq 0.05$, $P \leq 0.01$, $*P \leq 0.001$, $****P \leq 0.0001$. Data are pooled from of three independent experiments.

FIGS. 19A-19C illustrate the finding that therapeutic SLR14 cures persistent SARS-CoV-2 infection in immunodeficient mice through induction of IFN-I. FIG. 19A: Experimental scheme: $Rag^{-/-}$ mice were intratracheally administered with $10^{11}$ genome copies of AAV9-hACE2 and let rest for 2 weeks before intranasal infection with $10^6$ PFU SARS-CoV-2 (2019n-CoV/USA_WA1/2020). 15 µg SLR14 or vehicle were intravenously administered 7 DPI. 24 hours before SLR14 injection, half of SLR14-treated mice was additionally given 2 mg anti-IFNAR antibodies. Lung tissues were collected for virological analysis 14 DPI. FIG. 19B: Measurement of genomic viral RNA in the lung 14 DPI by RT-qPCR. FIG. 19C: Measurement of infectious virus in the lung 14 DPI by plaque assay. Limit of detection (LOD): $10^2$ PFU/mL. Mean±s.e.m.; Statistical significance was calculated by one-way ANOVA followed by Tukey correction (FIGS. 19B-19C); $*P \leq 0.05$, $P \leq 0.01$, $*P \leq 0.001$, $****P \leq 0.0001$. Data are pooled from two independent experiments.

FIGS. 20A-20M illustrate the finding that SLR14 affords broadly cross-reactive protection against emerging SARS-CoV-2 variants. FIG. 20A: Experimental scheme: K18-hACE2 mice were intranasally infected with $10^4$ PFU P.1, B.1.526, B.1.351, or B.1.1.7 variants. 15 µg SLR14 or vehicle were intravenously administered at 4 hours after infection. Weight loss and survival were monitored daily up to 14 DPI. Death was recorded when mice were found dead in the cage, moribund, or at 80% of original body weight. FIGS. 20B-20D: Weight loss (FIGS. 20B-20C) and survival (FIG. 20D) of SLR14- and vehicle-treated K18-hACE2 mice from 1 to 14 DPI following P1 infection. FIGS. 20E-20G: Weight loss (FIGS. 20E-20F) and survival (FIG. 20G) of SLR14- and vehicle-treated K18-hACE2 mice from 1 to 14 DPI following B.1.526 infection. FIGS. 20H-20J: Weight loss (FIGS. 20H-20I) and survival (FIG. 20J) of SLR14- and vehicle-treated K18-hACE2 mice from 1 to 14 DPI following B.1.351 infection. FIGS. 20K-20M: Weight loss (FIGS. 20K-20L) and survival (FIG. 20M) of SLR14- and vehicle-treated K18-hACE2 mice from 1 to 14 DPI following B.1.1.7 infection. Mean±s.e.m.; Statistical significance was calculated by log-rank Mantel-Cox test (FIGS. 20D, 20G, 20J, 20M); $*P \leq 0.05$, $P \leq 0.01$, $*P \leq 0.001$, $****P \leq 0.0001$. Data are pooled from two independent experiments.

FIGS. 21A-21D illustrate the finding that SLR14 mediate IFN-I signaling-dependent viral control in the upper respiratory tract late, but not early, during the infection. FIG. 21A: Experimental scheme: K18-hACE2 mice were intranasally infected with $10^3$ PFU SARS-CoV-2 (2019n-CoV/USA_WA1/2020). 2 hours before infection, 15 µg SLR14 or vehicle were intravenously administered. 24 hours before SLR14 injection, half of SLR14-treated mice was additionally given 2 mg anti-IFNAR antibodies. Nasal washes were collected for virological analysis 3, 6, and 8 DPI. FIGS. 21B-21D: Measurement of genomic viral RNA in the nasal wash 3, 6, and 8 DPI by RT-qPCR using the CDCN2 primer-probe set. Mean±s.e.m.; Statistical significance was calculated by one-way ANOVA followed by Tukey correction (FIGS. 21B-21D); $*P \leq 0.05$, $P \leq 0.01$, $*P \leq 0.001$, $****P \leq 0.0001$.

FIG. 22A: Experimental scheme: $Ifnar^{-/-}$ mice were intratracheally administered with $10^{11}$ genome copies of AAV9-hACE2 and let rest for 2 weeks before intranasal infection with $10^6$ PFU SARS-CoV-2 (2019n-CoV/USA_WA1/2020). 15 µg SLR14 or vehicle were intravenously administered at 4 hours after infection. Lung tissues were collected for virological analysis 4 DPI. FIG. 22B: Measurement of genomic viral RNA 4 DPI by RT-qPCR using the CDCN2 primer-probe set. Mean±s.e.m.; Statistical significance was calculated by one-way ANOVA followed by Tukey correction (FIG. 22B); $*P \leq 0.05$, $P \leq 0.01$, $*P \leq 0.001$, $****P \leq 0.0001$.

FIGS. 23A-23E illustrate the finding that early uptake of i.v. SLR14 is mainly mediated by lung epithelial cells and inflammatory monocyte-derived macrophages. FIG. 23A: Experimental scheme: K18-hACE2 mice were i.v. injected with 15 µg AF647-conjugated SLR14 or vehicle. Lung tissues were collected for SLR14 uptake analysis by flow cytometry 4 hours post injection. Lung tissues from vehicle-injected controls were also collected as negative controls. FIG. 23B: Frequency of indicated immune and non-immune cell types among $SLR14^+$ cells versus total lung cells. FIG. 23C: Frequency of indicated macrophage populations among $SLR14^+$ cells or total lung cells. FIG. 23D: Distribution index (frequency of a given cell type in the $SLR14^+$ compartment/frequency of all cells) of indicated immune and non-immune cell types. FIG. 23E: Distribution index of indicated macrophage populations.

FIGS. 24A-24C illustrate the finding that convalescent sera transfer cures persistent SARS-CoV-2 infection in immunodeficient mice. FIG. 24A: Experimental scheme: Rag$^{-/-}$ mice were intratracheally administered with $10^{11}$ genome copies of AAV9-hACE2 and let rest for 2 weeks before intranasal infection with $10^6$ PFU SARS-CoV-2 (2019n-CoV/USA_WA1/2020). 200 µL convalescent sera or PBS were intravenously administered 7 DPI. Lung tissues were collected for virological analysis 14 DPI. FIG. 24B: Measurement of genomic viral RNA in the lung 14 DPI by RT-qPCR. FIG. 24C: Measurement of infectious virus titer in the lung 14 DPI by plaque assay. Limit of detection (LOD) for plaque assay: $10^2$ PFU/mL. Mean±s.e.m.; Statistical significance was calculated by one-way ANOVA followed by Tukey correction (FIGS. 24B-24C); *P≤0.05, P≤0.01, *P≤0.001, ****P≤0.0001. Data are pooled from two independent experiments.

FIGS. 26A-26J illustrate the finding that post-exposure prophylactic SLR14 is partially protective against infection with the B.1.1.7 variant in K18-hACE2 mice. FIG. 26A: Experimental scheme: K18-hACE2 mice were intranasally infected with $10^4$, $3.3 \times 10^3$, or $10^3$ PFU B.1.1.7 variant. 15 µg SLR14 or vehicle were intravenously administered at 4 hours after infection. Weight loss and survival were monitored daily up to 14 DPI. Death was recorded when mice were found dead in the cage, moribund, or at 80% of original body weight. FIGS. 26B-26D: Weight loss (FIGS. 26B-26C) and survival (FIG. 26D) of SLR14- and vehicle-treated K18-hACE2 mice from 1 to 14 DPI following infection with $10^4$ PFU B.1.1.7. FIGS. 26E-26G: Weight loss (FIGS. 26E-26F) and survival (FIG. 26G) of SLR14- and vehicle-treated K18-hACE2 mice from 1 to 14 DPI following infection with $3.3 \times 10^3$ PFU B.1.1.7. FIGS. 26H-26J: Weight loss (FIGS. 26H-26I) and survival (FIG. 26J) of SLR14- and vehicle-treated K18-hACE2 mice from 1 to 14 DPI following infection with $10^3$ PFU B.1.1.7. Mean±s.e.m.; Statistical significance was calculated by log-rank Mantel-Cox test (FIGS. 26D, 26G, 26J); *P≤0.05, P≤0.01, *P≤0.001, ****P≤0.0001.

FIG. 27A: Gating strategies for identification of various immune and non-immune cell populations in the lung were used to generate FIGS. 23B-23E. FIG. 27B: Histogram examples of SLR14 uptake by epithelial cells and different macrophage subsets. Lung tissues from vehicle-treated mice were included as negative controls.

FIG. 28A: Experimental scheme: K18-hACE2 mice were intranasally infected with $10^3$ PFU SARS-CoV-2 (2019n-CoV/USA_WA1/2020). 2 hours before infection, 15 µg SLR14 or vehicle were intravenously administered. 24 hours before SLR14 injection, half of SLR14-treated mice was additionally given 2 mg anti-IFNAR antibodies. Brain tissues were collected for virological analysis 8 DPI. FIG. 28B: Measurement of genomic viral RNA in the brain 8 DPI by RT-qPCR using the CDCN2 primer-probe set. Mean±s.e.m.; Statistical significance was calculated by one-way ANOVA followed by Tukey correction (FIG. 28B); *P≤0.05, P≤0.01, *P≤0.001, ****P≤0.0001.

FIGS. 29A-29C illustrate the finding that SLR14 exerts strong antiviral effect in an AAV-based mouse model of SARS-CoV-2. FIG. 29A: Experimental scheme: B6J mice were intratracheally administered with $10^{11}$ genome copies of AAV9-hACE2 and let rest for 2 weeks before intranasal infection with $10^6$ PFU SARS-CoV-2 (2019n-CoV/USA_WA1/2020). 15 µg SLR14 or vehicle were intravenously administered 4 hours post infection. Lung tissues were collected for virological analysis 4 DPI. FIGS. 29B-29C: Measurement of genomic viral RNA in the lung parenchyma 2 DPI (FIG. 29B) and 4 DPI (FIG. 29C) by RT-qPCR using the CDCN2 primer-probe set. Mean±s.e.m.; Statistical significance was calculated by Students' t-test (FIGS. 29B-29C); *P≤0.05, P≤0.01, *P≤0.001, ****P≤0.0001. Data are representative of two independent experiments.

FIG. 30A: Experimental scheme: Rag$^{-/-}$ mice were intratracheally administered with $10^{11}$ genome copies of AAV9-hACE2 and let rest for 2 weeks before intranasal infection with $10^6$ PFU SARS-CoV-2 (2019n-CoV/USA_WA1/2020). 15 µg SLR14 or vehicle were intravenously administered 7 DPI. 24 hours before SLR14 injection, half of SLR14-treated mice was additionally given 2 mg anti-IFNAR antibodies. Trachea tissues were collected for virological analysis 14 DPI. FIG. 30B: Measurement of genomic viral RNA in the trachea 14 DPI by RT-qPCR. Mean±s.e.m.; Statistical significance was calculated by one-way ANOVA followed by Tukey correction (FIG. 30B); *P≤0.05, P≤0.01, *P≤0.001, ****P≤0.0001. Data are pooled from two independent experiments.

FIGS. 31A-31C illustrate the finding that single-dose SLR14 reduces genomic viral RNA in Rag$^{-/-}$ mice chronically infected with VOCs. FIG. 31A: Experimental scheme: Rag$^{-/-}$ mice were intratracheally administered with $10^{11}$ genome copies of AAV9-hACE2 and let rest for 2 weeks before intranasal infection with B.1.1.7 or B.1.526. 15 µg SLR14 or vehicle were intravenously administered 7 DPI. Lung tissues were collected for virological analysis 14 DPI. FIGS. 31B-31C: Measurement of genomic viral RNA in the lung from mice infected with B.1.1.7 (FIG. 31B) or B.1.526 (FIG. 31C) 14 DPI by RT-qPCR using the CDCN2 primer-probe set. Mean±s.e.m.; Statistical significance was calculated by Students' t-test (FIGS. 31B-31C); *P≤0.05, P≤0.01, *P≤0.001, ****P≤0.0001.

FIGS. 32A-32C illustrate the finding that mouse adapted SARS-CoV-2 demonstrates strong resistance to SLR14-mediated antiviral activity. FIG. 32A: Experimental scheme: Rag$^{-/-}$ mice were intratracheally administered with $10^{11}$ genome copies of AAV9-hACE2 and let rest for 2 weeks before intranasal infection with mouse-adapted SARS-CoV-2 MA10. 15 µg SLR14 or vehicle were intravenously administered 7 DPI. Lung tissues were collected for virological analysis 14 DPI. FIGS. 32B-32C: Measurement of genomic viral RNA and infectious virus titer in the lung from mice infected with MA10 14 DPI by RT-qPCR using the CDCN2 primer-probe set. Mean±s.e.m.; Statistical significance was calculated by Students' t-test (FIGS. 32B-32C); *P≤0.05, P≤0.01, *P≤0.001, ****P≤0.0001.

FIG. 33A: Experimental scheme: K18-hACE2 mice were intravenously administered with 15 µg SLR14 or vehicle. 3 hours post injection, BALF and lung tissues were collected for IFN ELISA and RT-qPCR. FIGS. 33B-33C: Measurement of IFN-I secretion in the BAL fluid by ELISA and various Ifna and Ifnb gene expression in the lung tissue by RT-qPCR from vehicle or SLR14 treated mice. FIGS. 33D-33E: Measurement of IFN-III secretion in the BAL fluid by ELISA and Ifnl gene expression in the lung tissue by RT-qPCR from vehicle or SLR14 treated mice. Mean±s.e.m.; Statistical significance was calculated by two-way ANOVA followed by Bonferroni correction (FIGS. 33B-33C) or Student's t-test (FIGS. 33D-33E); *P≤0.05, P≤0.01, *P≤0.001, ****P≤0.0001. Data are pooled from or representative of two independent experiments.

FIG. 34: H&E staining of lung sections from vehicle- (Left) or SLR14-treated (Right) K18-hACE2 mice 5 DPI. Images show low or high power magnification. Images are representative of n=5 per group. Scale bar, 500 µm.

FIG. 35A: Experimental scheme: K18-hACE2 mice were intranasally infected with $5 \times 10^2$ PFU SARS-CoV-2 (2019n-CoV/USA_WA1/2020). 4 hours post infection, infected K18-hACE2 mice were intravenously treated with 15 µg SLR14, $2 \times 10^4$ U rIFN-αA/D (low-dose), $2 \times 10^5$ U rIFN-αA/D (high-dose), 20 µg diABZI, or vehicle. Weight loss and survival were monitored daily up to 14 DPI. Death was recorded when mice were found dead in the cage, moribund, or at 80% of original body weight. FIGS. 35B-35D: Weight loss and survival of K18-hACE2 mice from 1 to 14 DPI. Mean±s.e.m.; Statistical significance was calculated by log-rank Mantel-Cox test (FIG. 35D); *P≤0.05, P≤0.01, *P≤0.001, ****P≤0.0001. Data are pooled from two independent experiments.

FIGS. 36A-36G illustrate the finding that SLR14 is highly effective against B.1.617.2 infection in vivo. FIG. 36A: Experimental scheme: K18-hACE2 mice were intranasally infected with the B.1.617.2 variant. 15 µg SLR14 or vehicle were intravenously administered at 4 hours after infection. Weight loss and survival were monitored daily up to 14 DPI. Death was recorded when mice were found dead in the cage, moribund, or at 80% of original body weight. FIGS. 36B-36D: Weight loss and survival of SLR14- and vehicle-treated K18-hACE2 mice from 1 to 14 DPI following $5 \times 10^5$ PFU (low-dose) B.1.617.2 infection. FIGS. 36E-36G: Weight loss and survival of SLR14- and vehicle-treated K18-hACE2 mice from 1 to 14 DPI following $5 \times 10^7$ PFU (high-dose) B.1.617.2 infection. Mean±s.e.m.; Statistical significance was calculated by log-rank Mantel-Cox test (FIG. 36G); *P≤0.05, P≤0.01, *P≤0.001, ****P≤0.0001. Data are pooled from two independent experiments.

DETAILED DESCRIPTION

Figure 1:
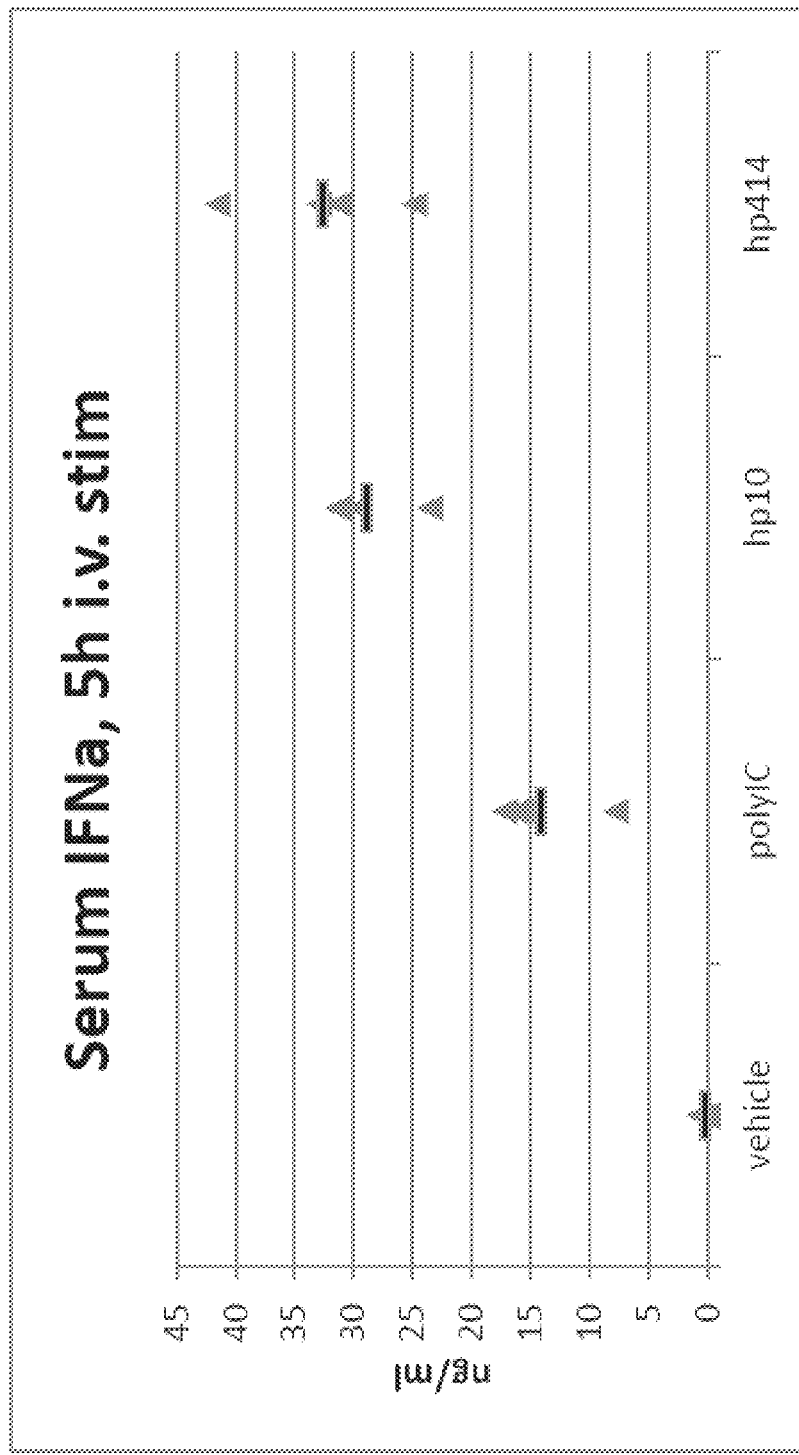
FIG. 1 is a graph depicting the results of a representative experiment depicting serum Interferon alpha levels after treatment with short hairpin RNAs: Mice were injected in the tail vein with jetPEI/RNA complex (i.v.), and serum was collected at 5 hours post-injection. The dose used per mouse was as follows: polyIC=25 ug, hp10=640 uM (25.15 ug), hp414=640 uM (33.4 ug). Four mice were used for each condition. The results indicate that very high levels of IFNalpha are induced by shRNAs and polyIC, and not by the vehicle control. Notably, the shRNAs induce more IFNalpha than polyIC. Note that hp10 is a 5'-triphosphorylated 10 base-pair duplex with a UUCG tetraloop at one end (5'-ppp10L) and hp14 is a 5'-triphosphorylated 14 base pair duplex with a UUCG tetraloop at one end. The polyIC is low molecular weight poly IC.

The present disclosure provides a nucleic acid molecule that can activate the interferon response of one or more pattern recognition receptors (PRRs). In certain embodiments, the disclosure provides compositions and methods for inducing the interferon response of one or more PRRs. For example, the compositions and methods described herein may activate any PRR including, but not limited to, the RIG-I like receptor (RLR) class of PRRs, which include RIG-I, MDA5, and LGP2; NOD-like receptors (NLRs), C-type lectin receptors (CLRs), and toll-like receptors (TLRs). In certain embodiments, the disclosure provides a nucleic acid molecule. Exemplary nucleic acids for use in this disclosure include ribonucleic acids (RNA), deoxyribonucleic acids (DNAs), peptide nucleic acids (PNAs), threose nucleic acids (TNAs), glycol nucleic acids (GNAs), locked nucleic acids (LNAs) or a hybrid thereof. In certain embodiments, the nucleic acid is a ribonucleic acid (RNA).

As described herein, the nucleic acid molecule of the disclosure is not dependent on a particular nucleotide sequence. Rather, any nucleotide sequence may be used, provided that the sequence has the ability to form the structure of a nucleic acid molecule described herein.

In certain embodiments, the nucleic acid molecule of the disclosure comprises a double stranded region. For example, in one embodiment, the nucleic acid molecule is a double stranded duplex. In certain embodiments, the nucleic acid molecule of the disclosure is a single strand wherein a first region of the molecule hybridizes with a second region of the molecule to form a duplex. In certain instances, the hairpin structure of the nucleic acid molecule may improve the stability of the duplex.

In certain embodiments, the nucleic acid molecule comprises a blunt end.

In certain embodiments, the nucleic acid molecule comprises a 5'-triphosphate or a 5'-diphosphate. In certain embodiments, the nucleic acid molecule comprises one or more 5'-triphosphate or one or more 5'-diphosphates. In certain embodiments, the nucleic acid molecule comprises one or more 5'-triphosphates. In certain embodiments, the nucleic acid molecule comprises one or more 5'-diphosphates.

In certain instances, the presence of one or more 5'-triphosphate or 5'-diphosphate may improve the binding affinity of the nucleic acid molecule.

In certain embodiments, the nucleic acid molecule has at least one 3'-overhang. In other embodiments, the 3'-overhang comprises a non-base pairing nucleotide. In yet other embodiments, the 3'-overhang comprises two non-base pairing nucleotides. In yet other embodiments, the 3'-overhang comprises three non-base pairing nucleotides. In yet other embodiments, the 3'-overhang comprises four, five, six, seven, eight, nine, ten, or more than ten non-base pairing nucleotides.

In certain embodiments, the nucleic acid molecule has at least one 5'-overhang. In other embodiments, the intramolecular structure produces a 5'-overhang. In yet other embodiments, the 5'-overhang comprises a non-base pairing nucleotide. In yet other embodiments, the 5'-overhang comprises two non-base pairing nucleotides. In yet other embodiments, the 5'-overhang comprises three non-base pairing nucleotides. In yet other embodiments, the 5'-overhang comprises four, five, six, seven, eight, nine, ten, or more than ten non-base pairing nucleotides.

In certain embodiments, nuclease resistance of the nucleic acid molecule can be enhanced with backbone modifications (e.g., phosphorothioates) and 5'-terminal modifications and/or 3'-terminal modifications.

In certain embodiments, the nucleic acid molecule can be labelled with one or more tracers, such as fluorophores, isotopes, and the like, which are readily incorporated in the terminal loop by solid-phase synthesis.

In certain embodiments, the nucleic acid molecule can be delivered in vivo using delivery vehicles that improve their stability and/or targeting. In other embodiments, the nucleic acid molecule is delivered to the site of the tumor and/or infection. In yet other embodiments, the nucleic acid molecule is delivered systemically.

In certain embodiments, the disclosure provides a nucleic acid molecule which is capable of activating a PRR and inducing an IFN response in cells expressing a PRR. In certain embodiments, the nucleic acid molecule of the present disclosure has a double-stranded section of less than 19 base pairs. In certain embodiments, the nucleic acid molecule comprises at least one 5'-triphosphate or at least one 5'-diphosphate. In certain embodiments, the nucleic acid molecule comprises at least one blunt end.

The present disclosure encompasses the use of the nucleic acid molecule to prevent and/or treat and/or ameliorate any disease, disorder, or condition in which inducing IFN production would be beneficial. For example, increased IFN production, by way of the nucleic acid molecule of the disclosure, may be beneficial to prevent, ameliorate, and/or treat a wide variety of disorders, including, but not limited to, bacterial infection, viral infection, parasitic infection, cancer, autoimmune diseases, respiratory disorders, and the like.

In certain embodiments, the disclosure provides a composition and method for the prevention, amelioration, and/or treatment of a viral infection, including, but not limited to, influenza, hepatitis, human papillomavirus, HIV, and the like. In certain embodiments, the disclosure provides a composition and method for the treatment, amelioration, and/or prevention of a cancer, including, but not limited to, hematological malignancies including various leukemias and lymphomas, carcinomas, blastomas, and sarcomas. In certain embodiments, the disclosure provides a composition and method for the treatment, amelioration, and/or prevention of an autoimmune disease, including but not limited to multiple sclerosis, psoriasis, arthritis, dermatitis, diabetes, lupus, colitis, Aicardi-Goutieres syndrome (AGS), and the like.

In certain embodiments, the disclosure provides a composition and method for preventing, ameliorating, and/or treating a respiratory disorder, including, acute lung injury (ALI), acute respiratory distress syndrome (ARDS), asthma, chronic obstructive pulmonary disease (COPD), obstructive sleep apnea (OSA), idiopathic pulmonary fibrosis (IPF), tuberculosis, pulmonary hypertension, pleural effusion, and/or lung cancer.

As demonstrated herein, the antiviral capacity of a RIG-I agonist, a representative stem-loop RNA molecule, was evaluated in viral control, disease prevention, post-infection therapy, and cross-variant protection in mouse models of SARS-CoV-2 infection. A single dose of the RIG-I agonist prevented viral replication in the lower respiratory tract and development of severe disease in a type I interferon (IFN-I) dependent manner. The RIG-I agonist demonstrated remarkable protective capacity against lethal SARS-CoV-2 infection when used prophylactically and retained considerable efficacy as a therapeutic agent. In immunodeficient mice carrying chronic SARS-CoV-2 infection, the RIG-I agonist elicited near-sterilizing innate immunity by inducing IFN-I responses in the absence of the adaptive immune system. In the context of infection with variants of concern (VOC), the RIG-I agonist conferred broad protection and uncovered an IFN-I resistance gradient across emerging VOC. These findings demonstrate the therapeutic potential of a RIG-I agonist as a host-directed, broad-spectrum antiviral for early post-exposure treatment and for treatment of chronically infected immunosuppressed patients.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are described.

As used herein, each of the following terms has the meaning associated with it in this section.

The articles “a” and “an” are used herein to refer to one or to more than one (i.e., to at least one) of the grammatical object of the article. By way of example, “an element” means one element or more than one element.

“About” as used herein when referring to a measurable value such as an amount, a temporal duration, and the like, is meant to encompass variations of 20% or ±10%, more preferably ±5%, even more preferably 10%, and still more preferably ±0.1% from the specified value, as such variations are appropriate to perform the disclosed methods.

The term “airway inflammation”, as used herein, means a disease or condition related to inflammation on airway of subject. The airway inflammation may be caused or accompanied by allergy(ies), asthma, impeded respiration, cystic fibrosis (CF), chronic obstructive pulmonary diseases (COPD), allergic rhinitis (AR), acute respiratory distress syndrome (ARDS), microbial or viral infections, pulmonary hypertension, lung inflammation, bronchitis, cancer, airway obstruction, bronchoconstriction, and the like.

The term “autoimmune disease” as used herein is defined as a disorder that results from an autoimmune response. An autoimmune disease is the result of an inappropriate and excessive response to a self-antigen. Examples of autoimmune diseases include but are not limited to, Addision’s disease, alopecia greata, ankylosing spondylitis, autoimmune hepatitis, autoimmune parotitis, Crohn’s disease, diabetes (Type I), dystrophic epidermolysis bullosa, epididymitis, glomerulonephritis, Graves’ disease, Guillain-Barr syndrome, Hashimoto’s disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren’s syndrome, spondyloarthropathies, thyroiditis, vasculitis, vitiligo, myxedema, pernicious anemia, ulcerative colitis, among others.

The term “cancer” as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "chronic obstructive pulmonary disease," or COPD, is used herein to refer to two lung diseases, chronic bronchitis and emphysema, that are characterized by obstruction to airflow that interferes with normal breathing. Both of these conditions frequently co-exist.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "COVID" or "COVID-19" refers to the Coronavirus disease 2019, a contagious disease caused by severe acute respiratory syndrome coronavirus 2 (SARS-CoV-2).

The term "emphysema" is a major subset of the clinical entity known as COPD and is characterized by specific pathological changes in lung tissue over time. One hallmark of emphysema is the gradual, progressive, and irreversible destruction of the distal lung parenchyma leading to the destruction alveoli. Alveolar destruction leads to enlarged airspaces in the lung and consequently a reduced ability to transfer oxygen to the bloodstream. Emphysema is also characterized by a loss of elasticity in the lung making it difficult to maintain open airways. Both of these changes produce the clinical sequelae of emphysema comprising shortness of breath and difficulty exhaling, respectively.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "fragment," as applied to a nucleic acid, refers to a subsequence of a larger nucleic acid. A "fragment" of a nucleic acid can be at least about 5 nucleotides in length; for example, at least about 10 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

"Homologous, homology" or "identical, identity" as used herein, refer to comparisons among amino acid and nucleic acid sequences. When referring to nucleic acid molecules, "homology," "identity," or "percent identical" refers to the percent of the nucleotides of the subject nucleic acid sequence that have been matched to identical nucleotides by a sequence analysis program. Homology can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the ExPaSy is used to align sequence fragments of genomic DNA sequences. However, equivalent alignment assessments can be obtained through the use of any standard alignment software.

As used herein, "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5' ATTGCC 3' and 5' TATGGC 3' share 50% homology.

"Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

The term "hybridization" refers to the process in which two single-stranded nucleic acids bind non-covalently to form a double-stranded nucleic acid; triple-stranded hybridization is also theoretically possible. Complementary sequences in the nucleic acids pair with each other to form a double helix. The resulting double-stranded nucleic acid is a "hybrid." Hybridization may be between, for example, two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

The stability of a hybrid depends on a variety of factors including the length of complementarity, the presence of mismatches within the complementary region, the temperature and the concentration of salt in the reaction. Hybridizations are usually performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) or 100 mM MES, 1 M Na, 20 mM EDTA, 0.01% Tween-20 and a temperature of 25-50° C. are suitable for allele-specific probe hybridizations. In a particularly preferred embodiment, hybridizations are performed at 40-50° C. Acetylated BSA and herring sperm DNA may be added to hybridization reactions. Hybridization conditions suitable for microarrays are described in the Gene Expression Technical Manual and the GeneChip Mapping Assay Manual available from Affymetrix (Santa Clara, Calif.).

A first oligonucleotide anneals with a second oligonucleotide with "high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g. Sambrook et al., 2012, Molecular Cloning: A Laboratory Manual, Cold Spring Harbor Laboratory Press, Cold Spring Harbor, N.Y.).

As used herein, an "instructional material" includes a publication, a recording, a diagram, or any other medium of expression which can be used to communicate the usefulness of a compound, composition, vector, or delivery system of the disclosure in the kit for effecting alleviation of the various diseases or disorders recited herein. Optionally, or alternately, the instructional material can describe one or more methods of alleviating the diseases or disorders in a cell or a tissue of a mammal. The instructional material of the kit of the disclosure can, for example, be affixed to a container which contains the identified compound, composition, vector, or delivery system of the disclosure or be shipped together with a container which contains the identified compound, composition, vector, or delivery system. Alternatively, the instructional material can be shipped separately from the container with the intention that the instructional material and the compound be used cooperatively by the recipient.

As used herein, "isolate" refers to a nucleic acid obtained from an individual, or from a sample obtained from an individual. The nucleic acid may be analyzed at any time after it is obtained (e.g., before or after laboratory culture, before or after amplification.)

The term "label" as used herein refers to a luminescent label, a light scattering label or a radioactive label. Fluorescent labels include, but are not limited to, the commercially available fluorescein phosphoramidites such as Fluoreprime (Pharmacia), Fluoredite (Millipore) and FAM (ABI). See U.S. Pat. No. 6,287,778.

As used herein, the term "long COVID," which is also known as "Post-Acute Sequelae of SARS-CoV-2 infection (PASC)," "chronic COVID syndrome (CCS)" and "long-haul COVID," is the condition characterized by long-term sequelae-persisting after the typical convalescence period— of coronavirus disease 2019 (COVID-19). Persistent symptoms include, but are not limited to, fatigue, headaches, shortness of breath, anosmia (loss of smell), muscle weakness, low fever, and cognitive dysfunction (brain fog). Studies suggest that approximately 10% of people who tested positive for SARS-CoV-2 experienced one or more symptoms for longer than 12 weeks. Anyone infected with SARS-CoV-2 can suffer from long COVID after the infection is considered to have ended, including young, healthy people, and even if the initial disease was mild.

The term "mismatch," "mismatch control" or "mismatch probe" refers to a nucleic acid whose sequence is not perfectly complementary to a particular target sequence. The mismatch may comprise one or more bases. As used herein, the term "nucleic acid" refers to both naturally-occurring molecules such as DNA and RNA, but also various derivatives and analogs. Generally, the probes, hairpin linkers, and target polynucleotides of the present teachings are nucleic acids, and typically comprise DNA. Additional derivatives and analogs can be employed as will be appreciated by one having ordinary skill in the art.

The term "nucleotide base," as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6 delta 2-isopentenyladenine (6iA), N6-delta 2-isopentenyl-2-methylthioadenine (2 ms6iA), N2-dimethylguanine (dmG), 7methylguanine (7 mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, 06-methylguanine, N6-methyladenine, 04-methylthymine, 5,6-dihydrothymine, 5,6-dihydrouracil, pyrazolo[3,4-D]pyrimidines (see, e.g., U.S. Pat. Nos. 6,143, 877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "overhang," as used herein, refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3'-end of the duplex is referred to as an overhang.

The term "pattern recognition receptor," abbreviated as PRR, as used herein refers to a family of proteins that typically recognize pathogen-associated molecular patterns. PRRs may include members of the RIG-I like receptor (RLR) family, NOD-like receptor (NLRs) family, C-type lectin receptor (CLRs) family, or toll-like receptor (TLRs) family. In certain embodiments of the present disclosure, the nucleic acid molecule described herein binds to a PRR, thereby resulting in an interferon response. It should be understood that a PRR includes any PRR fragment, variant, splice variant, mutant, or the like. In certain embodiments, the PRR is RIG-I.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

Conventional notation is used herein to describe polynucleotide sequences: the left-hand end of a single-stranded polynucleotide sequence is the 5'-end. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences." In the sequences described herein: A=adenine, G=guanine, T=thymine, C=cytosine, U=uracil, H=A, C or T/U, R=A or G, M=A or C, K=G or T/U, S=G or C, Y=C or T/U, W=A or T/U, B=G or C or T/U, D=A or G, or T/U, V=A or G or C, N=A or G or C or T/U.

The skilled artisan will understand that all nucleic acid sequences set forth herein throughout in their forward orientation, are also useful in the compositions and methods of the disclosure in their reverse orientation, as well as in their forward and reverse complementary orientation, and are described herein as well as if they were explicitly set forth herein.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, e.g., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with a detectable label, e.g., chromogenic, radioactive, or fluorescent moieties and used as detectable moieties. Examples of fluorescent moieties include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Other detectable moieties include digoxigenin and biotin.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes, so long as it does not interfere with hybridization. Thus, probes may be peptide nucleic acids in which the constituent bases are joined by peptide bonds rather than phosphodiester linkages. The term "match," "perfect match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe."

The term "respiratory diseases", as used herein, means diseases or conditions related to, the respiratory system. Examples include, but not limited to, asthma, chronic obstructive pulmonary disease (COPD), airway inflammation, allergy(ies), impeded respiration, cystic fibrosis (CF), allergic rhinitis (AR), acute respiratory distress syndrome (ARDS), lung cancer, pulmonary hypertension, lung inflammation, bronchitis, airway obstruction, bronchoconstriction, microbial infection, and viral infection, such as SARS. Other respiratory diseases referred to herein include dyspnea, emphysema, wheezing, pulmonary fibrosis, hyper-responsive airways, increased adenosine or adenosine receptor levels, particularly those associated with infectious diseases, surfactant depletion, pulmonary vasoconstriction, impeded respiration, infantile respiratory distress syndrome (infantile RDS), allergic rhinitis, and the like.

The term "ribonucleotide" and the phrase "ribonucleic acid" (RNA), as used herein, refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

The term "target" as used herein refers to a molecule that has an affinity for a given molecule. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this disclosure include, but are not restricted to, proteins, peptides, oligonucleotides and nucleic acids.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present disclosure provides a nucleic acid molecule, for example a short duplex nucleic acid molecule, which is capable of activating one or more PRRs and inducing an IFN response in cells expressing a PRR. In certain embodiments, the nucleic acid molecule of the present disclosure comprises a double-stranded section of no more than 19 base pairs, and at least one blunt end. In certain embodiments, the nucleic acid molecule comprises a 5'-triphosphate or a 5'-diphosphate. In certain embodiments, the disclosure further provides the use of the nucleic acid molecule of the disclosure for inducing an IFN response in vitro and/or in vivo. In certain embodiments, the nucleic acid molecule of the disclosure binds to RIG-I, or other PRRs, which in turn leads to increased IFN production.

Accordingly, the present disclosure provides the use of the nucleic acid molecule of the disclosure for preventing, ameliorating, and/or treating diseases or conditions in which inducing IFN production would be beneficial, such as infections, tumors/cancers, inflammatory diseases, and disorders, and/or immune disorders.

In certain embodiments, the nucleic acid of the disclosure comprises intramolecular nucleotide base pairing (i.e., hairpin). Therefore, in certain aspects, the nucleic acid molecule of the disclosure is sometimes referred herein as a short hairpin nucleic acid molecule.

The present disclosure encompasses compositions and method for inducing an interferon response produced by any PRR, including but not limited to members of the RIG-I like receptor (RLR) family; NOD-like receptor (NLRs) family, C-type lectin receptor (CLRs) family, and toll-like receptor (TLRs) family. Thus, while in certain instances, the present disclosure is exemplified herein through stimulation of RIG-I, a skilled artisan would recognize that the present disclosure is equally applicable to the stimulation of any PRR known in the art, or discovered in the future.

Compositions

In certain embodiments, the disclosure provides a nucleic acid molecule which is capable of inducing an IFN response in cells expressing a PRR. In certain embodiments, the nucleic acid molecule of the present disclosure comprises a double-stranded section of no more than 19 base pairs and at least one blunt end. In certain embodiments, the nucleic acid molecule comprises a 5'-triphosphate or a 5'-diphosphate. In certain embodiments, the nucleic acid molecule comprises one or more 5'-triphosphates and/or one or more 5'-diphosphates. In certain embodiments, the nucleic acid molecule comprises one or more 5'-triphosphates. In certain embodiments, the nucleic acid molecule comprises one or more 5'-diphosphates. In embodiments, the nucleic acid molecule comprises the following structure:

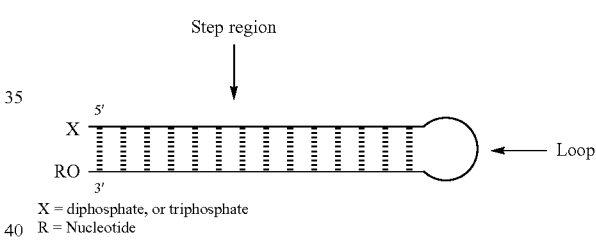

X = diphosphate, or triphosphate
R = Nucleotide

In certain embodiments, the nucleic acid molecule of the present disclosure has a double-stranded section of less than 19 base pairs, in one aspect less than 18 base pairs, in one aspect less than 16 base pairs, in one aspect less than 14 base pairs, in one aspect less than 12 base pairs, in one aspect less than 10 base pairs, in one aspect less than 8 base pairs, in one aspect less than 6 base pairs, in one aspect less than 4 base pairs. In certain embodiments, the nucleic acid molecule of the present disclosure has a double-stranded section of 20 base pairs, 19 base pairs, 18 base pairs, 17 base pairs, 16 base pairs, 15 base pairs, 14 base pairs, 13 base pairs, 12 base pairs, 11 base pairs, 10 base pairs, 9 base pairs, 8 base pairs, 7 base pairs, or 6 base pairs. In certain embodiments, the double-stranded section comprises one or more mispaired bases. That is, Watson-Crick base pairing is not required at each and every nucleotide pair. In certain embodiments, the double-stranded section comprises about 4-19 base pairs.

In some instances, the nucleic acid molecule can be of any sequence and comprises a hairpin structure and a blunt end, wherein the hairpin comprises a double-stranded section of less than 19 base pairs.

In certain embodiments, the short hairpin nucleic acid molecule comprises: an antisense sequence and a sense sequence, wherein the sense sequence is substantially complementary to the antisense sequence; and a loop region or a linker connecting the antisense and sense sequences.

In certain aspects, the present disclosure includes a polynucleotide comprising a unimolecular RNA, such as a short hairpin RNA. The short hairpin RNA can be a unimolecular RNA that includes a sense sequence, a loop region or a linker, and an antisense sequence which together form a hairpin loop structure. Preferably, the antisense and sense sequences are substantially complementary to one other (about 80% complementary or more), where in certain embodiments the antisense and sense sequences are 100% complementary to each other. In certain embodiments, antisense and sense sequences each comprises 20 base pairs, 19 base pairs, 18 base pairs, 17 base pairs, 16 base pairs, 15 base pairs, 14 base pairs, 13 base pairs, 12 base pairs, 11 base pairs, 10 base pairs, 9 base pairs, 8 base pairs, 7 base pairs, or 6 base pairs. Additionally, the antisense and sense sequences within a unimolecular RNA of the disclosure can be the same length or differ in length. The loop can be any length, for example a length being 0, 1 or more, 2 or more, 4 or more, 5 or more, 8 or more, 10 or more, 15 or more, 20 or more, 40 or more, or 100 or more nucleotides in length.

In certain aspects, the linker is free of a nucleoside, nucleotide, deoxynucleoside, or deoxynucleotide, or any surrogates or modifications thereof. In certain embodiments, the linker is free of a phosphate backbone, or any surrogates or modifications thereof.

Any linker known in the art is contemplated herein. Non-limiting examples of linkers include ethylene glycols (—CH$_2$CH$_2$O), peptides, peptide nucleic acids (PNAs), alkylene chains (a divalent alkane-based group), amides, esters, ethers, and so forth, and any combinations thereof.

In certain embodiments, the linker comprises at least one ethylene glycol group. In other embodiments, the linker comprises one ethylene glycol group. In yet other embodiments, the linker comprises two ethylene glycol groups. In yet other embodiments, the linker comprises three ethylene glycol groups. In yet other embodiments, the linker comprises four ethylene glycol groups. In yet other embodiments, the linker comprises five ethylene glycol groups. In yet other embodiments, the linker comprises six ethylene glycol groups. In yet other embodiments, the linker comprises seven ethylene glycol groups. In yet other embodiments, the linker comprises eight ethylene glycol groups. In yet other embodiments, the linker comprises nine ethylene glycol groups. In yet other embodiments, the linker comprises ten ethylene glycol groups. In yet other embodiments, the linker comprises more than ten ethylene glycol groups. In yet other embodiments, the linker comprises (OCH$_2$CH$_2$)$_n$, wherein n is an integer ranging from 1 to 10. In yet other embodiments, n is 1. In yet other embodiments, n is 2. In yet other embodiments, n is 3. In yet other embodiments, n is 4. In yet other embodiments, n is 5. In yet other embodiments, n is 6. In yet other embodiments, n is 7. In yet other embodiments, n is 8. In yet other embodiments, n is 9. In yet other embodiments, n is 10.

In certain embodiments, the linker comprises at least one amino acid, at least two amino acids, at least three amino acids, at least four amino acids, at least five amino acids, at least six amino acids, at least seven amino acids, at least eight amino acids, at least nine amino acids, at least ten amino acids, or more than ten amino acids.

In certain embodiments, the linker comprises an alkylene chain, such as but not limited to a $C_1$-$C_{50}$ alkylene chain, which is optionally substituted with at least one substituent selected from the group consisting of $C_1$-$C_6$ alkyl, $C_1$-$C_6$ haloalkyl, $C_1$-$C_6$ alkyl, $C_3$-$C_8$ cycloalkyl, $C_1$-$C_6$ alkoxy, —OH, halo, —NH$_2$, —NH($C_1$-$C_6$ alkyl), —N($C_1$-$C_6$ alkyl)($C_1$-$C_6$ alkyl), —C(=O)OH, —C(=O)O($C_1$-$C_6$ alkyl), and —C(=O)O($C_3$-$C_8$ cycloalkyl), wherein the alkyl or cycloalkyl is optionally substituted with at least one selected from the group consisting of $C_1$-$C_6$ alkyl, $C_1$-$C_6$ haloalkyl, $C_1$-$C_6$ alkyl, $C_3$-$C_8$ cycloalkyl, $C_1$-$C_6$ alkoxy, —OH, halo, —NH$_2$, —NH($C_1$-$C_6$ alkyl), —N($C_1$-$C_6$ alkyl)($C_1$-$C_6$ alkyl), —C(=O)OH, —C(=O)O($C_1$-$C_6$ alkyl), and —C(=O)O($C_3$-$C_8$ cycloalkyl). In other embodiments, the linker is selected from the group consisting of —(CH$_2$)—, —(CH$_2$)$_2$—, —(CH$_2$)$_3$—, —(CH$_2$)$_2$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, and —(CH$_2$)$_{20}$—, each of each is independently optionally substituted as described elsewhere herein.

The nucleic acid molecule of the disclosure comprises nucleic acids from any source. A nucleic acid in the context of the present disclosure includes but is not limited to deoxyribonucleic acid (DNA), ribonucleic acid (RNA), peptide nucleic acid (PNA, threose nucleic acid (TNA), glycol nucleic acid (GNA), locked nucleic acid (LNA) or a hybrid thereof). In certain embodiments, the nucleic acid is a ribonucleic acid (RNA).

DNA and RNA are naturally occurring in organisms, however, they may also exist outside living organisms or may be added to organisms. The nucleic acid may be of any origin, e.g., viral, bacterial, archae-bacterial, fungal, ribosomal, eukaryotic or prokaryotic. It may be nucleic acid from any biological sample and any organism, tissue, cell or sub-cellular compartment. It may be nucleic acid from any organism. The nucleic acid may be pre-treated before quantification, e.g., by isolation, purification or modification. Also artificial or synthetic nucleic acid may be used. The length of the nucleic acids may vary. The nucleic acids may be modified, e.g. may comprise one or more modified nucleobases or modified sugar moieties (e.g., comprising methoxy groups). The backbone of the nucleic acid may comprise one or more peptide bonds as in peptide nucleic acid (PNA). The nucleic acid may comprise a base analog such as non-purine or non-pyrimidine analog or nucleotide analog. It may also comprise additional attachments such as proteins, peptides and/or or amino acids.

In certain embodiments, the nucleic acid molecule of the disclosure is a single stranded oligonucleotide that forms an intramolecular structure, i.e., a hairpin structure.

In certain embodiments, the hairpin nucleic acid molecule forms a blunt end. In certain embodiments, a blunt end refers to, e.g., an RNA duplex where at least one end of the duplex lacks any overhang, e.g., a 3'-dinucleotide overhang, such that both the 5'- and 3'-strand end together, i.e., are flush or as referred to herein, are blunt. The molecules of the disclosure have at least one blunt end. In some instances, the intramolecular structure produces a 3'-overhang. In some instances, the intramolecular structure produces a 5'-overhang.

In certain instances, the short hairpin nucleic acid molecule of the disclosure is an ideal stimulant because of the ability to re-anneal after being unwound, whereas the shorter palindromic duplexes that are not a hairpin would likely lose their ability to stimulate IFN production as soon as the duplex melted. However, the present disclosure is not limited to hairpin structures, as it is demonstrated herein that short double-stranded duplexes demonstrate the ability to bind to a PRR and stimulate an interferon response.

In some instances, the short hairpin nucleic acid molecule of the disclosure is designed that in some conditions, the intramolecular stem structure has reduced stability where the stem structure is unfolded. In this manner, the stem structure can be designed so that the stem structure can be relieved of its intramolecular base pairing and resemble more of a linear molecule.

In accordance with the present disclosure, there are provided predetermined stem oligonucleotide sequences containing stretches of complementary sequences that form the stem structure. In certain embodiments, the stem comprises a double-stranded section that comprise in one aspect less than 19 base pairs, in one aspect less than 18 base pairs, in one aspect less than 16 base pairs, in one aspect less than 14 base pairs, in one aspect less than 12 base pairs, in one aspect less than 10 base pairs, in one aspect less than 8 base pairs, in one aspect less than 6 base pairs, in one aspect less than 4 base pairs, such that these complementary stretches anneal to provide a hairpin structure. In certain embodiments, the double-stranded section comprises one or more base mispairs. That is, the double-stranded section need not comprise Watson-Crick base pairing at each and every base pair in order to produce the hairpin structure.

In certain embodiments, the short hairpin nucleic acid molecule of the disclosure comprising: an antisense sequence and a sense sequence, wherein the sense sequence is substantially complementary to the antisense sequence; and a loop region connecting the antisense and sense sequences.

In certain aspects, the present disclosure includes a polynucleotide comprising a unimolecular RNA, such as a short hairpin RNA. The short hairpin RNA can be a unimolecular RNA that includes a sense sequence, a loop region, and an antisense sequence which together form a hairpin loop structure. Preferably, the antisense and sense sequences are substantially complementary to one other (about 80% complementary or more), where in certain embodiments the antisense and sense sequences are 100% complementary to each other. In certain embodiments, antisense and sense sequences each comprises less than 19 nucleotides in length, e.g., between 18 and 8 nucleotides in length. Additionally, the antisense and sense sequences within a unimolecular RNA of the disclosure can be the same length or differ in length. The loop can be any length, for example a length being 0 or more, 1 or more, 2 or more, 4 or more, 5 or more, 8 or more, 10 or more, 15 or more, 20 or more, 40 or more, or 100 or more nucleotides in length.

Nucleic Acid Modification

The nucleic acid molecules of the present disclosure can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In certain embodiments of the present disclosure the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Modifications can be added to enhance stability, functionality, and/or specificity and to minimize immunostimulatory properties of the short hairpin nucleic acid molecule of the disclosure. For example, the overhangs can be unmodified, or can contain one or more specificity or stabilizing modifications, such as a halogen or O-alkyl modification of the 2' position, or internucleotide modifications such as phosphorothioate modification. The overhangs can be ribonucleic acid, deoxyribonucleic acid, or a combination of ribonucleic acid and deoxyribonucleic acid.

In some instances, the nucleic acid molecule comprises at least one of the following chemical modifications: 2'-H, 2'-O-methyl, or 2'-OH modification of one or more nucleotides; one or more phosphorothioate modifications of the backbone; and a non-nucleotide moiety; wherein the at least one chemical modification confers reduced immunostimulatory activity, increased serum stability, or both, as compared to a corresponding short hairpin nucleic acid molecule not having the chemical modification.

In certain embodiments, the pyrimidine nucleotides comprise 2'-O-methylpyrimidine nucleotides and/or 2'-deoxypyrimidine nucleotides.

In certain embodiments, some or all of the purine nucleotides can comprise 2'-O-methylpurine nucleotides and/or 2'-deoxy-purine nucleotides.

In certain embodiments, the chemical modification is present in nucleotides proximal to the 3'- and/or 5'-ends of the nucleic acid molecule of the disclosure.

In certain embodiments, a nucleic acid molecule of the disclosure can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents.

For increased nuclease resistance the nucleic acid molecules of the disclosure can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In certain embodiments, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In certain embodiments, the nucleic acid molecule includes at least one 2'-O-methyl-modified nucleotide, and in some embodiments, all of the nucleotides of the nucleic acid molecule include a 2'-O-methyl modification.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; amine, 0-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substituents are 2'-methoxyethyl, 2'-OCH3, 2'-O-allyl, 2'-C-allyl, and 2'-fluoro.

One way to increase resistance is to identify cleavage sites and modify such sites to inhibit cleavage. For example, the dinucleotides 5'-UA-3', 5'-UG-3', 5'-CA-3', 5'-UU-3', or 5'-CC-3' can serve as cleavage sites. Enhanced nuclease resistance can therefore be achieved by modifying the 5'-nucleotide, resulting, for example, in at least one 5'-uridine-adenine-3'-(5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The oligonucleotide molecule can include at least 2, at least 3, at least 4 or at least 5 of such dinucleotides. In certain embodiments, all the pyrimidines of a nucleic acid molecule carry a 2'-modification, and the nucleic acid molecule therefore has enhanced resistance to endonucleases.

With respect to phosphorothioate linkages that serve to increase protection against RNase activity, the nucleic acid molecule can include a phosphorothioate at least the first, second, or third internucleotide linkage at the 5'- or 3'-end of the nucleotide sequence. To maximize nuclease resistance, the 2' modifications can be used in combination with one or more phosphate linker modifications (e.g., phosphorothioate).

In certain embodiments, the inclusion of pyranose sugars in the nucleic acid backbone can also decrease endonucleolytic cleavage. The certain embodiments, inclusion of furanose sugars in the nucleic acid backbone can also decrease endonucleolytic cleavage.

In certain embodiments, the 5'-terminus can be blocked with an aminoalkyl group, e.g., a 5'-O-alkylamino substituent. Other 5'-conjugates can inhibit 5'-3' exonucleolytic cleavage. While not being bound by theory, a 5'-conjugate, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 5'-3-exonucleases.

Thus, a nucleic acid molecule can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the oligonucleotide molecule as well, e.g., the ability to interact with a protein, e.g., a transport protein, e.g., serum albumin.

One or more different NRM modifications can be introduced into a nucleic acid molecule or into a sequence of a nucleic acid molecule. An NRM modification can be used more than once in a sequence or in a nucleic acid molecule.

NRM modifications include some which can be placed only at the terminus and others which can go at any position. Some NRM modifications that can inhibit hybridization are preferably used only in terminal regions, and more preferably not at the cleavage site or in the cleavage region of a nucleic acid molecule.

Such modifications can be introduced into the terminal regions, e.g., at the terminal position or with 2, 3, 4, or 5 positions of the terminus, of a sequence which targets or a sequence which does not target a sequence in the subject.

In certain embodiments, a nucleic acid molecule, includes a modification that improves targeting, e.g. a targeting modification described herein. Examples of modifications that target a nucleic acid molecule to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

A nucleic acid molecule can be constructed using chemical synthesis and/or enzymatic ligation reactions using procedures known in the art. For example, a nucleic acid molecule can be chemically synthesized using naturally occurring nucleotides or variously modified nucleotides designed to increase the biological stability of the molecules or to increase the physical stability of the binding between the nucleic acid molecule and target, e.g., phosphorothioate derivatives and acridine substituted nucleotides can be used. Other appropriate nucleic acid modifications are described herein. Alternatively, the nucleic acid molecule can be produced biologically using an expression vector.

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —NH(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a R$_3$SiO— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl, and decalin.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, SO$_3$H, sulfate, phosphate, perfluoroalkyl, perfluoroalkoxy, methylenedioxy, ethylenedioxy, carboxyl, oxo, thioxo, imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

For ease of exposition the term nucleotide or ribonucleotide is sometimes used herein in reference to one or more monomeric subunits of an oligonucleotide agent. It will be understood herein that the usage of the term "ribonucleotide" or "nucleotide" herein can, in the case of a modified RNA or nucleotide surrogate, also refer to a modified nucleotide, or surrogate replacement moiety at one or more positions.

In certain embodiments, the nucleic acid molecule of the disclosure preferably has one or more of the following properties:
(1) a 5'-modification that includes one or more phosphate groups or one or more analogs of a phosphate group;
(2) despite modifications, even to a very large number of bases, bases specifically base pair and form a duplex structure with a double-stranded region;
(3) despite modifications, even to a very large number, or all of the nucleosides, nucleos(t)ides still have "RNA-like" properties, i.e., it will possess the overall structural, chemical and physical properties of an RNA molecule, even though not exclusively, or even partly, of ribonucleotide-based content. For example, all of the nucleotide sugars can contain e.g., 2'OMe and/or 2'fluoro in place of 2' hydroxyl. This deoxyribonucleotide-containing agent can still be expected to exhibit RNA-like properties. While not wishing to be bound by theory, an electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into hydrogen-bonding which is more characteristic of the 2'-OH moiety of a ribonucleotide than the 2'-H moiety of a deoxyribonucleotide. In certain embodiments, the oligonucleotide molecule will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; and/or will have no more than 20, 10, 5, 4, 3, 2, or 1 sugar which is not a $C_{3'}$-endo pucker structure.

2'-modifications with C3'-endo sugar pucker include 2'-OH, 2'-O-Me, 2'-O-methoxyethyl, 2'-O-aminopropyl, 2'-F, 2'-O—CH$_2$—CO—NHMe, 2'-O—CH$_2$—CH$_2$—O—CH$_2$—CH$_2$—N(Me)$_2$, and LNA. In certain embodiments, the 2'-O is connected by a bridge to the 4' carbon.

2'-modifications with a C2'-endo sugar pucker include 2'-H, 2'-Me, 2'-S-Me, 2'-Ethynyl, 2'-ara-F.

Sugar modifications can also include L-sugars and 2'-5'-linked sugars.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (*Nucleic Acids Res.,* 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Examples of all of the above are discussed herein.

As nucleic acids are polymers of subunits or monomers, many of the modifications described below occur at a position which is repeated within a nucleic acid, e.g., a modification of a base, or a phosphate moiety, or a non-linking O of a phosphate moiety. In some cases the modification will occur at all of the subject positions in the nucleic acid but in many, and in fact in most cases it will not. By way of example, a modification may only occur at a 3'- or 5'-terminal position, in a terminal region, e.g., at a position on a terminal nucleotide, or in the last 2, 3, 4, 5, or 10 nucleotides of a strand. The ligand can be attached at the 3'-end, the 5'-end, or at an internal position, or at a combination of these positions. For example, the ligand can be at the 3'-end and the 5'-end; at the 3'-end and at one or more internal positions; at the 5'-end and at one or more internal positions; or at the 3'-end, the 5'-end, and at one or more internal positions. For example, a phosphorothioate modification at a non-linking O position may only occur at one or both termini, or may only occur in a terminal region, e.g., at a position on a terminal nucleotide or in the last 2, 3, 4, 5, or 10 nucleotides of the nucleic acid. The 5'-end can be phosphorylated.

Modifications and nucleotide surrogates are discussed below.

FORMULA 1

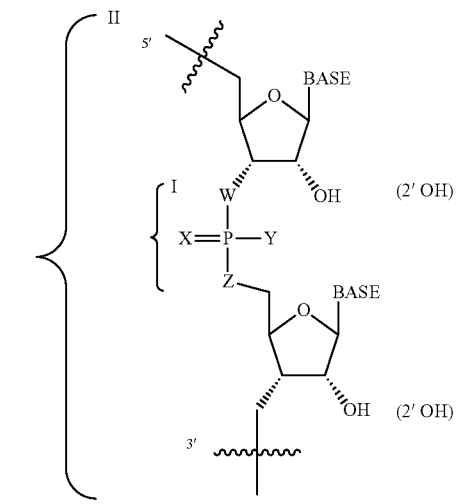

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, for example, can render oligoribonucleotides more stable to nucleases. Unmodified oligoribonucleotides may also be less than optimal in terms of offering tethering points for attaching ligands or other moieties to a nucleic acid agent.

Modified nucleic acids and nucleotide surrogates can include one or more of:
(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein.);
(ii) alteration, e.g., replacement, of a constituent of the ribose sugar, e.g., of the 2' hydroxyl on the ribose sugar, or wholesale replacement of the ribose sugar with a structure other than ribose, e.g., as described herein;
(iii) wholesale replacement of the phosphate moiety (bracket I) with "dephospho" linkers;
(iv) modification or replacement of a naturally occurring base;
(v) replacement or modification of the ribose-phosphate backbone (bracket II);
(vi) modification of the 3'-end or 5'-end of the RNA, e.g., removal, modification or replacement of a terminal phosphate group or conjugation of a moiety, such as a fluorescently labeled moiety, to either the 3'- or 5'-end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid but rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present disclosure are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.
The Phosphate Group
The phosphate group is a negatively charged species. The charge is distributed equally over the two non-linking oxygen atoms (i.e., X and Y in Formula 1 above). However, the phosphate group can be modified by replacing at least one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g., phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is preferred.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5')). Replacement of W with carbon or Z with nitrogen is preferred.

Candidate agents can be evaluated for suitability as described below.
The Sugar Group
A modified RNA can include modification of all or some of the sugar groups of the ribonucleic acid. For example, the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge or ethylene bridge (e.g., 2'-4'-ethylene bridged nucleic acid (ENA)), to the 4' carbon of the same ribose sugar; amino, 0-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity (an SRMS) at one or more sites in the nucleic acid agent.

Candidate modifications can be evaluated as described below.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —$(CH_2)_n$—, —$(CH_2)_n$N—, —$(CH_2)_n$O—, —$(CH_2)_n$S—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Preferred modifications include the addition of a methylphosphonate at the 3'-most terminal linkage; a 3'-C5-aminoalkyl-dT; 3'-cationic group; or another 3'-conjugate to inhibit 3'-5' exonucleolytic degradation.

Terminal modifications useful for modulating activity include modification of the 5'-end with phosphate or phosphate analogs. For example, in certain embodiments, oligonucleotide agents are 5'-phosphorylated or include a phosphoryl analog at the 5'-terminus. Suitable modifications include: 5'-monophosphate ($(HO)_2(O)P$—O-5'); 5'-diphosphate ($(HO)_2(O)P$—O—$P(HO)(O)$—O-5'); 5'-triphosphate ($(HO)_2(O)P$—O—$(HO)(O)P$—O—$P(HO)(O)$—O-5'); 5'-guanosine cap (7-methylated or non-methylated) (7m-G-

O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; $(HO)_2(S)P$—O-5'); 5'-monodithiophosphate (phosphorodithioate; (HO)(HS)(S)P—O-5'), 5'-phosphorothiolate $((HO)_2(O)P$—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates $((HO)_2(O)P$—NH-5', $(HO)(NH_2)(O)P$—O-5'), 5'-alkylphosphonates (R=alkyl=methyl, ethyl, isopropyl, propyl, etc., e.g. RP(OH)(O)—O-5'-, $(OH)_2(O)P$-5'-$CH_2$—), 5'-alkyletherphosphonates (R=alkylether=methoxymethyl ($MeOCH_2$—), ethoxymethyl, etc., e.g. RP(OH)(O)—O-5'-).

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include cholesterol. Terminal modifications can also be useful for cross-linking anantagomir to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Candidate modifications can be evaluated as described below.

Evaluation of Candidate Nucleic Acid Agents

One can evaluate a candidate nucleic acid molecule, for a selected property by exposing the molecule or modified molecule and a control molecule to the appropriate conditions and evaluating for the presence of the selected property. For example, resistance to a degradent can be evaluated as follows. A candidate modified nucleic acid molecule can be exposed to degradative conditions, e.g., exposed to a milieu, which includes a degradative agent, e.g., a nuclease. For example, one can use a biological sample, e.g., one that is similar to a milieu, which might be encountered, in therapeutic use, e.g., blood or a cellular fraction, e.g., a cell-free homogenate or disrupted cells. The candidate and control can then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified nucleic acid molecules can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to activate PRR activity. For example, a cell, e.g., a mammalian cell, such as a mouse or human cell, can be co-transfected with a plasmid encoding a PRR, and a candidate nucleic acid molecule. In certain embodiments, the candidate oligonucleotide molecule can be assayed for its ability to activate RIG-I ATPase activity and/or IFN production, as described elsewhere herein.

RNA may be produced enzymatically or by partial/total organic synthesis, any modified ribonucleotide can be introduced by in vitro enzymatic or organic synthesis. In certain embodiments, the nucleic acid molecule of the disclosure is prepared chemically. Methods of synthesizing RNA molecules are known in the art, in particular, the chemical synthesis methods as described in Verma and Eckstein (1998) Annul Rev. Biochem. 67:99-134.

In certain embodiments, the nucleic acid molecule is synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA molecule. Activity of the RNA molecule may be induced by specific transcription in an organ, tissue, or cell type; stimulation of an environmental condition (e.g., infection, stress, temperature, chemical inducers); and/or engineering transcription at a developmental stage or age.

Methods

The disclosure includes methods of introducing nucleic acids, vectors, and host cells to a subject. Physical methods of introducing nucleic acids include injection of a solution containing the nucleic acid molecule, bombardment by particles covered by the nucleic acid molecule, soaking the cell or organism in a solution of the nucleic acid molecule, or electroporation of cell membranes in the presence of the nucleic acid molecule. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, stabilize the duplex, or other-wise increase activity of the nucleic acid molecule.

Methods of introducing nucleic acids into a cell are known in the art. The nucleic acid molecule of the disclosure can be readily introduced into a host cell, e.g., mammalian, bacterial, yeast, or insect cell by any method in the art. For example, the nucleic acid molecule can be transferred into a host cell by physical, chemical, or biological means.

Physical methods for introducing a nucleic acid into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a nucleic acid into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In certain instances, the nucleic acid is delivered via a polymeric delivery vehicle. For example, the nucleic acid molecule may be complexed with a polymer based micelle, capsule, microparticle, nanoparticle, or the like. The complex may then be contacted to a cell in vivo, in vitro, or ex vivo, thereby introducing the nucleic acid molecule to the cell. Exemplary polymeric delivery systems are well known in the art (see for example U.S. Pat. No. 6,013,240). Polymeric delivery reagents are commercially available, including exemplary reagents obtainable from Polyplus-transfection Inc (New York, N.Y.).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce the nucleic acid molecule into a host cell or otherwise expose a cell to the molecule of the present disclosure, in order to confirm the presence of the nucleic acid in the host cell, a variety of assays may be performed. Such assays include, for example, "molecular biological" assays well known to those of skill in the art, such as Southern and Northern blotting, RT-PCR and PCR.

The nucleic acid molecule of the disclosure may be directly introduced into the cell (i.e., intracellularly); or introduced extracellularly into a cavity, interstitial space, into the circulation of an organism, introduced orally, or may be introduced by bathing a cell or organism in a solution containing the nucleic acid molecule. Vascular or extravascular circulation, the blood or lymph system, and the cerebrospinal fluid are sites where the nucleic acid molecule may be introduced.

Alternatively, vectors, e.g., transgenes encoding the nucleic acid molecule of the disclosure can be engineered into a host cell or transgenic animal using art recognized techniques.

The present disclosure provides a method of inducing an IFN response in a cell. For example, in certain embodiments, the method induces a type I IFN response. Type I IFNs include, for example IFN-α, IFN-β, IFN-κ, IFN-δ, IFN-ε, IFN-τ, IFN-ω, and IFN-ζ.

The present application provides the in vitro use of the nucleic acid molecule of the disclosure. In particular, the present application provides the use of at least one nucleic acid molecule for inducing an IFN response, including for example a type I IFN response, in vitro. The present application also provides the use of at least one nucleic acid molecule for inducing apoptosis of a tumor cell in vitro.

The present disclosure provides an in vitro method for stimulating an IFN response, including for example a type I IFN response in a cell comprising contacting a cell with at least one nucleic acid molecule of the disclosure.

The cells may express a PRR endogenously and/or exogenously from an exogenous nucleic acid (RNA or DNA). The exogenous DNA may be a plasmid DNA, a viral vector, or a portion thereof. The exogenous DNA may be integrated into the genome of the cell or may exist extra-chromosomally. The cells include, but are not limited to, primary immune cells, primary non-immune cells, and cell lines. Immune cells include, but are not limited to, peripheral blood mononuclear cells (PBMC), plasmacytoid dendritic cells (PDC), myeloid dendritic cells (MDC), macrophages, monocytes, B cells, natural killer cells, granulocytes, CD4+ T cells, CD8+ T cells, and NKT cells. Non-immune cells include, but are not limited to, fibroblasts, endothelial cells, epithelial cells, and tumor cells. Cell lines may be derived from immune cells or non-immune cells.

The present disclosure provides an in vitro method for inducing apoptosis of a tumor cell, comprising contacting a tumor cell with at least one nucleic acid molecule of the disclosure. The tumor cell may be a primary tumor cell freshly isolated from a vertebrate animal having a tumor or a tumor cell line.

In certain embodiments, the present disclosure provides for both prophylactic and therapeutic methods of inducing an IFN response a patient. It is understood that "treatment" or "treating" as used herein, is defined as the application or administration of a therapeutic agent (e.g., a nucleic acid molecule) to a patient, or application or administration of a therapeutic agent to an isolated tissue or cell line from a patient, who has a disease or disorder, and/or a symptom of disease or disorder, with the purpose to cure, heal, alleviate, relieve, alter, remedy, ameliorate, improve, and/or affect the disease or disorder, and/or the symptoms of the disease or disorder.

In certain embodiments, the present application provides the in vivo use of the nucleic acid molecule of the disclosure. In certain embodiments, the present application provides at least one nucleic acid molecule of the disclosure for inducing an IFN response, including for example a type I IFN response, in a vertebrate animal, in particular, a mammal. The present application further provides at least one nucleic acid molecule of the disclosure for inducing apoptosis of a tumor cell in a vertebrate animal, in particular, a mammal. The present application additionally provides at least one nucleic acid molecule of the disclosure for preventing and/or treating a disease and/or disorder in a vertebrate animal, in particular, a mammal, in medical and/or veterinary practice. The disclosure also provides at least one nucleic acid molecule of the disclosure for use as a vaccine adjuvant.

In certain embodiments, the composition and method of the disclosure are used as a research tool. For example, the nucleic acid molecule may be used in vitro or in vivo, to evaluate the effects of increased PRR activity and/or increased IFN production.

Furthermore, the present application provides the use of at least one nucleic acid molecule of the disclosure for the preparation of a pharmaceutical composition for inducing an IFN response, including for example a type I IFN response in a vertebrate animal, in particular, a mammal. The present application further provides the use of at least one nucleic acid molecule of the disclosure for the preparation of a pharmaceutical composition for inducing apoptosis of a tumor cell in a vertebrate animal, in particular, a mammal. The present application additionally provides the use of at least one nucleic acid molecule of the disclosure for the preparation of a pharmaceutical composition for preventing and/or treating a disease and/or disorder in a vertebrate animal, in particular, a mammal, in medical and/or veterinary practice.

The present disclosure encompasses the use of the nucleic acid molecule to prevent, ameliorate, and/or treat any disease, disorder, or condition in which inducing IFN production would be beneficial. For example, increased IFN production, by way of the nucleic acid molecule of the disclosure, may be beneficial to prevent or treat a wide variety of disorders, including, but not limited to, bacterial infection, viral infection, parasitic infection, cancer, immune disorders, respiratory disorders, and the like. Infections include, but are not limited to, viral infections, bacterial infections, anthrax, parasitic infections, fungal infections and prion infection.

The present disclosure provides a method for treating, ameliorating, and/or preventing a viral infection in a subject. The present disclosure provides a method for treating, ameliorating, and/or preventing a viral infection in a tumor-bearing subject. The present disclosure provides a method for treating, ameliorating, and/or preventing a viral infection in an immunocompromised and/or immunodeficient subject. In certain embodiments, the method comprises administering to the subject a therapeutically effective amount of a nucleic acid molecule as described herein. In certain embodiments, the molecule comprises a double-stranded section of less than 19 base pairs and at least one blunt end. In certain embodiments, the administering induces type I interferon production in at least one cell of the subject.

In certain embodiments, the administering takes place before the subject is exposed to the virus. In certain embodiments, the administering takes place at, and/or less than, about 7 days, 6.5 days, 6 days, 5.5 days, 5 days, 4.5 days, 4 days, 3.5 days, 3 days, 2.5 days, 2 days, 1.5 days, 1 day, and/or 0.5 days before the subject is exposed to the virus. In certain embodiments, the administering takes place at, and/or less than, about 100 h, 95 h, 90 h, 85 h, 80 h, 75 h, 70 h, 65 h, 60 h, 55 h, 50 h, 48 h, 46 h, 44 h, 42 h, 40 h, 38 h, 36 h, 34 h, 32 h, 30 h, 29 h, 28 h, 27 h, 26 h, 25 h, 24 h, 23 h, 22 h, 21 h, 20 h, 19 h, 18 h, 17 h, 16 h, 15 h, 14 h, 13 h, 12 h, 11 h, 10 h, 9 h, 8 h, 7 h, 6 h, 5 h, 4 h, 3 h, 2 h, 1.8 h, 1.6 h, 1.4 h, 1.2 h, 1 h, 0.9 h, 0.8 h, 0.7 h, 0.6 h, 0.5 h, 0.4 h, 0.3 h, 0.2 h, and/or 0.1 h before the subject is exposed to the virus. In certain embodiments, the administering takes place after the subject is exposed to the virus. In certain embodiments, the administering takes place at, and/or less than, about 7 days, 6.5 days, 6 days, 5.5 days, 5 days, 4.5 days, 4 days, 3.5 days, 3 days, 2.5 days, 2 days, 1.5 days, 1 day, and/or 0.5 days after the subject is exposed to the virus. In certain embodiments, the administering takes place at, and/or less than, about 100 h, 95 h, 90 h, 85 h, 80 h, 75 h, 70 h, 65 h, 60 h, 55 h, 50 h, 48 h, 46 h, 44 h, 42 h, 40 h, 38 h, 36 h, 34 h, 32 h, 30 h, 29 h, 28 h, 27 h, 26 h, 25 h, 24 h, 23 h, 22 h, 21 h, 20 h, 19 h, 18 h, 17 h, 16 h, 15 h, 14 h, 13 h, 12 h, 11 h, 10 h, 9 h, 8 h, 7 h, 6 h, 5 h, 4 h, 3 h, 2 h, 1.8 h, 1.6 h, 1.4 h, 1.2 h, 1 h, 0.9 h, 0.8 h, 0.7 h, 0.6 h, 0.5 h, 0.4 h, 0.3 h, 0.2 h, and/or 0.1 h after the subject is exposed to the virus.

In certain embodiments, the administering reduces recovery time for, eliminates, and/or minimizes at least one complication from the viral infection. In certain embodiments, the complication comprises weight loss, fever, cough, fatigue, muscle and/or body ache, nausea, vomiting, diarrhea, shortness of breath, loss of smell and/or taste, acute respiratory distress syndrome (ARDS), low blood oxygen levels, pneumonia, multi-organ failure, septic shock, heart failure, arrhythmias, heart inflammation, blood clots, and/or death.

In certain embodiments, the virus comprises at least one of Crimean-Congo haemorrhagic fever virus, Eastern Equine Encephalitis virus, Ebola virus, Lassa fever virus, Lujo virus, Marburg virus, Monkeypox virus, South American Haemorrhagic Fever viruses (Chapare, Guanarito, Junin, Machupo, Sabia), Tick-borne encephalitis complex (flavi) viruses (Far Eastern subtype, Siberian subtype), Kyasanur Forest disease virus, Omsk hemorrhagic fever virus, Variola major virus (Smallpox virus), Variola minor virus (Alastrim), Hendra virus, Nipah virus, Rift Valley fever virus, Venezuelan equine encephalitis virus, African horse sickness virus, African swine fever virus, Avian influenza virus, Classical swine fever virus, Foot-and-mouth disease virus, Goat pox virus, Lumpy skin disease virus, Newcastle disease virus, Peste des petits ruminants virus, Rinderpest virus, Sheep pox virus, and Swine vesicular disease virus.

In certain embodiments, the virus comprises at least one of Yellow fever virus, Rabies virus, Dengue virus, Human papillomavirus papilloma, Molluscum contagiosum virus, Variola virus, Poliovirus, Measles virus, Human herpesvirus 3, Human herpesvirus 1, Rift Valley fever virus, Influenza A virus, Lymphocytic choriomeningitis virus, St Louis encephalitis virus, Cercopithecine herpes virus 1, Japanese encephalitis virus, Louping ill virus, Mumps virus, Orf virus, Tick-borne encephalitis virus, Cowpox virus, Eastern equine encephalitis virus, Rubella virus, Venezuelan equine encephalitis virus, Western equine encephalitis virus, Influenza B virus, West Nile virus, Bwamba virus, Newcastle disease virus, Sandfly fever Naples virus, Sandfly fever Sicilian virus, Colorado tick fever virus, Omsk haemorrhagic fever virus, Encephalomyocarditis virus, Human enterovirus C, Human enterovirus A, Human enterovirus B, Influenza C virus, Vesicular stomatitis virus, Bunyamwera virus, California encephalitis virus, Murray Valley encephalitis virus, Ntaya virus, Human rhinovirus A, Human adenovirus B, Human adenovirus C, Human adenovirus E, Human adenovirus D, Chikungunya virus, Human herpesvirus 5, Human parainfluenza virus 2, Ilheus virus, Human adenovirus A, Human respiratory syncytial virus, Kyasanur forest disease virus, Mayaro virus, Wesselsbron virus, Human parainfluenza virus 1, Human parainfluenza virus 3, Human parechovirus, Junin virus, Banzi virus, Guaroa virus, Powassan virus, Human parainfluenza virus 4, Human rhinovirus B, Caraparu virus, Catu virus, O'nyong-nyong virus, Oropouche virus, Rio Bravo virus, Sindbis virus, Equine rhinitis virus A, Great Island virus, Pseudocowpox virus, Yaba monkey tumour virus, Human herpesvirus 4, Machupo virus, Zika virus, Chagres virus, Foot and mouth disease virus, Tanapox virus, Wyeomyia virus, Changuinola virus, Human coronavirus 229E, Quaranfil virus, Saimiriine herpesvirus 1, Chandipura virus, Crimean-Congo haemorrhagic fever virus, Human coronavirus OC43, Human enterovirus D, Piry virus, Tacaiuma virus, Human herpesvirus 2, Marburg virus, Tataguine virus, Everglades virus, Hepatitis B virus, Lassa virus, Punta Toro virus, Aroa virus, BK virus, Duvenhage virus, JC virus, Vaccinia virus, Bovine papular stomatitis virus, Mokola virus, Monkeypox virus, Norwalk virus, Ross River virus, Bangui virus, Dugbe virus, Hepatitis A virus, Kotonkan virus, Rotavirus A, Tamdy virus, Getah virus, B19 virus, Bhanja virus, Human astrovirus, Lebombo virus, Shuni virus, Thogoto virus, Orungo virus, Wanowrie virus, Hepatitis delta virus, Sudan Ebola virus, Zaire Ebola virus filo, Hantaan virus, Issyk-Kul virus, Human T-lymphotropic virus 1, Puumala virus, Human T-lymphotropic virus 2, Seoul virus, Candiru virus, Hepatitis E virus, Human adenovirus F, Human immunodeficiency virus 1, Human torovirus, Rotavirus B, Borna disease virus, European bat lyssavirus 2, Human herpesvirus 6, Human immunodeficiency virus 2, Kasokero virus, Kokobera virus, Rotavirus C, Dhori virus, Sealpox virus, Suid herpesvirus 1, Barmah Forest virus, Picobirnavirus birna, European bat lyssavirus 1, Hepatitis C virus, Banna virus, Gan Gan virus, Reston Ebola virus, Semliki Forest virus, Trubanaman virus, Guanarito virus, Dobrava-Belgrade virus, Sin Nombre virus, Hendra virus, Human herpesvirus 7, Human herpesvirus 8, Sabia virus, Bayou virus, Black Creek Canal virus, Cote d'Ivoire Ebola virus, Hepatitis G virus, New York virus, Andes virus, Australian bat lyssavirus, Juquitiba virus, Usutu virus, Laguna Negra virus, Menangle virus, Nipah virus, Torque teno virus, Whitewater Arroyo virus, Baboon cytomegalovirus, Human metapneumovirus, SARS coronavirus, Human coronavirus NL63, Human bocavirus, Human coronavirus HKU1, Human T-lymphotropic virus 3, and Human T-lymphotropic virus 4.

In certain embodiments, the virus comprises hepatitis C virus, hepatitis B virus, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV), and/or smallpox virus. In certain embodiments, the virus comprises an Orthomyxoviridae virus. In certain embodiments, the Orthomyxoviridae virus comprises an Alphainfluenzavirus, Betainfluenzavirus, Deltainfluenzavirus, Gammainfluenzavirus, Isavirus, Thogotovirus, and/or Quaranjavirus. In certain embodiments, the Alphainfluenzavirus comprises Influenza A virus, Influenza B virus, and/or Influenza C virus. In certain embodiments, the influenza A strain is H1N1, H2N2, H3N2, H5N1, H7N7, H1N2, H9N2, H7N2, H7N3, and/or H10N7. In certain embodiments, the virus comprises a Coronavirus. In certain embodiments, the Coronavirus comprises an Alphacoronavirus, a Betacoronavirus, a Gammacoronavirus, and/or a Deltacoronavirus. In certain embodiments, the Coronavirus is an Alphacoronavirus, such as but not limited to Alphacoronavirus 1, Human coronavirus 229E, Human coronavirus NL63, *Miniopterus* bat coronavirus 1, *Miniopterus* bat coronavirus HKU8, Porcine epidemic diarrhea virus, *Rhinolophus* bat coronavirus HKU2, and/or *Scotophilus* bat coronavirus 512. In certain embodiments, the Coronavirus is a Betacoronavirus, such as but not limited to Betacoronavirus 1 (Bovine Coronavirus, Human coronavirus OC43), Hedgehog coronavirus 1, Human coronavirus HKU1, Middle East respiratory syndrome-related coronavirus, Murine coronavirus, *Pipistrellus* bat coronavirus HKU5, *Rousettus* bat coronavirus HKU9, Severe acute respiratory syndrome-related coronavirus (SARS-CoV, SARS-CoV-2), and/or *Tylonycteris* bat coronavirus HKU4. In certain embodiments, the Coronavirus is a Severe acute respiratory syndrome-related coronavirus (SARS-CoV, SARS-CoV-2). In certain embodiments, the Coronavirus is a Severe acute respiratory syndrome-related coronavirus, SARS-CoV-2. In certain embodiments, the Coronavirus is a Gammacoronavirus, such as but not limited to Avian coronavirus and/or Beluga whale coronavirus SW1. In certain embodiments, the Coronavirus is a Deltacoronavirus, such as but not limited to Bulbul coronavirus HKU11 and/or Porcine coronavirus HKU15. In certain embodiments, the Coronavirus comprises at least one of MERS-CoV, SARS-CoV, and/or SARS-CoV 2, and/or a variant thereof. In certain embodiments, the Coronavirus comprises at least one variant of MERS-CoV, SARS-CoV, and/or SARS-CoV 2. In certain embodiments, the SARS-CoV-2 comprises at least one variant selected from B.1.1.7 (Alpha), B.1.351 (Beta), P.1 (Gamma), B.1.617.2 (Delta), B.1.429/B.1.427 (Epsilon), B.1.617.1 (Kappa), B.1.525 (Eta), B.1.526 (Iota), P.3 (Theta), P.2 (Zeta), and B.1.1.529 (Omicron). In certain embodiments, the SARS-CoV-2 comprises at least one variant selected from A.1-A.6, B.3-B.7, B.9, B.10, B.13-B.16, B.2, B.1 lineage (including, but not limited to, B.1, B.1.1, B.1.1.7, B.1.1.7 with E484K, B.1.2, B.1.5-B.1.72, B.1.9, B.1.13, B.1.22, B.1.26, B.1.37, B.1.3-B.1.66, B.1.177, B.1.243, B.1.313, B.1.351, B.1.427, B.1.429, B.1.525, B.1.526, B.1.526.1, B.1.526.2, B.1.617, B.1.617.1, B.1.617.2, B.1.617.3, B.1.619, B.1.620, and B.1.621), P.1, P.2, P.3, and R.1.

Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV) and smallpox virus. In certain embodiments, the infection is an upper respiratory tract infection caused by viruses and/or bacteria, in particular, flu, more specifically, bird flu.

Bacterial infections include, but are not limited to, infections by streptococci, staphylococci, *E. Coli*, and *pseudomonas*. In certain embodiments, the bacterial infection is an intracellular bacterial infection which is an infection by an intracellular bacterium such as mycobacteria (*tuberculosis*), *chlamydia, mycoplasma, listeria*, and an facultative intracellular bacterium such as *Staphylococcus aureus*.

Parasitic infections include, but are not limited to, worm infections, in particular, intestinal worm infection, microeukaryotes, and vector-borne diseases, including for example Leishmaniasis.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

Tumors include both benign and malignant tumors (i.e., cancer). Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, the cancer is selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, and Kaposi's sarcoma (AIDS-related and non-AIDS related).

Immune disorders include, but are not limited to, allergies, autoimmune disorders, and immunodeficiencies.

Allergies include, but are not limited to, respiratory allergies, contact allergies and food allergies.

Autoimmune diseases include, but are not limited to, multiple sclerosis, diabetes mellitus, arthritis (including rheumatoid arthritis, juvenile rheumatoid arthritis, osteoarthritis, psoriatic arthritis), encephalomyelitis, myasthenia gravis, systemic lupus erythematosis, autoimmune thyroiditis, dermatisis (including atopic dermatitis and eczematous dermatitis), psoriasis, Siogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

Respiratory disorders include, but are not limited to, acute lung injury (ALI), acute respiratory distress syndrome (ARDS), asthma, chronic obstructive pulmonary disease (COPD), obstructive sleep apnea (OSA), idiopathic pulmonary fibrosis (IPF), tuberculosis, pulmonary hypertension, pleural effusion, and lung cancer.

In certain embodiments, the nucleic acid molecule of the disclosure is used in combination with one or more pharmaceutically active agents such as immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies and gene silencing agents. Preferably, the pharmaceutically active agent is selected from the group consisting of an immunostimulatory agent, an anti-bacterial agent, an anti-viral agent, an anti-inflammatory agent and an anti-tumor agent. The more than one pharmaceutically active agents may be of the same or different category.

In certain embodiments, the nucleic acid molecule of the disclosure is used in combination with an antigen, an anti-viral vaccine, an anti-bacterial vaccine, and/or an anti-tumor vaccine, wherein the vaccine can be prophylactic and/or therapeutic. The nucleic acid molecule can serve as an adjuvant.

In another embodiment, the nucleic acid is used in combination with retinoic acid and/or type I IFN (IFN-α and/or IFN-β). Without being bound by any theory, retinoid acid, IFN-α and/or IFN-β are capable of sensitizing cells for IFN-β production, possibly through the upregulation of PRR expression.

In other embodiments, the nucleic acid molecule of the disclosure is for use in combination with one or more prophylactic and/or therapeutic treatments of diseases and/or disorders such as infection, tumor, and immune disorders. The treatments may be pharmacological and/or physical (e.g., surgery, radiation).

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a preferred embodiment, the mammal is human.

In certain embodiments, the nucleic acid molecule of the disclosure is used in combination with an anti-viral vaccine, wherein the vaccine can be prophylactic and/or therapeutic.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this disclosure may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In certain embodiments, the compositions of the disclosure are administered to the subject in dosages that range from one to five times per day or more. In another embodiment, the compositions of the disclosure are administered to the subject in range of dosages that include, but are not limited to, once every day, every two, days, every three days to once a week, and once every two weeks. It will be readily apparent to one skilled in the art that the frequency of administration of the various combination compositions of the disclosure will vary from subject to subject depending on many factors including, but not limited to, age, disease or disorder to be treated, gender, overall health, and other factors. Thus, the disclosure should not be construed to be limited to any particular dosage regime and the precise dosage and composition to be administered to any subject will be determined by the attending physical taking all other factors about the subject into account.

Compounds of the disclosure for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the disclosure is from about 1 mg and about 2,500 mg. In some embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the disclosure) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound or conjugate of the disclosure, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Pharmaceutical Compositions

The present disclosure provides a pharmaceutical composition comprising at least one nucleic acid molecule of the present disclosure and a pharmaceutically acceptable carrier. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as non-human primates, cattle, pigs, horses, sheep, cats, and dogs.

Pharmaceutical compositions that are useful in the methods of the disclosure may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the disclosure may further comprise one or more additional pharmaceutically active agents. Other active agents useful in the present disclosure include anti-inflammatories, including corticosteroids, and immunosuppressants, chemotherapeutic agents, antibiotics, antivirals, antifungals, and the like.

Controlled- or sustained-release formulations of a pharmaceutical composition of the disclosure may be made using conventional technology, using for example proteins equipped with pH sensitive domains or protease-cleavable fragments. In some cases, the dosage forms to be used can be provided as slow or controlled-release of one or more active ingredients therein using, for example, hydropropyl-methyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the disclosure. Thus, single unit dosage forms suitable for oral administration, such as tablets, capsules, gel-caps, and caplets, which are adapted for controlled-release are encompassed by the present disclosure.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present disclosure is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the disclosure may be administered in the form of microparticles, for example, by injection or in the form of wafers or discs by implantation.

In a preferred embodiment of the disclosure, the compounds of the disclosure are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences (1985, Genaro, ed., Mack Publishing Co., Easton, Pa.), which is incorporated herein by reference.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the disclosure may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the disclosure may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Routes of administration of any of the compositions of the disclosure include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the disclosure may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the disclosure which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present disclosure also includes a multi-layer tablet comprising a layer providing for the delayed release of one or more compounds of the disclosure, and a further layer providing for the immediate release of a medication for treatment of a disease. Using a wax/pH-sensitive polymer mix, a gastric insoluble composition may be obtained in which the active ingredient is entrapped, ensuring its delayed release.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the disclosure may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

A pharmaceutical composition of the disclosure may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

A pharmaceutical composition of the disclosure may be prepared, packaged, or sold in a formulation suitable for vaginal administration. With respect to the vaginal or perivaginal administration of the compounds of the disclosure, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present disclosure may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

A pharmaceutical composition of the disclosure may be prepared, packaged, or sold in a formulation suitable for pulmonary administration via the buccal cavity. Such a formulation may comprise dry particles which comprise the active ingredient and which have a diameter in the range from about 0.5 to about 7 micrometers, and preferably from about 1 to about 6 micrometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 micrometers and at least 95% of the particles by number have a diameter less than 7 micrometers. More preferably, at least 95% of the particles by weight have a diameter greater than 1 micrometer and at least 90% of the particles by number have a diameter less than 6 micrometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the disclosure formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 micrometers.

The formulations described herein as being useful for pulmonary delivery are also useful for intranasal delivery of a pharmaceutical composition of the disclosure.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the disclosure may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Kits

The disclosure also provides kits stimulating PRR activity and inducing an IFN response, as elsewhere described herein. In certain embodiments, the kit includes a composition comprising a nucleic acid molecule, as elsewhere described herein, and instructions for its use. The instructions will generally include information about the use of the compositions in the kit for the stimulation of PRR activity. The instructions may be printed directly on a container inside the kit (when present), or as a label applied to the container, or as a separate sheet, pamphlet, card, or folder supplied in or with the container.

The disclosure also provides kits for the treatment or prevention of a disease, disorder, or condition in which IFN production would be beneficial. In certain embodiments, the kit includes a composition (e.g. a pharmaceutical composition) comprising a nucleic acid molecule, as elsewhere described herein, and instructions for its use. The instructions will generally include information about the use of the compositions in the kit for the treatment or prevention of a disease or disorder or symptoms thereof. The instructions may be printed directly on a container inside the kit (when present), or as a label applied to the container, or as a separate sheet, pamphlet, card, or folder supplied in or with the container.

EXPERIMENTAL EXAMPLES

The disclosure is further described in detail by reference to the following experimental examples. These examples are provided for purposes of illustration only, and are not intended to be limiting unless so specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present disclosure, and are not to be construed as limiting in any way the remainder of the disclosure.

The materials and methods employed in the following Examples are now described.

Mice:

B6.Cg-Tg(K18-ACE2)2Prlmn/J (K18-hACE2), B6(Cg)-Ifnar1$^{tm1.2Ees}$/J (Ifnar1$^{-/-}$), B6.129S7-Rag1$^{tm1Mom}$/J (B6J Rag1$^{-/-}$), and C.129S7(B6)-Rag1$^{tm1Mom}$/J (BALB/c Rag1$^{-/-}$) mice were purchased from the Jackson Laboratories and were subsequently bred and housed at Yale University. Rag2$^{-/-}$ mice were gifted from R. Flavell (Yale University). 6- to 10-week-old mixed sex mice were used throughout the study. All mice were housed as groups of 5 to 6 individuals per cage and maintained on a 12-hour light/dark cycle (lights on at 7:00 AM) at 22-25° C. temperature and 30-70% relative humidity under specific-pathogen free conditions. All mice were fed with regular rodent's chow and sterilized water ad libitum.

Virus Sequencing:

Nucleic acid was extracted from 300 μL viral transport medium from nasopharyngeal swabs and eluted in 75 μL using the MagMAX viral/pathogen nucleic acid isolation kit. Extracted nucleic acid was tested by the multiplexed RT-qPCR variant assay (Vogels, et al., 2021, PLoS Biol 19, e3001236; Vogels, et al. (protocols.io, 2021), vol. 2021), and then libraries were prepared using the Illumina COVIDSeq Test RUO version. The protocol was slightly modified by lowering the annealing temperature of the amplicon PCR step to 63° C., and by reducing tagmentation to 3 minutes. Pooled libraries were sequenced on the Illumina NovaSeq (paired-end 150). Data was processed and consensus sequences were generated using iVar (version 1.3.1) with the minimum depth threshold (−m) at 20 and minimum frequency threshold (−t) at 0.6 (Grubaugh, et al., 2019, Genome Biol 20, 8). Genome sequences were uploaded to GISAID. Samples belonging to the B.1.1.7 (EPI_ISL_1038987), P.1 (EPI_ISL_1293215), and B.1.526 (EPI_ISL_944591) lineages were selected for virus isolation from the original sample. Virus belonging to the B.1.351 lineage was obtained from BEI Resources.

Virus Isolation:

Samples selected for virus isolation were diluted 1:10 in Dulbecco's Modified Eagle Medium (DMEM) and then filtered through a 45 μM filter. The samples were ten-fold serially diluted from 1:50 to 1:19,531,250. The dilution was subsequently incubated with TMPRSS2-Vero E6 in a 96 well plate and adsorbed for 1 hour at 37° C. After adsorption, replacement medium was added, and cells were incubated at 37° C. for up to 5 days. Supernatants from cell cultures with cytopathic effect (CPE) were collected, frozen, thawed and subjected to RT-qPCR. Fresh cultures were inoculated with the lysates as described above for viral expansion. Viral infection was subsequently confirmed through reduction of Ct values in the cell cultures with the multiplex variant qPCR assay. Expanded viruses were re-sequenced following the same method as described above and were identical to the original clinical sample sequence. Genome sequences of cultured viruses B.1.1.7 (SARS-CoV-2/human/USA/Yale-3363/2021; GenBank accession: MZ202178), B.1.351 (SARS-CoV-2/human/ZAF/Yale-3366/2020; GenBank accession: MZ202314), P.1 (SARS-CoV-2/human/USA/Yale-3365/2021; GenBank accession: MZ202306), and B.1.526 (SARS-CoV-2/human/USA/Yale-3362/2021; GenBank accession: MZ201303) were uploaded to GenBank. Nextclade v0.14.2 (clades dot nextstrain dot org/) was used to generate a phylogenetic tree and to compile a list of amino acid changes in the virus isolates as compared to the Wuhan-Hu-1 reference strain (Table 1; FIG. 36). Lineage defining amino acid changes were marked based on the outbreak.info lineage comparison (Mullen, et al., 2021, Lineage comparison (available at outbreak dot info/compare-lineages). Accessed 14 May 2021. outbreak.info 2021).

Synthesis, Purification, and Labeling of the SLR-14 Oligonucleotide

In certain embodiments, the nucleic acid molecule is a triphosphorylated or a dephosphorylated RNA oligonucleotide. In embodiments, the triphosphorylated RNA oligonucleotides SLR-14-Tp (5'-pppG-GAUCGAUCGAUCGUUCGCGAUCGAUCGAUCC-3', SEQ ID NO: 1) and SLR-14-amino-Tp (5'-pppG-GAUCGAUCGAUCGUXCGCGAUCGAUCGAUCC-3', where X=aminomodifier C6dT; Glen Research, SEQ ID NO: 2) were prepared as described (Jiang, et al., 2019, J Exp Med 216:2854-2868). In certain embodiments, the diphosphorylated RNA oligonucleotides SLR-14-Dp (5'-ppG-GAUCGAUCGAUCGUUCGCGAUCGAUCGAUCC-3', SEQ ID NO: 3) and SLR-14-amino-Dp (5'-ppG-GAUCGAUCGAUCGUXCGCGAUCGAUCGAUCC-3', where X=aminomodifier C6dT; Glen Research, SEQ ID NO: 4) were also prepared as described (Jiang, et al., 2019, J Exp Med 216:2854-2868).

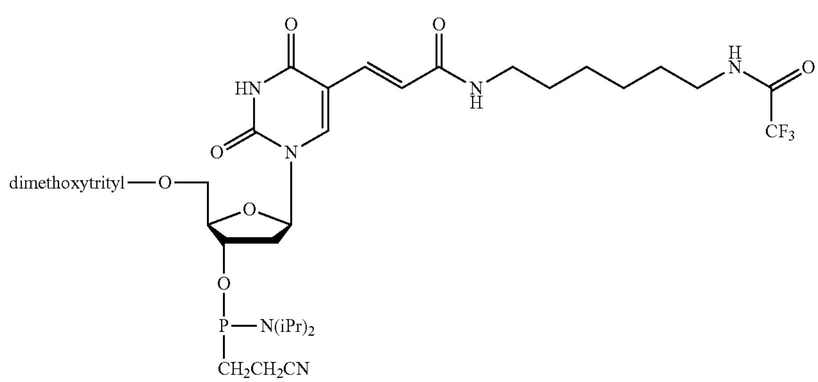

amino-modifier C6dT reagent
(Glen Research)

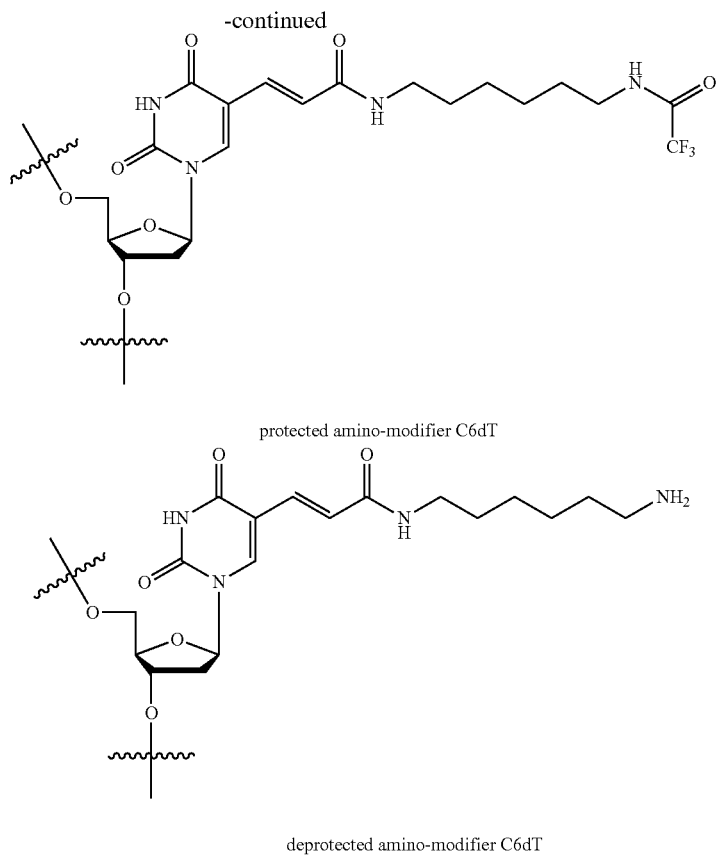

protected amino-modifier C6dT deprotected amino-modifier C6dT

Briefly, for every 1 mg of starting material, removal of the oligonucleotide from the polymer support and base deprotection was performed in a 1:1 mixture of 40% methylamine (Sigma-Aldrich) and 30% ammonium hydroxide (JT Baker) at 65° C. for 15 min. The solution was cooled on ice for 10 min, transferred to a new vial, and evaporated to dryness. 500 µL of absolute ethanol was added, and the mixture was evaporated to dryness again. To deprotect the 2'-OH groups, the dry oligonucleotide was incubated with 500 µL of a 1 M solution of tetrabutylammonium fluoride in tetrahydrofuran (Sigma-Aldrich) at room temperature for 36 h. 500 µL of 2 M sodium acetate (pH 6.0) was added, and the solution was evaporated to a 500-600 µL volume, extracted with 3×800 µL of ethyl acetate, and ethanol precipitated. The RNA oligonucleotide was then purified on a 16% denaturing polyacrylamide gel. For fluorescent labeling, for every 1 mg of starting material, the purified SLR14-amino oligonucleotide was dissolved in 200 µL of 0.25 M sodium bicarbonate buffer (pH 9.2). Then, a solution containing 0.5 mg of Alexa Fluor 647 NHS ester (Life Technologies Corp.) in 200 µL N,N-dimethylformamide was added, and the reaction mixture was incubated at room temperature for 2 h. The labeled oligonucleotide (AF647-SLR14) was ethanol precipitated and purified on a 20% denaturing polyacrylamide gel.

In Vivo SARS-CoV-2 Infection

Before infection, mice were anesthetized using 30% (vol/vol) isoflurane diluted in propylene glycol. For K18-hACE2 mice, 50 µL of SARS-CoV-2 was delivered intranasally at $10^3$ PFU per mouse (LD100), unless specified otherwise. Following infection, weight loss and survival were monitored daily up to 14 DPI. For AAV-hACE2 mice, 50 µL of SARS-CoV-2 was delivered intranasally at $10^6$ PFU per mouse. Experiments involving SARS-CoV-2 infection were performed in a Biosafety Level 3 facility with approval from the Yale Institutional Animal Care and Use Committee and Yale Environmental Health and Safety.

Antibody and Drug Treatment in Mice

For IFNAR blockade, mice were treated once with 2 mg of blocking antibodies diluted in 200 µL PBS one day prior to infection (Clone MAR1-5A3; BioXCell). Universal Type I IFN (rIFN-αA/D; PBL Assay Science, No 11200) was supplied frozen in PBS containing 0.1% BSA. Cross-species activities of rIFN-αA/D on mouse cells were confirmed by the manufacturer and published studies (Uccellini and Garcia-Sastre, 2018). 4 hours post infection, $2×10^4$ U rIFN-αA/D (low-dose; $10^6$ U/kg) or $2×10^5$ U rIFN-αA/D (high-dose; $10^7$ U/kg) were diluted in 100 µL PBS and intravenously administered to mice. STING agonist diABZI (Compound 3; Selleckchem) was first reconstituted in DMSO at 50 mg/mL. 20 µg diABZI (1 mg/kg) was diluted in 100 µL PBS and intravenously administered to mice 4 hours post infection. The dosage for systemic diABZI treatment was determined based on previous publications (Humphries et al., 2021; Ramanjulu et al., 2018). The dosing solution was prepared fresh and confirmed to be clear at the time of administration.

Intravenous Injection of SLR14 in Mice:

At indicated timepoints, 15 µg SLR14 was i.v. injected. Briefly, 15 µg (~0.6 mg/kg body weight) SLR14 and 4 µL jetPEI (Polyplus Transfection) were diluted and mixed with 5% glucose solution to a total of 100 µL injection solution per mouse. After 15 min of incubation at room temperature, the 100-µL complex was carefully injected into the retro-orbital sinus with a 0.5-mL BD Insulin syringe. Before injection, mice were anesthetized using 30% (vol/vol) isoflurane diluted in propylene glycol. $H_2O$ and jetPEI were mixed with 5% glucose solution and used as a vehicle control.

AAV-hACE2 Transduction:

AAV9 vector encoding hACE2 was purchased from Vector Biolabs (AAV9-CMV-hACE2). Animals were anaesthetized using a mixture of ketamine (50 mg/kg) and xylazine (5 mg/kg), injected intraperitoneally. The rostral neck was shaved and disinfected. A 5-mm incision was made, the salivary glands were retracted, and the trachea was visualized. Using a 32-G insulin syringe, a 50-μL bolus injection of $10^{11}$ genomic copies AAV-CMV-hACE2 was injected into the trachea. The incision was closed with 4-0 Vicryl suture. Following intramuscular administration of analgesic (meloxicam and buprenorphine, 1 mg/kg), animals were placed on a heating pad and closely monitored until full recovery.

Adoptive Transfer of Sera:

WT AAV-hACE2 mice were infected with SARS-CoV-2 as indicated elsewhere herein. At 14 DPI animals were euthanized for blood collection. Blood was allowed to coagulate at room temperature for 30 min and then centrifuged at 3900 rpm for 20 min at 4° C. Serum was collected, and anesthetized mice (30% v/v Isoflurane diluted in propylene glycol) were injected with 200 μL serum with a 32 g 8 mm syringe via retro orbital route.

Measurements of Genomic RNA and Infectious Virus:

Viral RNA and titer from mouse lung tissues were measured as previously described (Israelow, et al., 2020, J Exp Med 217). Briefly, at indicated time points, mice were euthanized with 100% isoflurane. The whole lung was placed in a Lysing Matrix D tube (MP Biomedicals) with 1 mL of PBS, and homogenized using a table-top homogenizer at medium speed for 2 min. For RNA analysis, 250 μL of the lung homogenates was added to 750 μL Trizol LS (Invitrogen), and RNA was extracted with the RNeasy Mini Kit (Qiagen) according to the manufacturer's instructions. SARS-CoV-2 RNA levels were quantified with 250 ng of RNA inputs using the Luna Universal Probe One-Step RT-qPCR Kit (New England Biolabs), using real-time RT-PCR primer/probe sets 2019-nCoV_N1 (CDCN1) and 2019-nCoV_N2 (CDCN2). For determination of infectious titer, plaque assays were performed using lung homogenates in Vero E6 cells cultured with MEM supplemented with $NaHCO_3$, 4% FBS, and 0.6% Avicel RC-581. 48 h after infection, plaques were resolved by 1 h fixation with 10% formaldehyde and sequentially 1 h staining with 0.5% crystal violet in 20% ethanol. Finally, plates were rinsed in water for better visualization of plaques.

Immunohistochemistry

Mice were first perfused by intracardiac injection 20 mL of PBS into the right ventricle until the lung appears opaque. After perfusion, the lung was slowly inflated with 1 mL of 4% paraformaldehyde (PFA) (Electron Microscopy Sciences) through intratracheal instillation. Following inflation, the trachea was quickly tied with suture. Tissue was collected and fixed in 4% PFA overnight. Yale Pathology kindly assisted with embedding, sectioning, and H&E staining of lung tissues. H&E-stained lung sections were then imaged by a fluorescence microscopy (BX51; Olympus) with a 10× lens.

BALF Collection

Mice were euthanized with 100% isoflurane. After euthanasia, the trachea was exposed and the lung was slowly inflated with 1 mL of PBS through intratracheal instillation. Lung tissues were flushed three times. Following lavage, samples were centrifuged at 3900 rpm for 5 min at 4° C.; the supernatant (i.e. BALF) was aliquoted in 100 μL aliquots and stored at −80° C.

Antibodies for Flow Cytometry:

Anti-mouse antibodies used herein, together with vendors and dilutions, are listed as follows: FITC anti-mCD11c (N418) (1:400) (BioLegend), PerCP-Cy5.5 anti-mLy6C (HK1.4) (1:400) (BioLegend), Alexa Fluor 700 anti-mLy6G (1A8) (1:400) (BioLegend), Brilliant Violet 786 anti-mCD11b (M1/70) (1:400) (BioLegend), APC-Cy7 anti-mTCRb (H57-597) (1:400) (BioLegend), APC-Cy7 anti-mCD3 (H57-597) (1:400) (BioLegend), APC-Cy7 anti-mCD19 (6D5) (1:400) (BioLegend), APC-Cy7 anti-mNK1.1 (PK136) (1:400) (BioLegend), PE anti-mCD64 (X54-5/7.1) (1:200) (BioLegend), Brilliant Violet 711 anti-mSiglecF (E50-2440) (1:200) (BD Biosciences), and Pacific Blue anti-mI-A/I-E (M5/114.15.2) (1:400) (BioLegend).

Figure 27A:
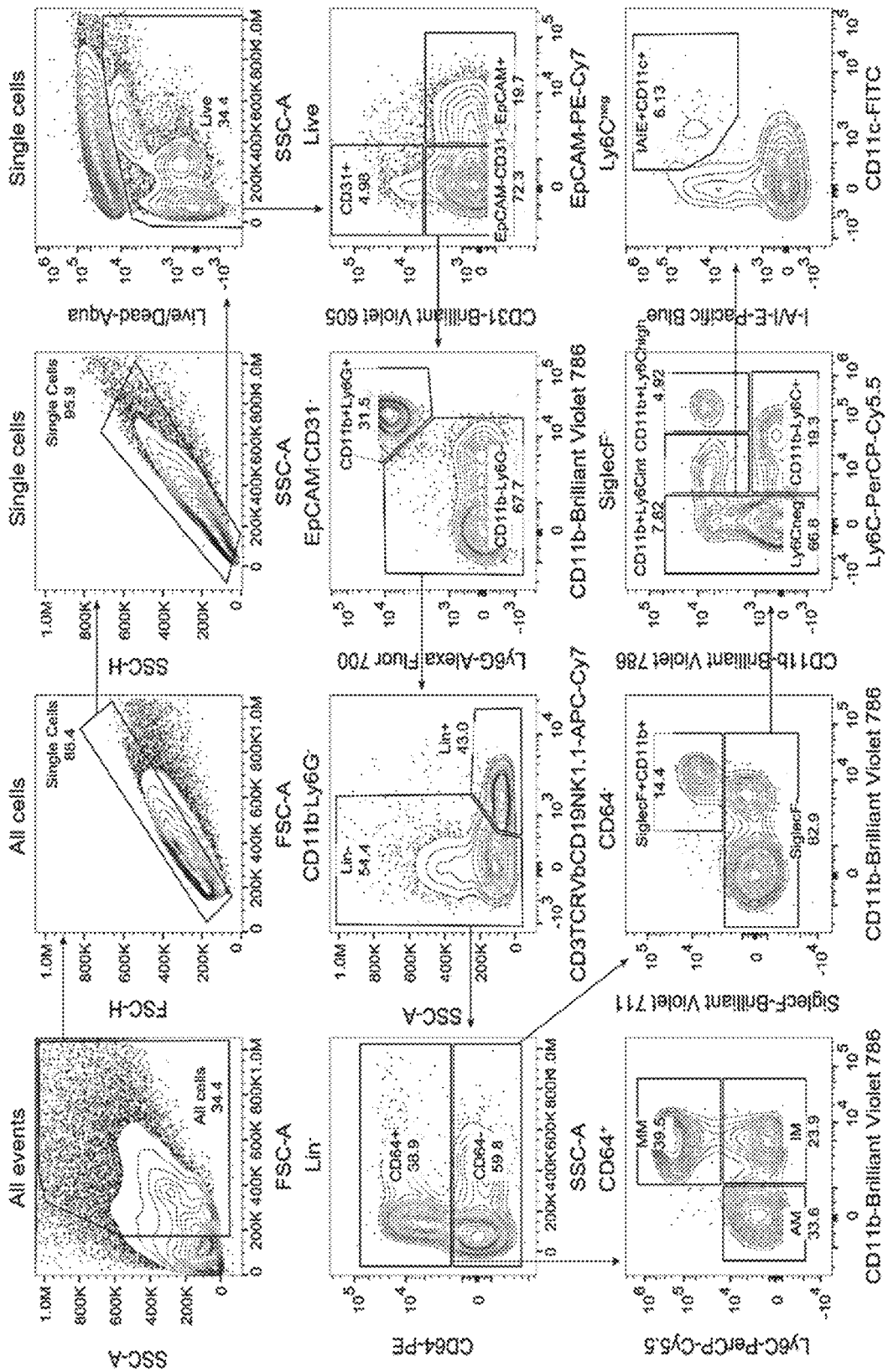
FIGS. 27A-27B illustrate gating strategies for immunological and SLR14 uptake analyses in the lung by flow cytometry.
Figure 27B:
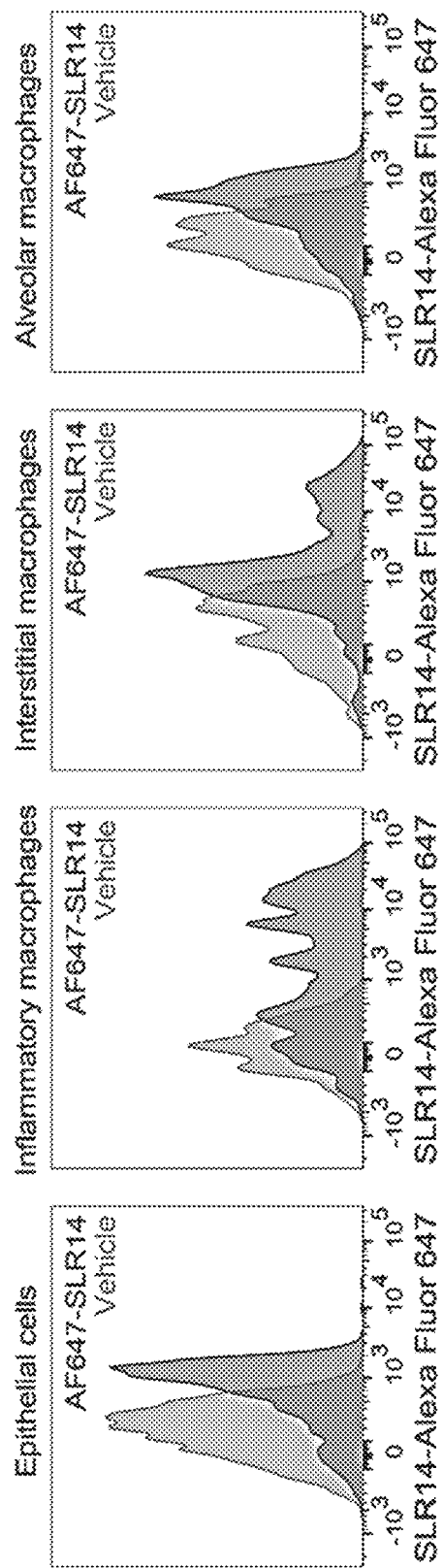

Flow Cytometry:

Mouse lung tissues were collected at experimental endpoint, digested with 1 mg/mL collagenase A (Roche) and 30 μg/mL DNase I (Sigma-Aldrich) in complete RPMI-1640 media for 30 min at 37° C., and mechanically minced. Digested tissues were then passed through a 70 μm strainer (Fisher Scientific) to single cell suspension and treated with ACK Lysing Buffer (ThermoFisher) to remove red blood cells. Cells were resuspended in Live/Dead Fixable Aqua (ThermoFisher) for 20 min at 4° C. Following a wash, cells were blocked with anti-mouse CD16/32 antibodies (BioXCell) for 30 min at 4° C. Cocktails of staining antibodies were added directly to this mixture for 30 min at 4° C. Prior to analysis, mouse cells were washed and resuspended in 100 μL 4% PFA for 30-45 min at 4° C. Following this incubation, cells were washed and prepared for analysis on an Attune NXT (ThermoFisher). Data were analysed using FlowJo software version 10.6 software (Tree Star). The specific sets of markers used to identify each subset of cells are summarized in FIGS. 27A-27B.

SARS-CoV-2-Specific Antibody ELISA Measurement

SARS-CoV-2-specific antibodies were measured as previously described (Israelow et al., 2021). In brief, sera were treated with 0.5% Triton X-100 and 0.5 mg ml$^{-1}$ RNase A to inactivate potentially infectious viruses. Recombinant SARS-CoV-2 S1 protein (ACRO Biosystems, S1N-C52H3) was used to coat 96-well MaxiSorp plates (Thermo Scientific) overnight. The coating buffer was removed, and plates were treated with blocking solution followed by incubation with diluted serum. Plates were washed with PBS-T and HIRP anti-mouse IgG antibody were added to each well. After incubation plates were washed with PBS-T and developed with TMB Substrate Reagent Set (BD Biosciences 555214). The reaction was stopped by 2 N sulfuric acid. Plates were then read at a wavelength of 450 nm and 570 nm.

Determination of Type I and Type III IFN Concentration

Concentration of type I IFN in BAL fluid was determined by ELISA (PBL Assay Science, No 42120 and 42400) following the manufacturer's instructions. IFN-α pre-coated plates were incubated for 24 h with diluted or undiluted samples and target antibody, followed by wash with PBS-T. Similarly, IFN-β pre-coated plates were incubated with undiluted samples for an hour and washed with PBS-T. Detection antibody was added and incubated for 1 hour followed by a second wash. Both plates were then treated with HRP solution and washed before addition of TMB Substrate solution. The reaction was left to develop for 10 and 15 minutes, respectively, and stopped with 2 N Sulfuric acid. Absorbance was recorded at 450 nm and background noise was subtracted from the negative control in the experiment. Concentration of IFN-λ in BAL fluid was determined by ELISA (R&D Systems, DY1789B) according to manufacturer's instructions. 96-well MaxiSorp plates (Thermo Scientific) were coated overnight with 1 μg/mL of Coating Antibody. After wash with PBS-T, the plates were blocked with 1% bovine serum albumin (BSA) in PBS for 1 hour, and subsequently incubated for two hours with diluted or undiluted samples. The plate was washed and incubated for 2 hours with Detection antibody followed by a third wash. Streptavidin-HRP treatment was performed for 20 minutes and washed before addition of TMB Substrate solution. The reaction was left to develop for 8 minutes and stopped with 2 N Sulfuric acid. Absorbance was recorded at 450 nm and background noise was subtracted from the negative control in the experiment.

Statistical Analysis:

The data were analyzed by log-rank Mantel-Cox test or one-way ANOVA followed by Tukey correction. All statistical tests were calculated using GraphPad Prism (GraphPad software). A P value of <0.05 was considered statistically significant.

Graphical Illustrations:

Graphical illustrations were made with Biorender.com.

Example 1: Ability of Small Hairpin RNAs to Induce Interferon In Vivo

Experiments were conducted to examine the ability of small hairpin RNAs to induce interferon production in vivo. Mice were injected in the tail vein with jetPEI/RNA complex (i.v.), and serum was collected at 5 hours post-injection. The dose used per mouse was as follows: polyIC=25 ug, hp10=640 uM (25.15 ug), hp414=640 uM (33.4 ug). 4 mice were used for each condition. Blood was collected five hours post-injection. The blood was left at 4° overnight to clot. It was then centrifuged for 30 minutes at 4° (3000 prm), and the serum (supernatant) was collected. The results indicate that very high levels of IFNalpha are induced by shRNAs and polyIC, and not by the vehicle control (FIG. 1). Notably, the shRNAs induce more IFNalpha than polyIC. Note that hp10 is a 5'-triphosphorylated 10 base-pair duplex with a UUCG tetraloop at one end (same as 5'-ppp10L) and hp14 is a 5'-triphosphorylated 14 base pair duplex with a UUCG tetraloop at one end. The polyIC is low molecular weight poly IC.

Figure 2:
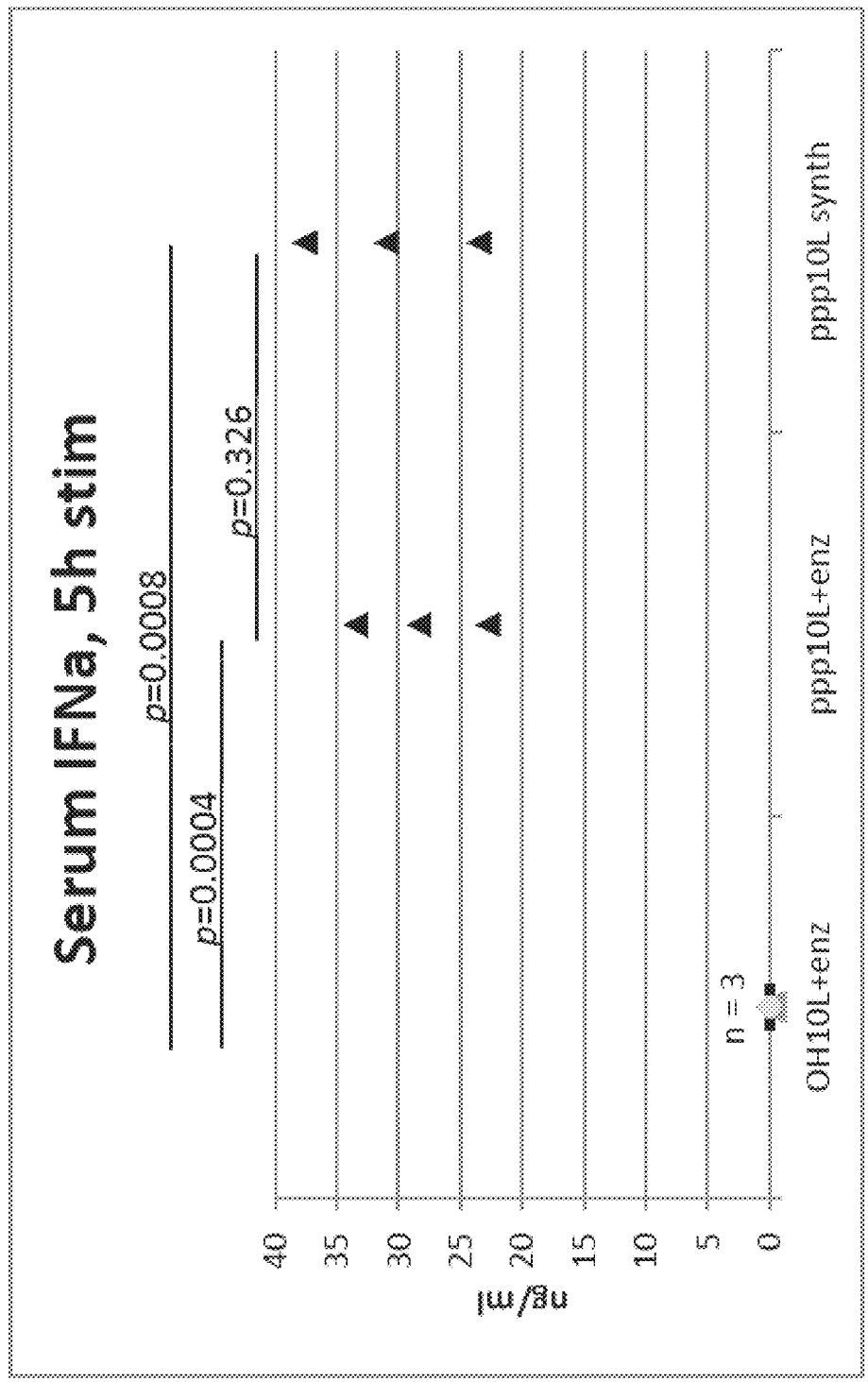
FIG. 2 is a graph depicting the results of a representative experiment depicting serum Interferon alpha levels after treatment with dephosphorylated and triphosphorylated short hairpin RNAs: Mice were injected in the tail vein with jetPEI/RNA complex (i.v.), and serum was collected at 5 hours post-injection, n=3 per group. RNA #1 (center, ppp10L+enz)=5'-ppp10L transcribed and then treated with Dnase/Prot K, then phenol extraction and ethanol precipitation. RNA #2 (left, OH 10L+enz)=5'OH10L, which is transcribed 5'-ppp10L treated with CIP, then enzyme treated/purified as above. RNA #3 (right, ppp10L synth)=5'-ppp10L that is machine-synthesized, abiological. It is demonstrated that only 5'-ppp10L (whether transcribed or synthetic), and not RNA lacking triphosphate (left), induces interferon. Both transcribed and synthesized 5'-ppp10L induce IFN to a similar degree, although the synthetic triphosphorylated RNA is slightly more active. Extra enzyme treatment and purification of transcribed 5'-ppp10L does not impact IFN levels.

Further experiments were conducted to compare IFNα production induced by three different RNA constructs. Mice were injected in the tail vein with jetPEI/RNA complex (i.v.), and serum was collected at 5 hours post-injection, n=3 per group. The first construct is 5'-ppp10L transcribed and treated with Dnase/Prot K, purified using phenol extraction and EtOH precipitation. The second construct is 5'-OH10L, which is the 5'-ppp10L, treated and purified as above, and then treated with CIP. The third construct is a synthesized and abological form of 5'-ppp10L. Blood was collected five hours post-injection. The blood was left at 4° overnight to clot. It was then centrifuged for 30 minutes at 4° (3000 prm), and the serum (supernatant) was collected. It was observed that only 5'-ppp10L (whether transcribed or synthetic), and not RNA lacking triphosphate, induces interferon (FIG. 2). Both transcribed and synthesized 5'-ppp10L induce IFN to a similar degree, although the synthetic triphosphorylated RNA is slightly more active. Extra enzyme treatment and purification of transcribed 5'-ppp10L does not impact IFN levels (as compared to data shown in FIG. 1).

Figure 8A:
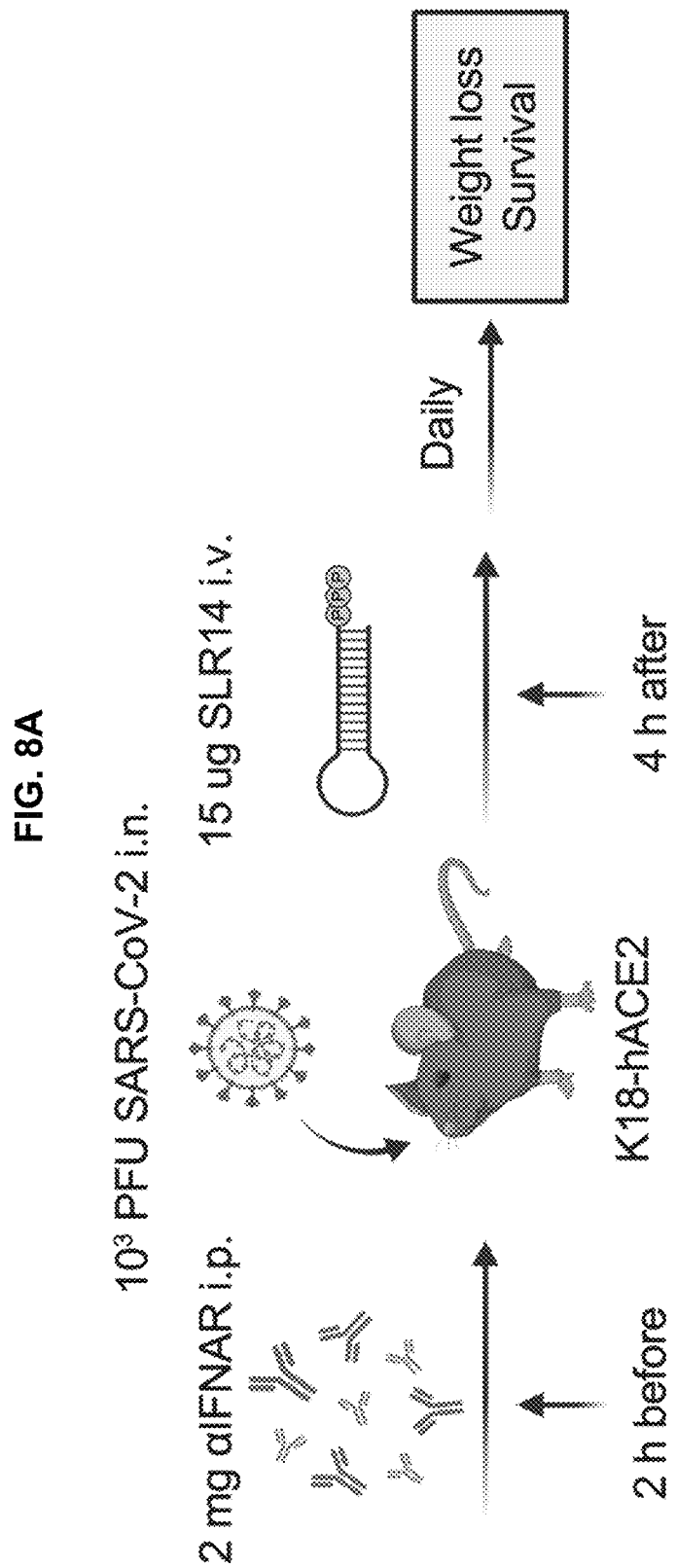
FIGS. 8A-8C illustrate a non-limiting experiment testing the role of type I interferon signaling in SLR14-mediated protection.
Figure 8B:
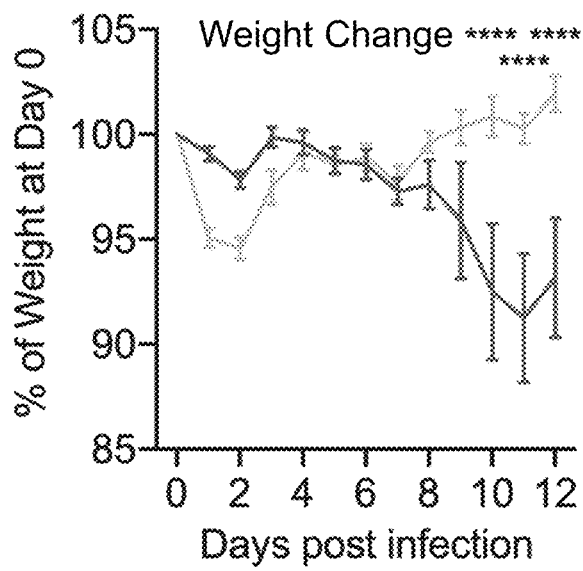
Figure 8C:
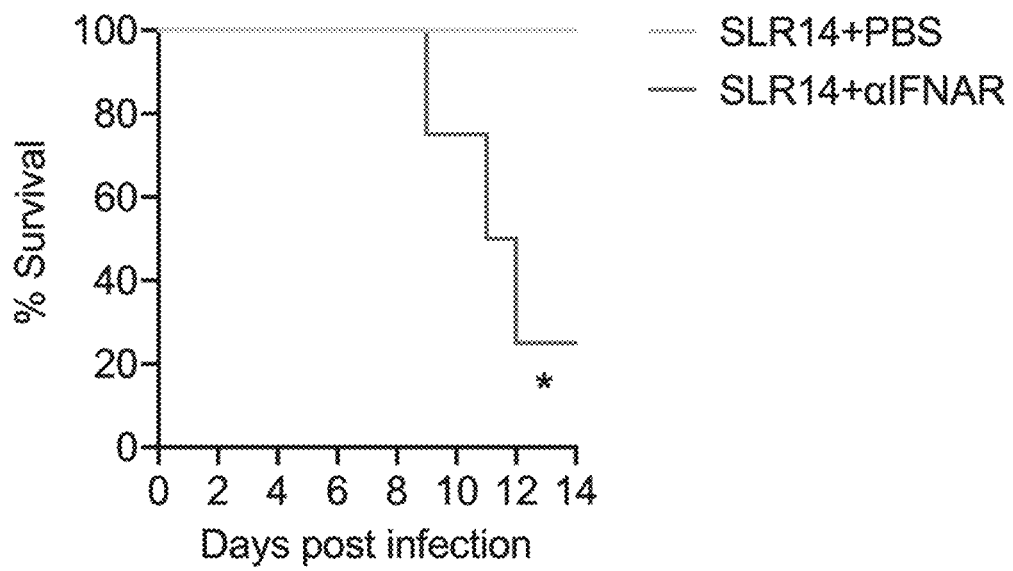

FIGS. 8A-8C illustrate a non-limiting experiment testing the role of type I interferon signaling in SLR14-mediated protection. FIG. 8A: Treatment scheme—2 hours before infection, K18 mice were intraperitoneally treated with 2 mg of anti-IFNAR blocking antibodies or PBS, followed by intranasal infection with $10^3$ PFU SARS-CoV-2. 15 μg SLR14 or vehicle were intravenously administered 4 hours post infection. Weight loss and survival were monitored daily. FIG. 8B: Weight changes compared to day 0 (day of infection) of anti-IFNAR- and PBS-treated K18 mice from day 0 to day 14 were measured. FIG. 8C: Survival, defined as 10% weight loss compared to day 0, of anti-IFNAR- and PBS-treated K18 mice from day 0 to day 14 was measured. Mean±s.e.m., two-way ANOVA followed by Sidak correction (b), log-rank Mantel-Cox test (c); *P≤0.05, P≤0.01, *P≤0.001, ****P≤0.0001.

Example 2: Ability of Small Hairpin RNAs to Treat or Prevent Viral Infection (Influenza Virus)

Figure 3A:
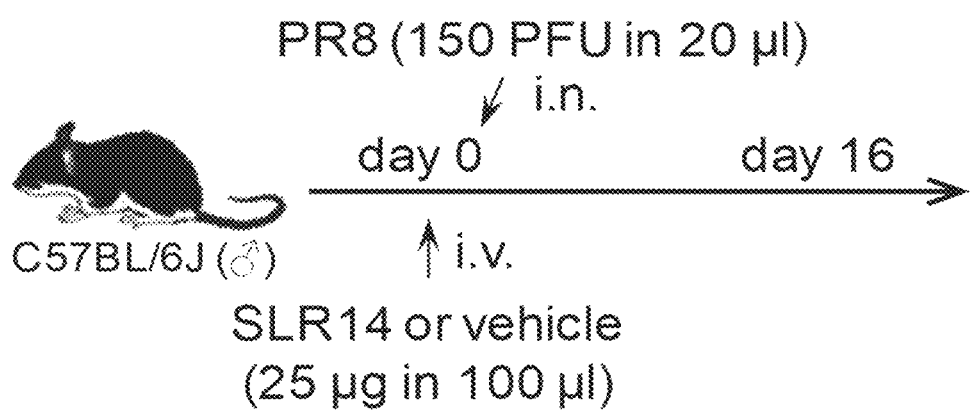
FIGS. 3A-3C illustrate that SLR14 intravenous treatment protects C57BL/6J mice from influenza virus infection.
Figure 3B:
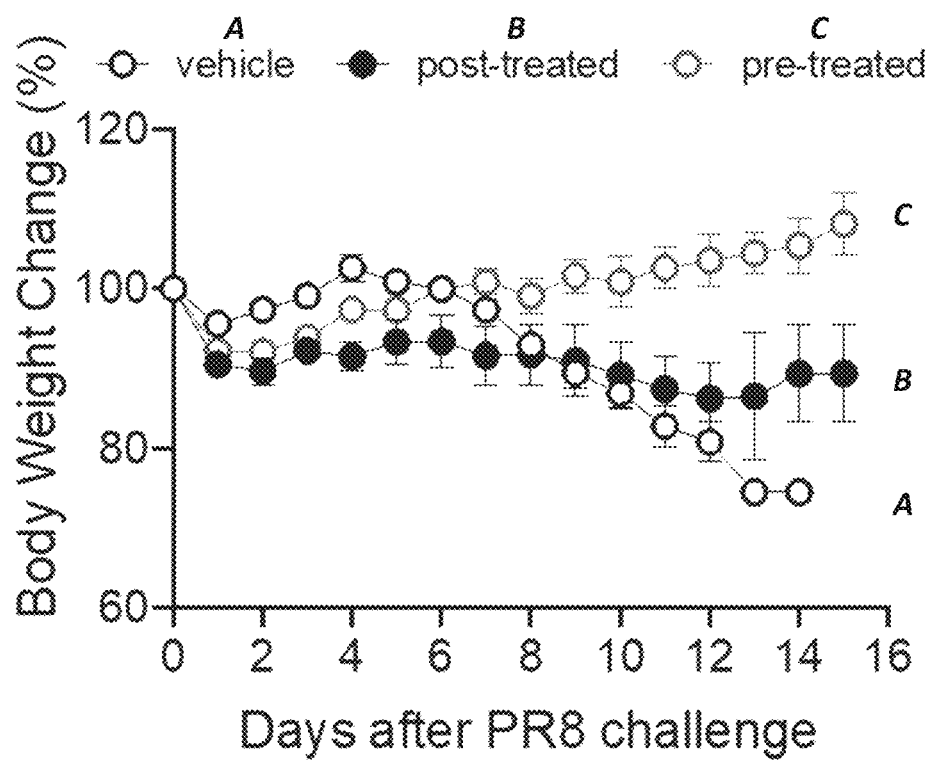
Figure 3C:
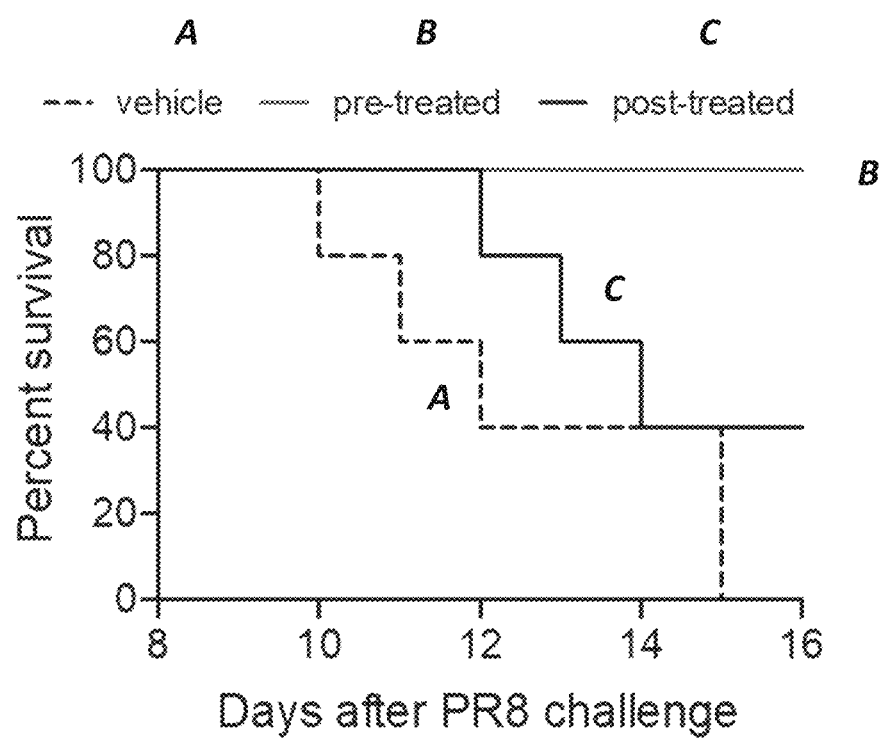

As demonstrated herein (see, for example, FIGS. 3A-3C), small hairpin RNAs can be used to treat, ameliorate, or prevent influenza virus infection. In a non-limiting example, SLR14 intravenous treatment was shown to protect C57BL/6J mice from influenza virus infection. As illustrated in FIG. 3A, naïve C57BL/6J mice (male, 8 weeks) received SLR14 intravenous (i.v.) treatment 5 hours before (pre-treated) or after (post-treated) intranasal (i.n.) challenge with PR8 (which is a mouse-adapted H1N1 influenza virus that is known to cause severe infection in mice). The mice treated intravenously with vehicle (jetPEI) were used as controls. As illustrated in FIG. 3B, the SLR14-treated mice (both pre-treated and post-treated) showed less body weight loss than vehicle-treated mice after PR8 challenge, but the pre-treated animals consistently showed less body weight loss than the post-treated animals overall. Consistently, as demonstrated in FIG. 3C, the pre-treated animals showed 100% survival, while the post-treated animals showed % survival that was still higher than the vehicle-treated animals, after PR8 challenge. Taken together, the data demonstrate that pre-treatment of animals with the small hairpin RNAs before PR8 exposure prevents development of influenza infection, while pre-treatment of animals with the small hairpin RNAs significantly minimizes the severity of the influenza infection.

Figure 11A:
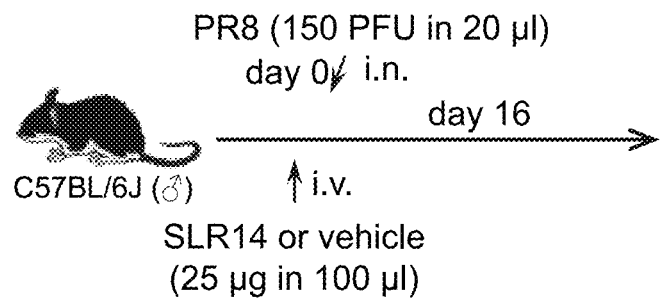
FIGS. 11A-11C illustrate the finding that SLR14 intravenous treatment protects C57BL/6J mice from influenza virus infection.
Figure 11B:
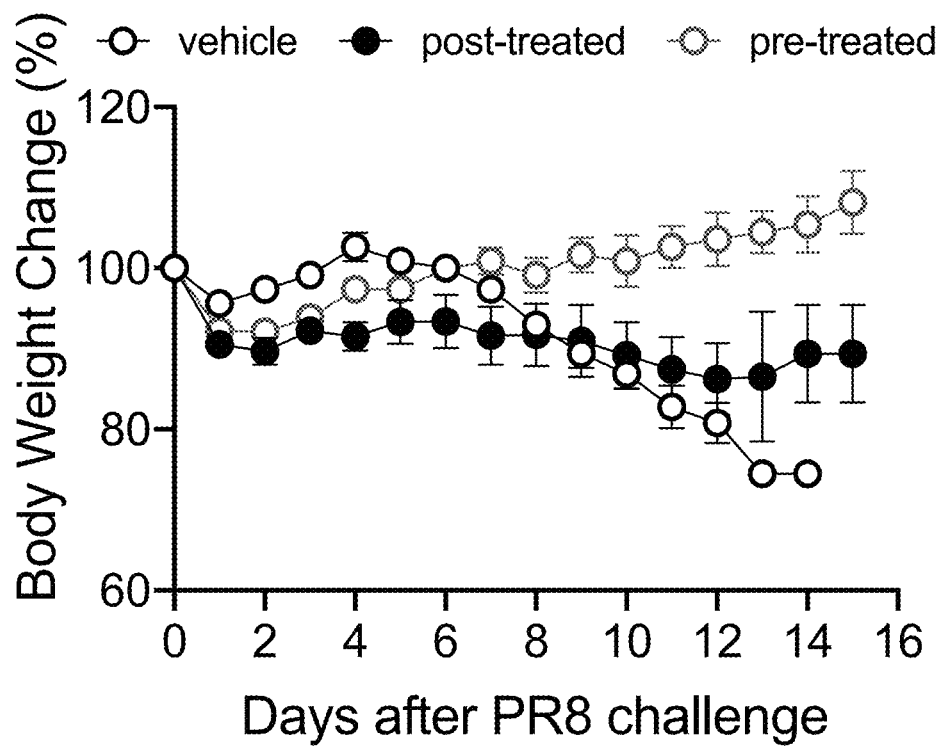
Figure 11C:
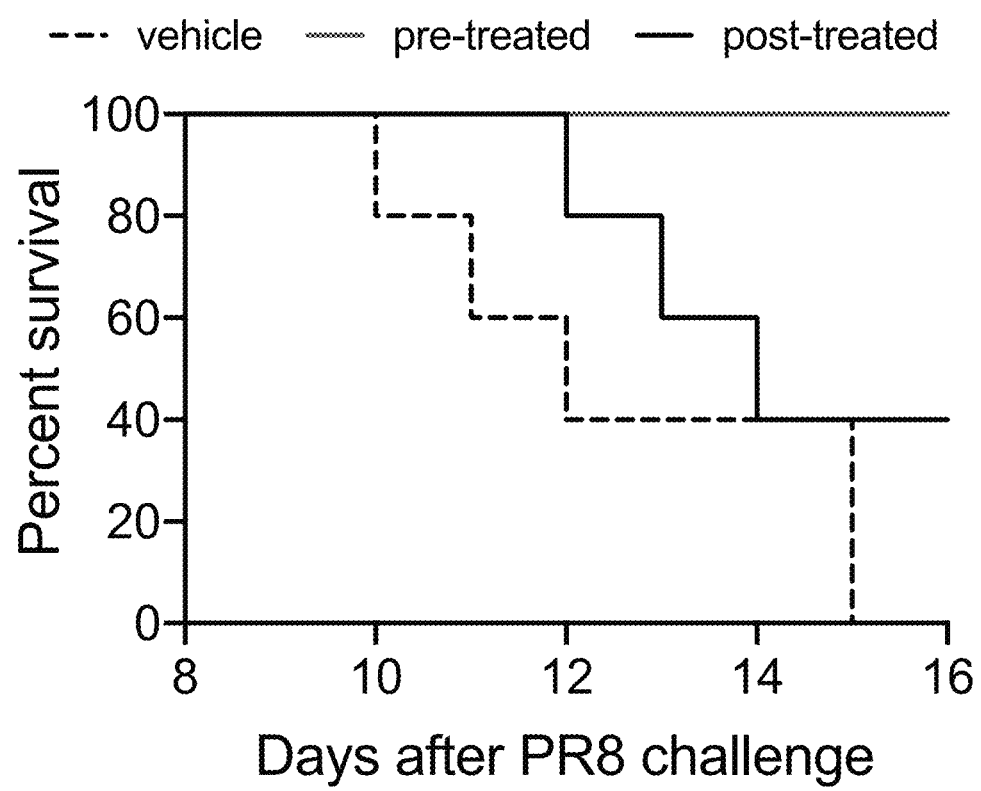

FIGS. 11A-11C illustrate the finding that SLR14 intravenous treatment protects C57BL/6J mice from influenza virus infection. FIG. 11A: Naïve C57BL/6J mice (male, 8 weeks) received SLR14 intravenous (i.v.) treatment 5 hours before (pre-treated) or after (post-treated) intranasal (i.n.) challenge with PR8. The mice treated intravenously with vehicle (jetPEI) were used as controls. FIG. 11B: Body weight loss in SLR14- or vehicle-treated mice after PR8 challenge. FIG. 11C: The survival of SLR14- or vehicle-treated mice after PR8 challenge.

Example 3: Ability of Small Hairpin RNAs to Treat or Prevent Viral Infection (Coronavirus)

Figure 4A:
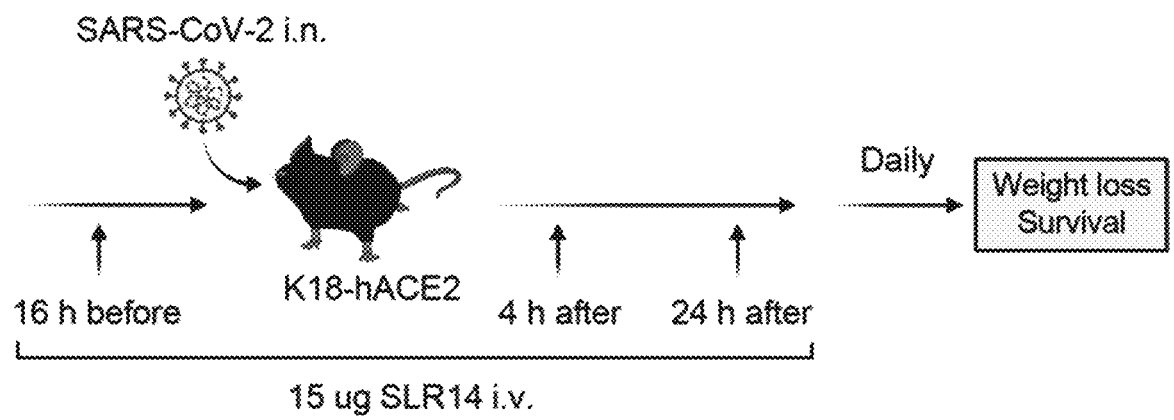
FIGS. 4A-4C illustrate the finding that SLR14 treatment timing relative to virus replication determines protective activities.
Figure 4B:
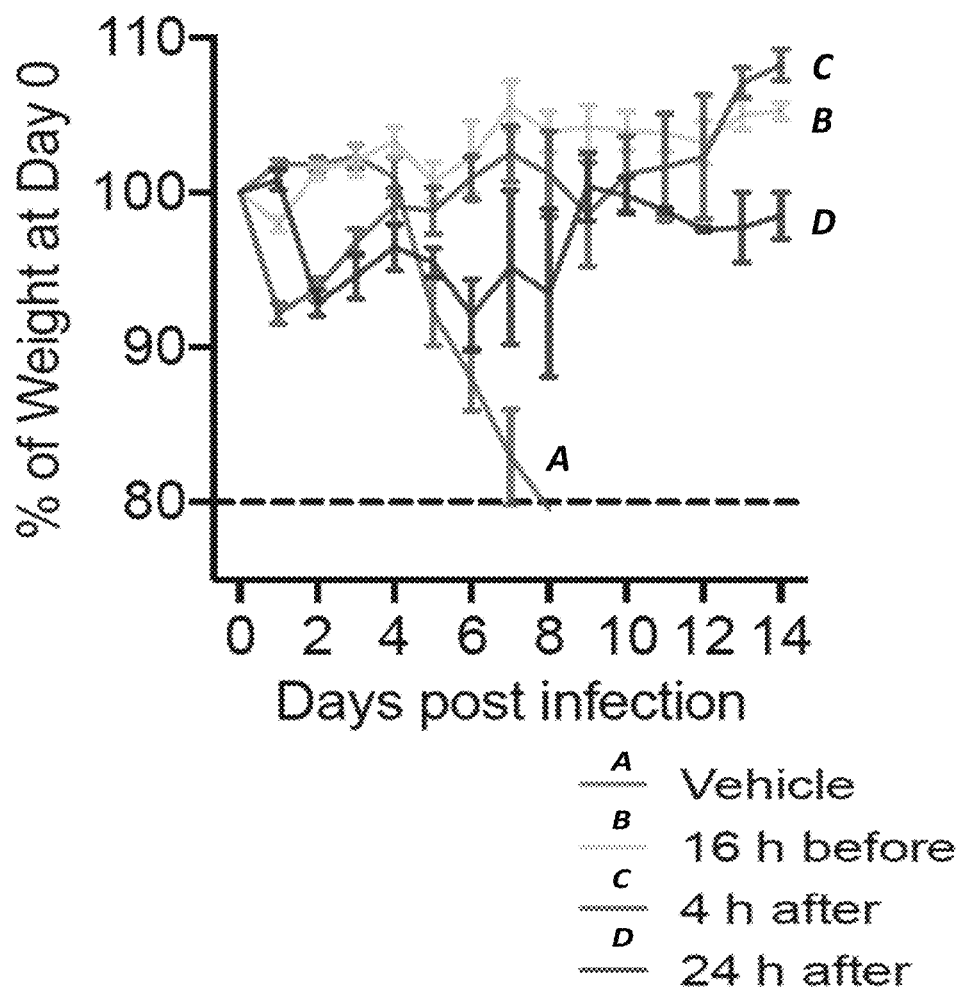
Figure 4C:
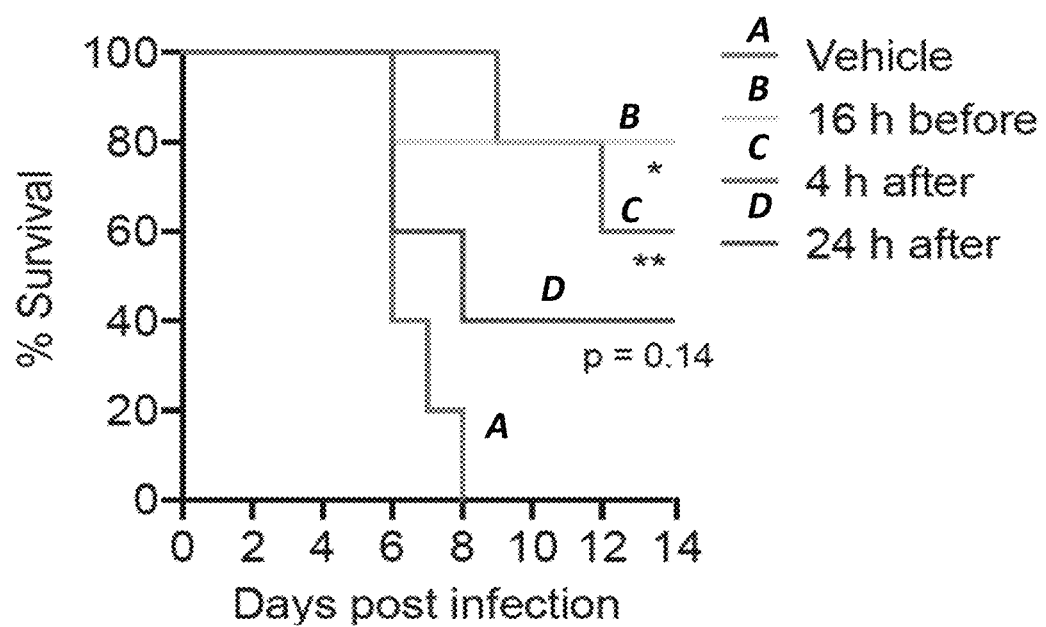
Figure 5A:
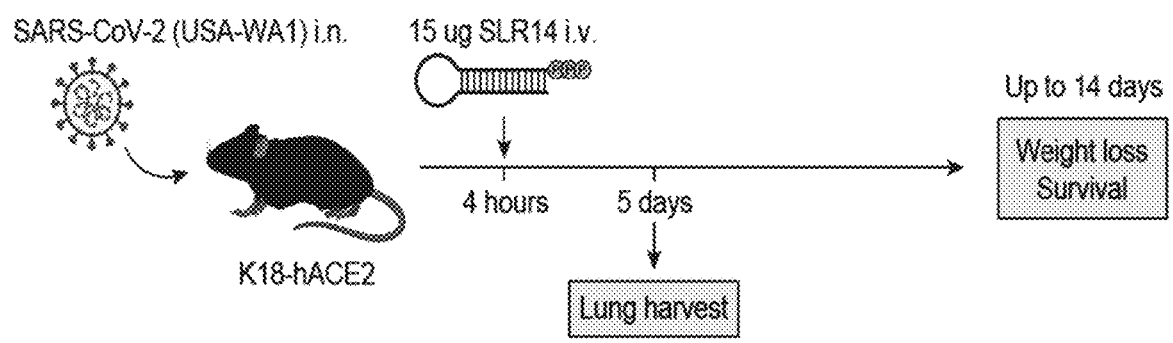
Figure 5B:
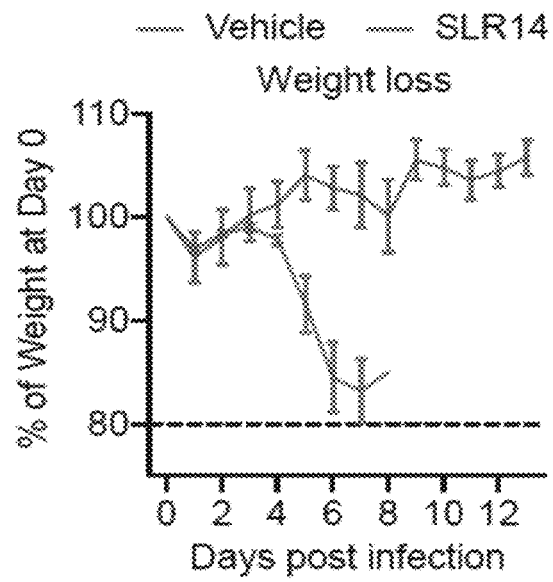
Figure 5C:
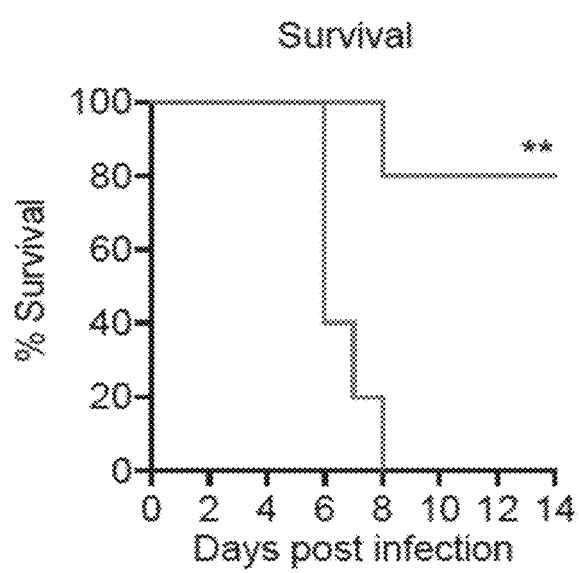
Figure 6:
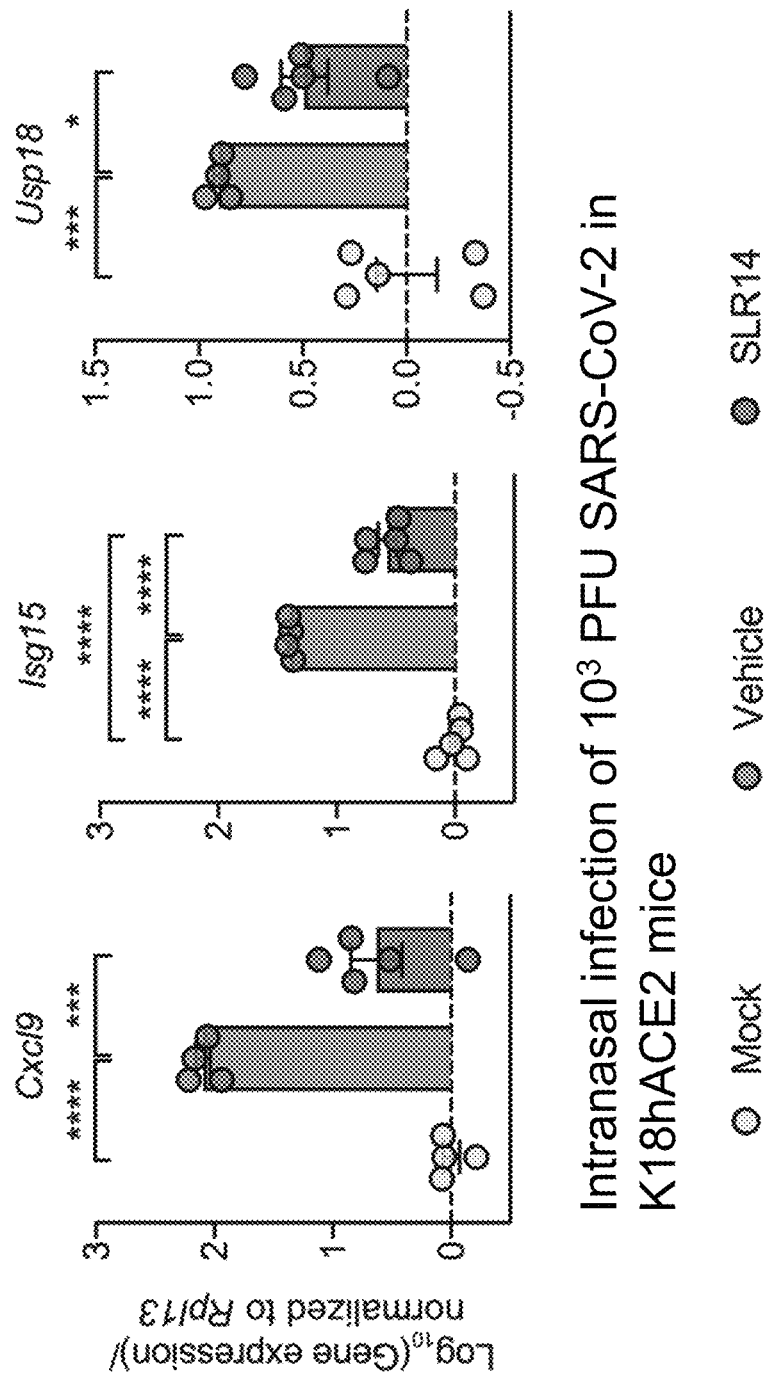
FIG. 6 illustrates the finding that low ISG induction corroborates a virus-free state in SLR14-treated mice.

FIGS. 4A-4C illustrate the finding that SLR14 treatment timing relative to virus replication determines protective activities against coronavirus infection. FIG. 4A illustrates a non-limiting treatment scheme: K18 mice were intranasally infected with 10' PFU SARS-CoV-2. 15 μg SLR14 or vehicle were intravenously administered either 16 hours before, 4 hours post, or 24 hours post infection. Weight loss and survival were monitored daily. FIG. 4B illustrates weight changes compared to day 0 (day of infection) of SLR14- and vehicle-treated K18 mice from day 0 to day 14. FIG. 4C illustrates survival, defined as 20% weight loss compared to day 0, of SLR14- and vehicle-treated K18 mice from day 0 to day 14. Mean±s.e.m., log-rank Mantel-Cox test (c); *P≤0.05, P≤0.01, *P≤0.001, ****P≤0.0001.

Figure 7A:
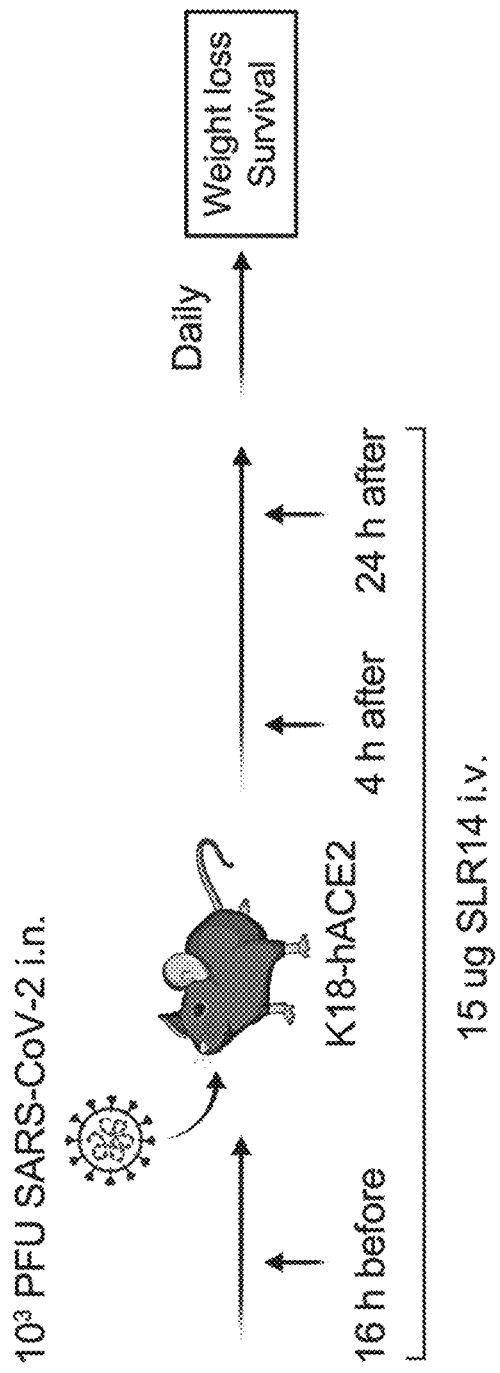
FIGS. 7A-7C illustrate a non-limiting experiment testing the effect of treatment timing on SLR14-mediated protection. As demonstrated herein, SLR14 treatment timing relative to virus replication determines protective activities.
Figure 7B:
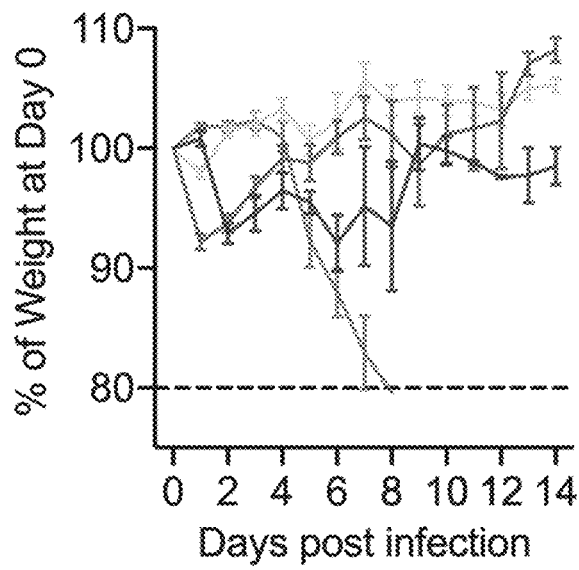
Figure 7C:
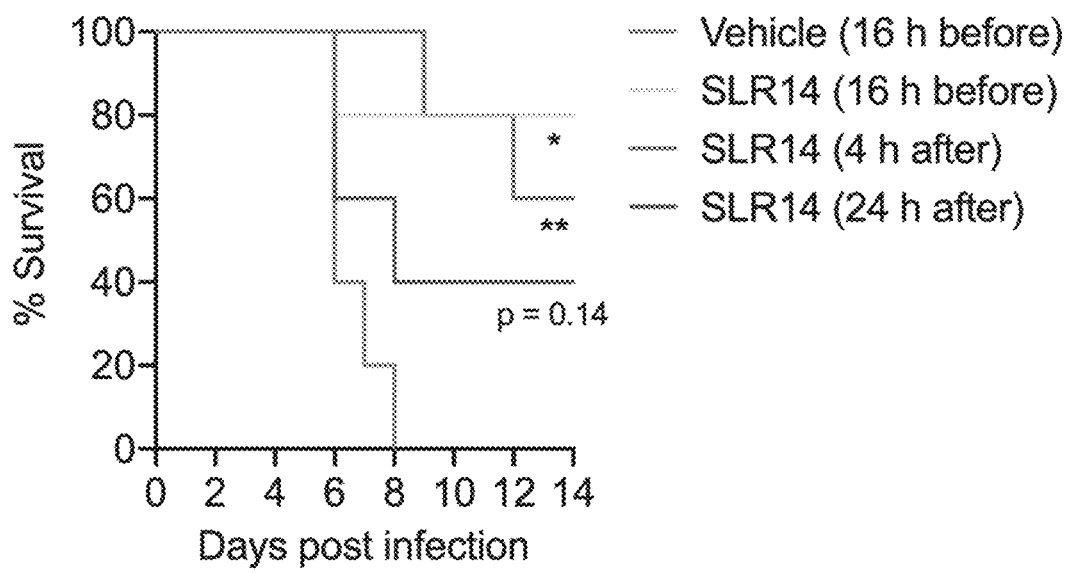

Example 4: Effect of Treatment Timing on Small Hairpin RNA-Mediated Protection in Viral Infections FIGS. 7A-7C illustrate a non-limiting experiment testing the effect of treatment timing on SLR14-mediated protection. As demonstrated herein, SLR14 treatment timing relative to virus replication determines protective activities. FIG. 7A: Treatment scheme—K18 mice were intranasally infected with $10^3$ PFU SARS-CoV-2. 15 µg SLR14 or vehicle were intravenously administered either 16 hours before, 4 hours post, or 24 hours post infection. Weight loss and survival were monitored daily. FIG. 7B: Weight changes compared to day 0 (day of infection) of SLR14- and vehicle-treated K18 mice from day 0 to day 14 were measured. FIG. 7C: Survival, defined as 20% weight loss compared to day 0, of SLR14- and vehicle-treated K18 mice from day 0 to day 14 was measured. Mean±s.e.m., log-rank Mantel-Cox test (c); *P≤0.05, P≤0.01, *P≤0.001, ****P≤0.0001.

Figure 16A:
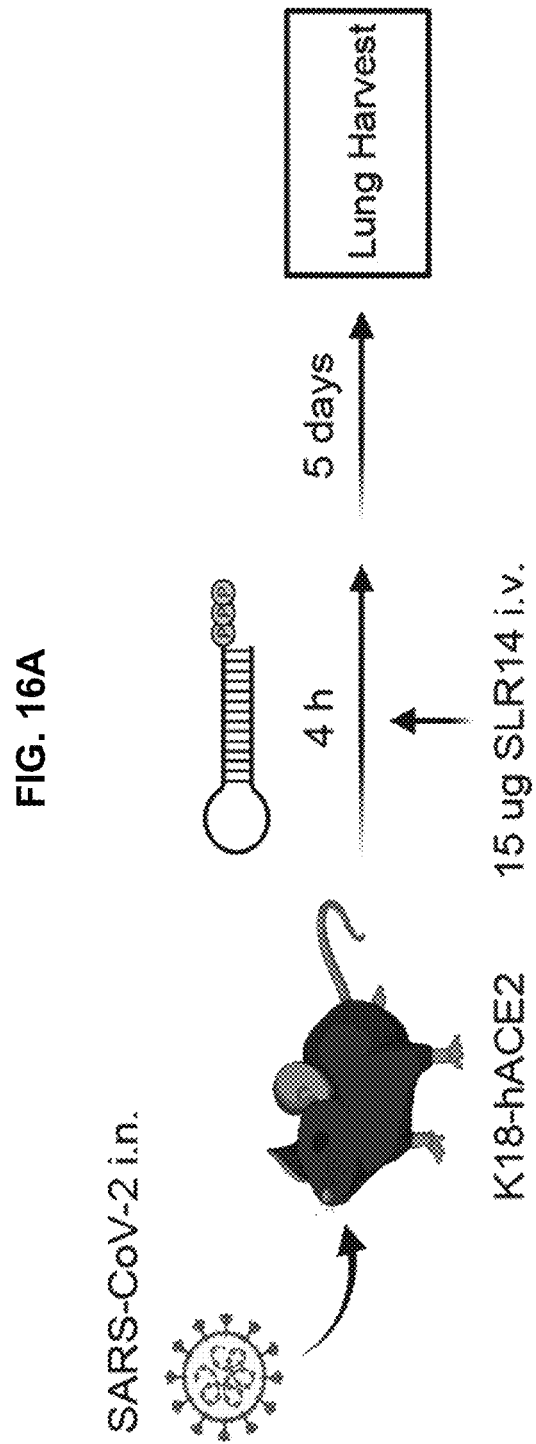

Example 5: A Single Dose of SLR14 Confers Potent Antiviral Protection Against Lethal SARS-Cov-2 Infection To examine the antiviral activity of SLR14 in vivo, a mouse model of SARS-CoV-2 infection that transgenically expresses human angiotensin-converting enzyme 2 (ACE2) under the keratin 18 gene promoter, also known as the K18-hACE2 mice, was used (McCray, et al., 2007, J Virol 81:813-821). Intranasal infection with SARS-CoV-2 in K18-hACE2 mice leads to viral replication, pulmonary inflammation, and respiratory dysfunction, recapitulating key aspects of infection and pathogenesis seen in patients with COVID-19. Intravenous (i.v.) injection of SLR14 complexed with polyethyleneimine (PEI) results in rapid, short-lived, and systemic IFN-I responses that peak as early as 2 hours post injection and decline to undetectable levels within 24 hours of injection. K18-hACE2 mice were intranasally infected with the ancestral strain of SARS-CoV-2 (2019n-CoV/USA_WA1/2020), SLR14 was administered i.v. 4 hours post infection, and survival and weight loss daily were monitored thereafter (FIG. 5A). SLR14 treatment considerably prevented weight loss and dramatically improved survival following the infection (FIGS. 5B-5C). In contrast, vehicle-treated mice uniformly lost weight and developed apparent signs of sickness behaviors such as reduced motility and hyporesponsiveness, rapidly succumbing to infection by 8 days post infection (DPI). These results showed that SLR14 effectively alleviates morbidity and reduces mortality, affording protection against lethal SARS-CoV-2 infection in vivo.

Example 6: Ability of Small Hairpin RNAs to Ameliorate, Minimize, Reverse, and/or Prevent Persistent Viral Infection, and/or Minimize or Prevent Viral Infection-Derived Mortality and/or Lethality FIGS. 5A-5I also illustrate the finding that SLR14 treatment SLR14 confers protection against lethal SARS-CoV-2 infection in human ACE2 transgenic K18 mice. FIG. 5A: Treatment scheme: K18-hACE2 transgenic (K18) mice expressing human ACE2 were intranasally infected with $10^3$ (FIGS. 5B-5C) or $5\times10^4$ (FIGS. 5D-5I) PFU SARS-CoV-2. 4 hours post infection, 15 g SLR14 or vehicle were intravenously administered. Weight loss and survival were monitored daily. FIG. 5B: Weight changes compared to day 0 (day of infection) of SLR14- and vehicle-treated K18 mice from day 0 to day 14 were measured. FIG. 5C: Survival, defined as 20% weight loss compared to day 0, of SLR14- and vehicle-treated K18 mice from day 0 to day 14 was measured. FIGS. 5D-5F: SARS-CoV-2 N (FIGS. 5D-5E) or E gene (FIG. 5F) expression from lung homogenates were measured 5 days post infection by quantitative PCR. FIGS. 5G-5I: Expression of interferon stimulated genes (ISG) Cxcl9 (FIG. 5G), Isg15 (FIG. 5H), and Usp18 (FIG. 5I) from lung homogenates were measured at day 5 post infection. Mean±s.e.m., two-way ANOVA followed by Sidak correction (FIG. 5B), log-rank Mantel-Cox test (FIG. 5C), one-way ANOVA followed by Tukey correction (FIG. 5D-5I); $*P\leq0.05$, $P\leq0.01$, $*P\leq0.001$, $****P\leq0.0001$.

To investigate the mechanisms by which SLR14 mediates protection, lung tissues were collected from naïve as well as infected mice treated with SLR14 or vehicle 5 DPI. Given the crucial role for RIG-I activation in the initiation of antiviral immunity, the impact of SLR14 treatment was first assessed on lung viral burden. Striking reduction in the level of genomic RNA (by RT-qPCR) and complete clearance of infectious virus (by plaque assay) in lung tissues from SLR14-treated mice was observed compared to vehicle control (FIGS. 5D-5F). These results confirm that SLR14 affords protection against SARS-CoV-2 by efficiently mediating viral clearance in the lung tissue. Consistent with the absence of infectious virus, significantly attenuated expression of ISGs, including Cxcl9, Isg15, and Usp18, was observed in lung tissues from SLR14-treated mice at this timepoint (FIGS. 5G-5I). In contrast, abundant ISG expression was detected in lungs from vehicle-treated mice, likely resulting from high viral burden.

To further probe the impact of SLR14 during SARS-CoV-2 infection, immune infiltrates in lung tissues from these mice were assessed. Markedly decreased $CD11b^+$ $Ly6C^+$ monocyte-derived proinflammatory macrophages were observed in SLR14-treated mice 5 DPI (FIG. 5J). Additionally, SLR14 treatment led to a significant reduction in the surface expression of MHC class II molecules on $Ly6C^{high}$ monocytes (FIG. 5K). To directly assess the impact of SLR14 on immunopathology, histological analyses were performed on hematoxylin and eosin (H&E)-stained lung sections from SARS-CoV-2 infected K18-hACE2 mice treated with vehicle or SLR14 5 DPI. Widespread viral pneumonia associated with immune infiltration at alveolar and interstitial locations in lung sections from SARS-CoV-2-infected vehicle-treated mice were found (FIG. 34). In contrast, minimal inflammatory infiltrates in lung tissues from SLR14-treated mice were found. Together, these results indicated that in addition to providing viral control, SLR14 protects lung tissues from SARS-CoV-2 infection-induced viral pneumonia.

FIG. 6 illustrates the finding that low interferon-stimulated genes (ISGs) induction corroborates a virus-free state in SLR14-treated mice.

FIGS. 16A-16D illustrate that SLR14 alleviates inflammatory burden and reduces lung pathology in lethal SARS-CoV-2 infection. FIG. 16A: Treatment scheme—K18 mice were intranasally infected with $5\times10^4$ PFU SARS-CoV-2. 4 hours post infection, 15 μg SLR14 or vehicle were intravenously administered. 5 days post infection, lung tissues were collected. FIGS. 16B-16D: Pulmonary immune responses following SARS-CoV-2 infection. Frequency of CD11b+ CD64+ macrophages (FIG. 16B), Ly6C$^{high}$ monocytes (FIG. 16C) as well as mean fluorescence intensity of MHCII on Ly6C$^{high}$ monocytes (FIG. 16D) were measured by flow cymetry. Mean±s.e.m., one-way ANOVA followed by Tukey correction (FIGS. 16B-16D); *$P \leq 0.05$, $P \leq 0.01$, *$P \leq 0.001$, ****$P \leq 0.0001$.

Figure 9B:
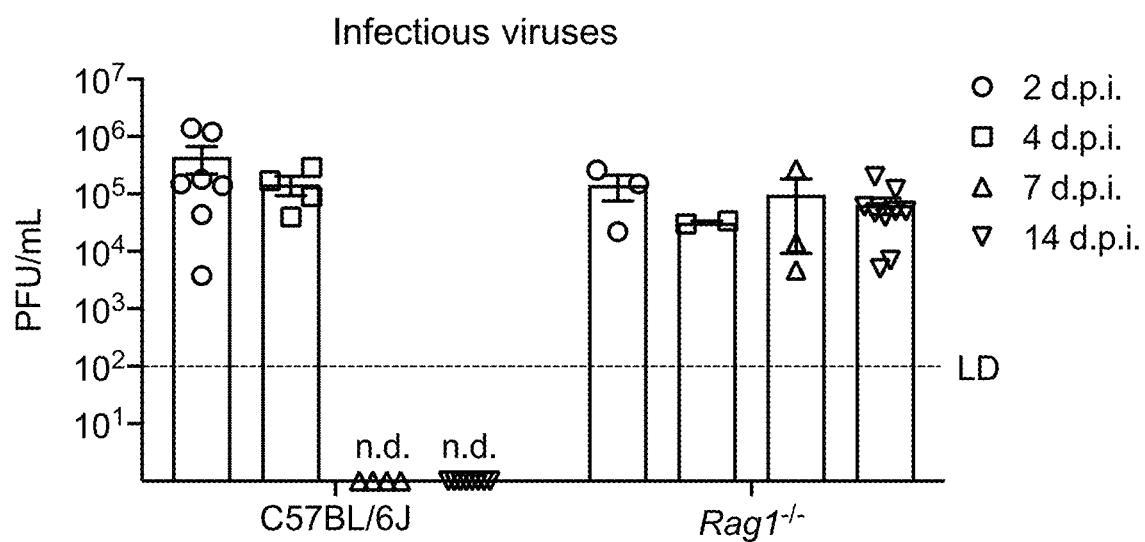

FIGS. 9A-9B illustrate a non-limiting experiment testing the effect of therapeutic SLR14 in treating persistent infection and long COVID.

Figure 10A:
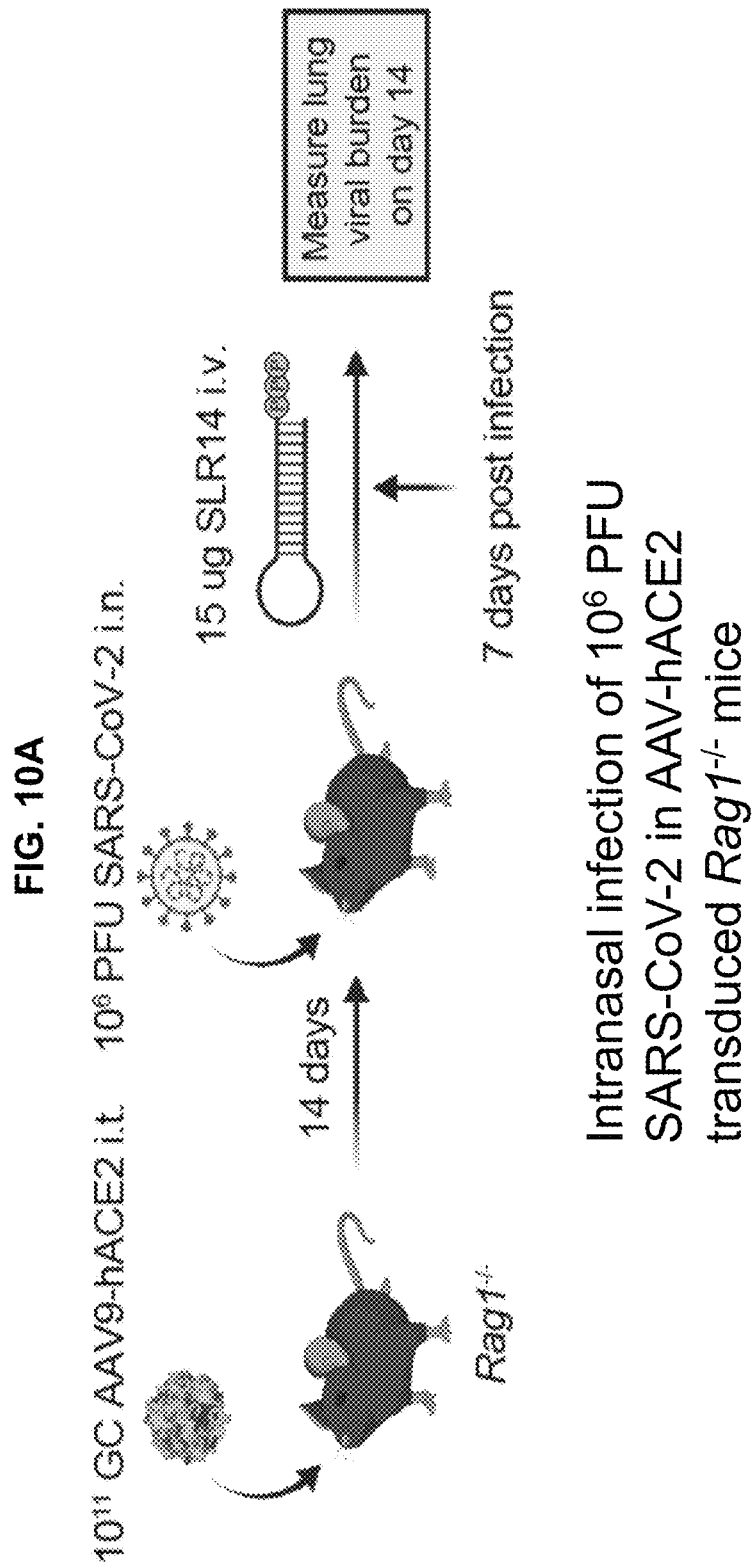
FIGS. 10A-10C illustrate the finding that therapeutic SLR14 clears persistent SARS-CoV-2 infection in Rag1$^{-/-}$ mice.
Figure 10B:
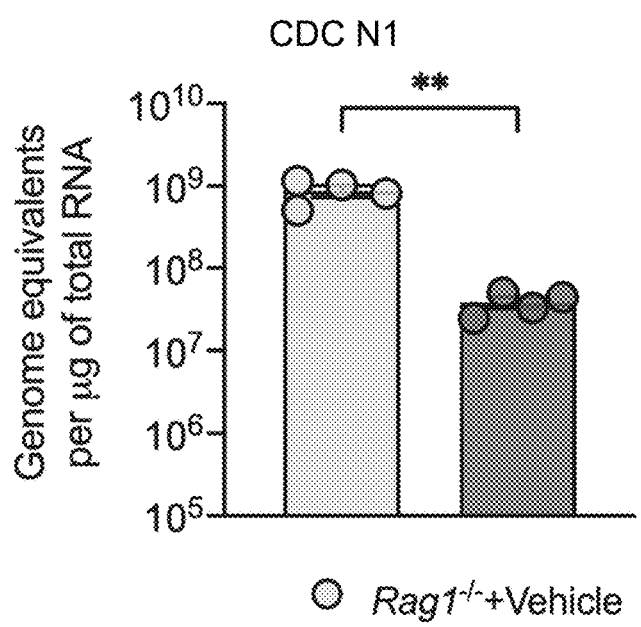
Figure 10C:
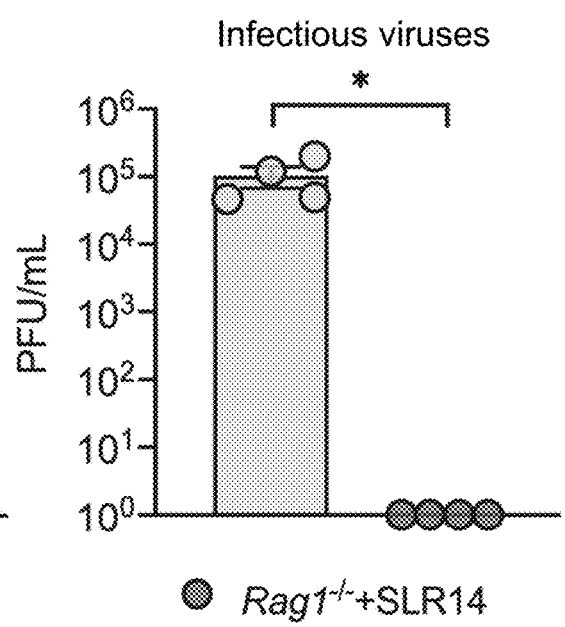

FIGS. 10A-10C illustrate the finding that therapeutic SLR14 clears persistent SARS-CoV-2 infection in Rag1$^{-/-}$ mice. FIG. 10A: Rag1$^{-/-}$ mice were first intratracheally transduced with $10^{11}$ genome copies of AAV9-hACE2, allowed to rest for 14 days, followed by intranasal infection with $10^6$ PFU SARS-CoV-2. 15 µg SLR14 or vehicle were intravenously administered 7 days post infection. Lungs were collected 7 days post SLR14 treatment for assessment of viral load. FIG. 10B: SARS-CoV-2 N gene expression from lung homogenates was measured 14 days post infection by quantitative PCR. FIG. 10C: Infectious viral burden from lung homogenates was measured 14 days post infection by plaque assays. Mean±s.e.m., Student's t-test (b-c); *$P \leq 0.05$, $P \leq 0.01$, *$P \leq 0.001$, ****$P \leq 0.0001$.

Figure 34:
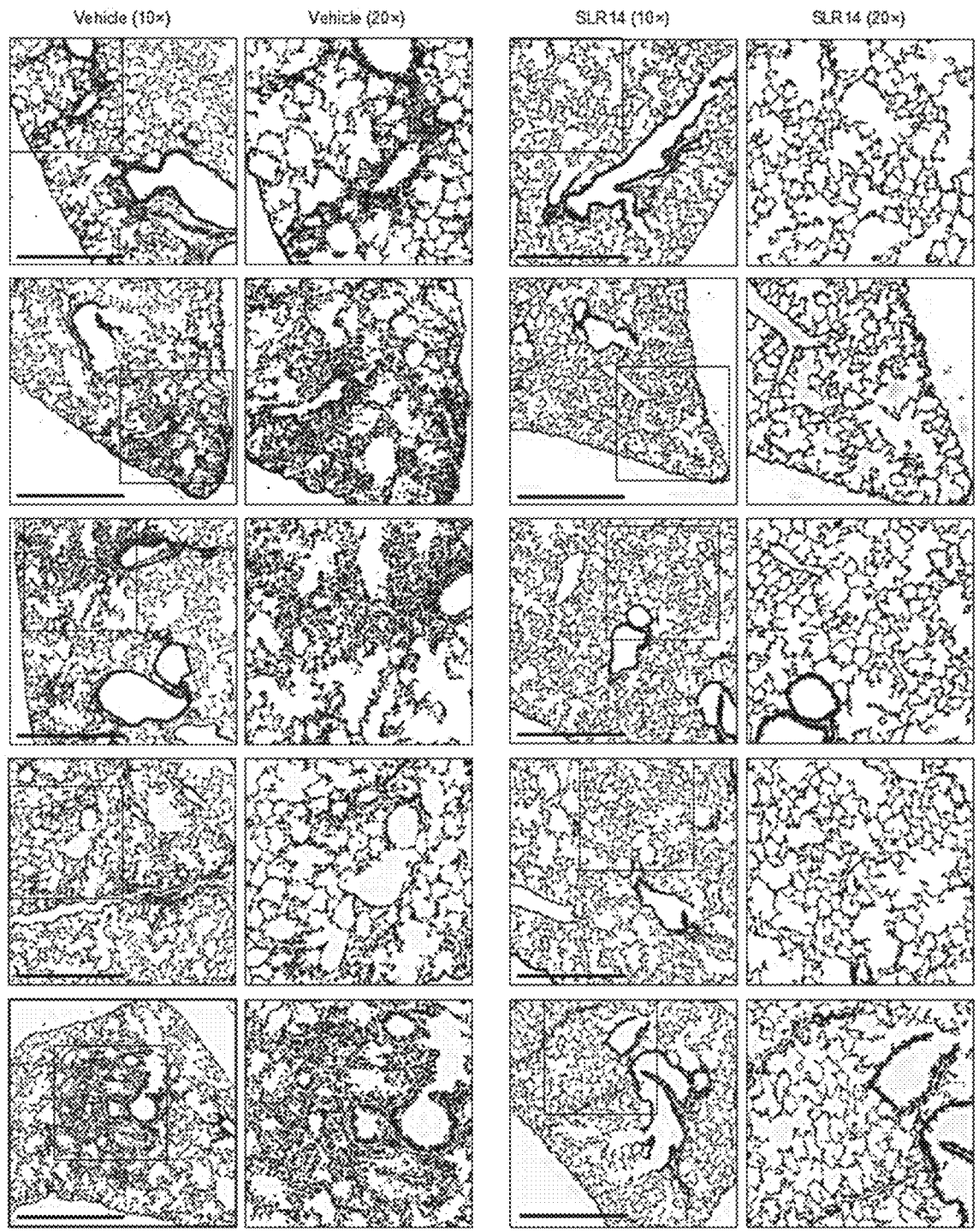
FIG. 34 illustrates the finding that in addition to providing viral control, SLR14 protects lung tissues from SARS-CoV-2 infection-induced viral pneumonia. SARS-CoV-2 infection causes widespread viral pneumonia associated with immune infiltration at alveolar and interstitial locations in lung tissues, which can be prevented by SLR14 treatment.

FIG. 34 illustrates the finding that in addition to providing viral control, SLR14 protects lung tissues from SARS-CoV-2 infection-induced viral pneumonia. SARS-CoV-2 infection causes widespread viral pneumonia associated with immune infiltration at alveolar and interstitial locations in lung tissues, which can be prevented by SLR14 treatment. FIG. 34: H&E staining of lung sections from vehicle- (Left) or SLR14-treated (Right) K18-hACE2 mice 5 DPI. Images show low or high power magnification. Images are representative of n=5 per group. Scale bar, 500 µm.

Figure 12A:
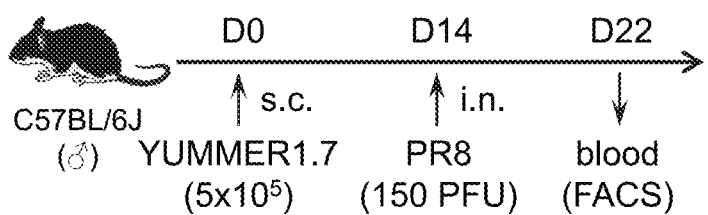
Figure 12B:
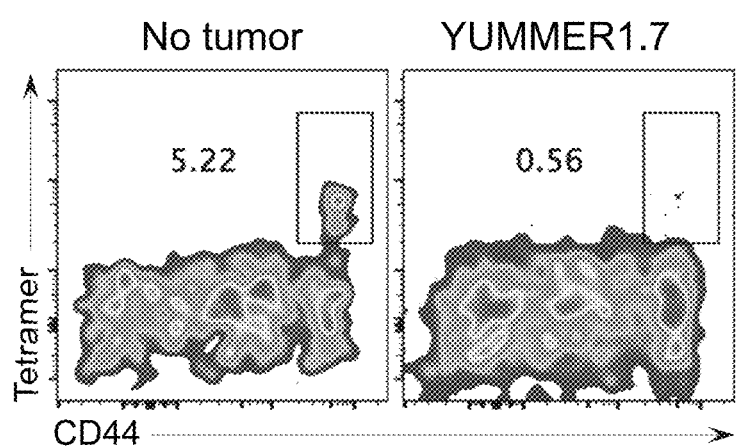
Figure 12C:
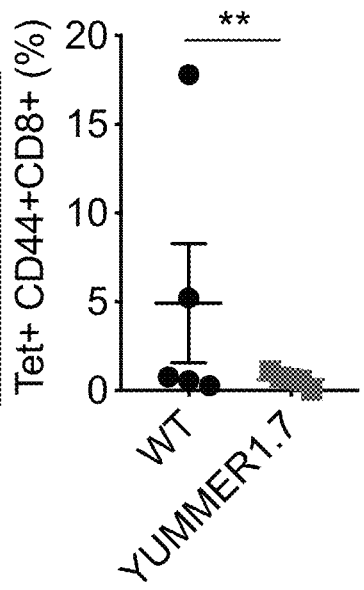
Figure 12D:
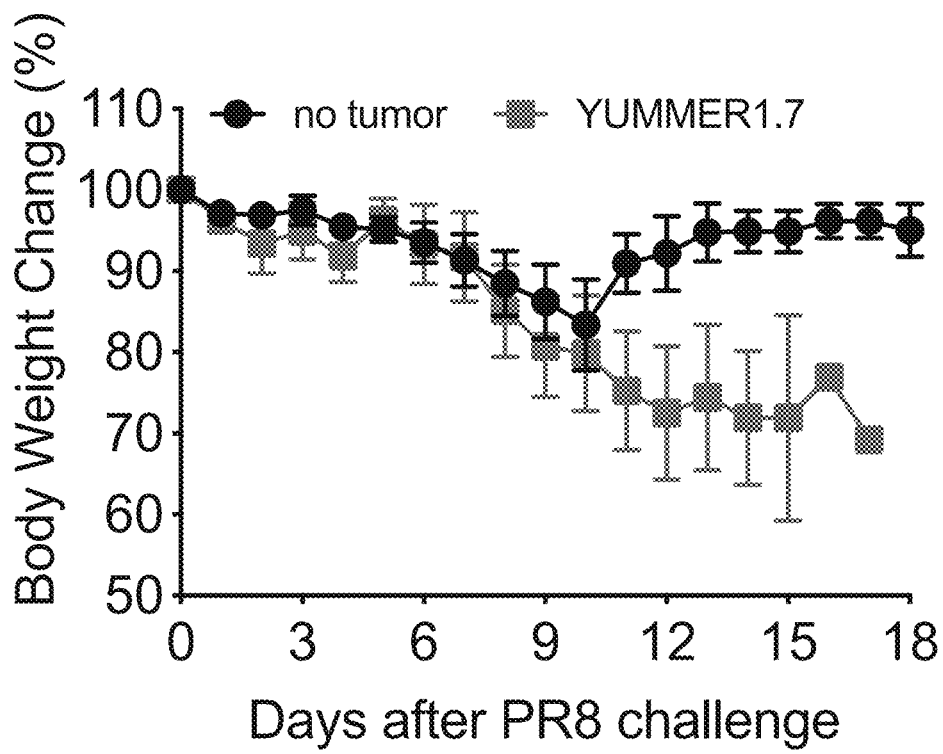
Figure 12E:
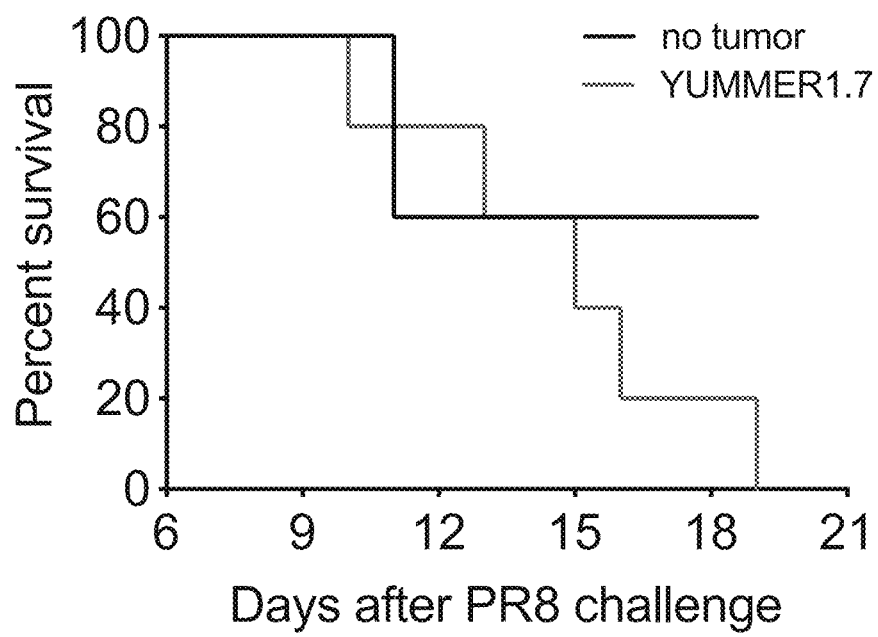

Example 7: Treatment of Viral Infections in Tumor-Bearing Subjects with Small Hairpin RNAs FIGS. 12A-12F illustrate the finding that endogenous Flu-specific CD8+ T cell priming is impaired in tumor-bearing mice. FIG. 12A: Tumor-bearing mice (day 14) or the mice without tumor were intranasally (i.n.) infected with 150 PFU PR8 in 30 µl PBS. PR8-specific CD8+ T cells in the blood at day 8 post infection were measured by using tetramer staining. FIGS. 12B-12C: Percentage of CD44+ CD8+Tetramer+ T cells in the blood at day 8 post infection. FIG. 12D: Body weight change after PR8 infection. FIG. 12E: Survival of the mice after PR8 infection. FIG. 12F: Viral load (shown by the number of plaque) in the lung at day 8 post i.n. infection of 30 k PFU X31-OVA. *: $p < 0.05$. **: $p < 0.01$.

Figure 13A:
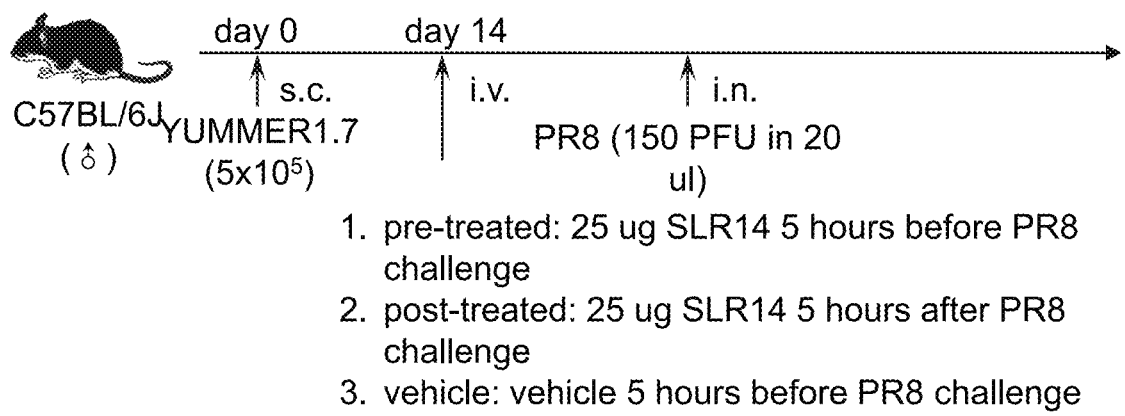
FIGS. 13A-13C illustrate viral load in the lung of tumor-bearing mice after influenza virus i.n. infection. As demonstrated herein, SLR14 pre-treatment protects tumor-bearing mice from influenza virus infection.
Figure 13B:
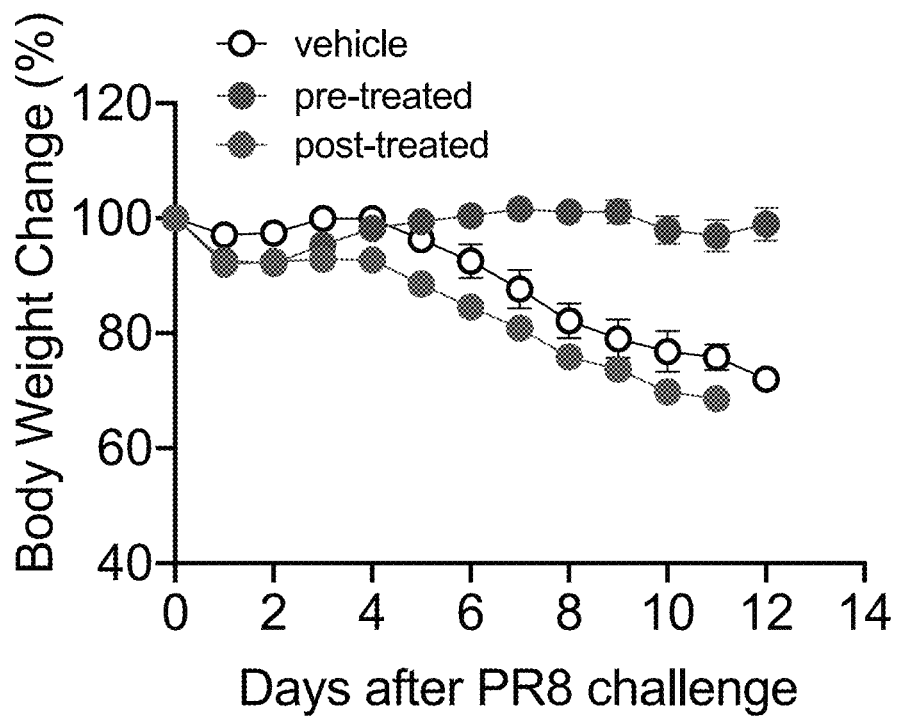
Figure 13C:
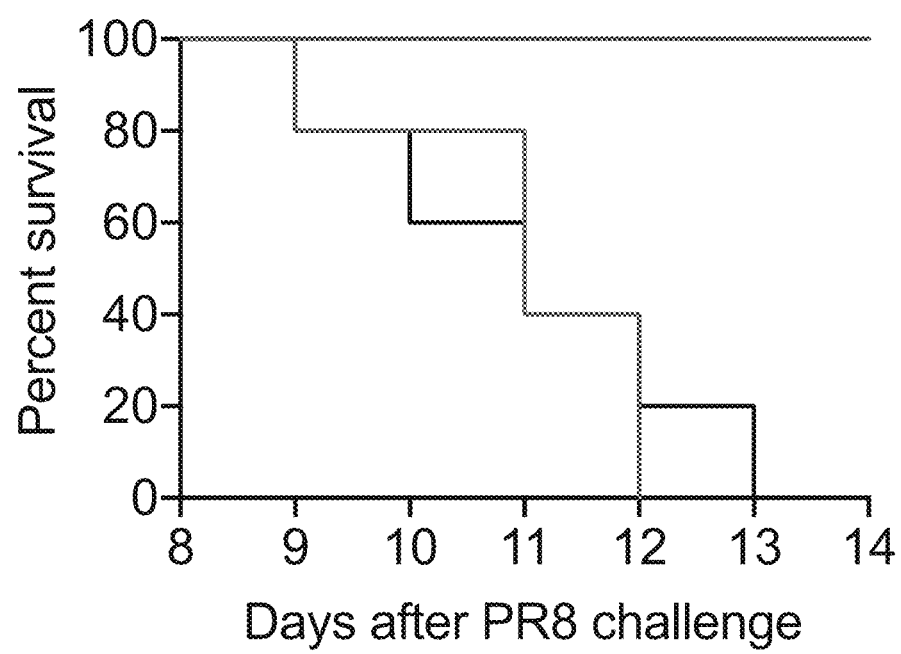

FIGS. 13A-13C illustrate viral load in the lung of tumor-bearing mice after influenza virus i.n. infection. As demonstrated herein, SLR14 pre-treatment protects tumor-bearing mice from influenza virus infection. FIG. 13A: Tumor-bearing mice (day 14) were intravenously (i.v.) treated with 25 µg SLR14 5 hours before or after 150 PFU PR8 intranasal (i.n.) infection. Vehicle-treated mice were used as control. FIG. 13B: Body weight change of the mice after infection. FIG. 13C: Survival of the mice after infection.

Figure 14A:
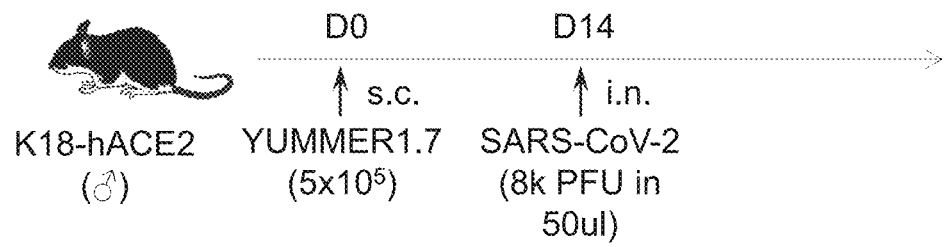
FIGS. 14A-14C illustrate BWL and survival of tumor-bearing mice with SLR14 treatment 5 hours before or after influenza virus i.n. infection. Tumor-bearing mice quickly lose body weight and have a poor survival after SARS-CoV-2 infection.
Figure 14B:
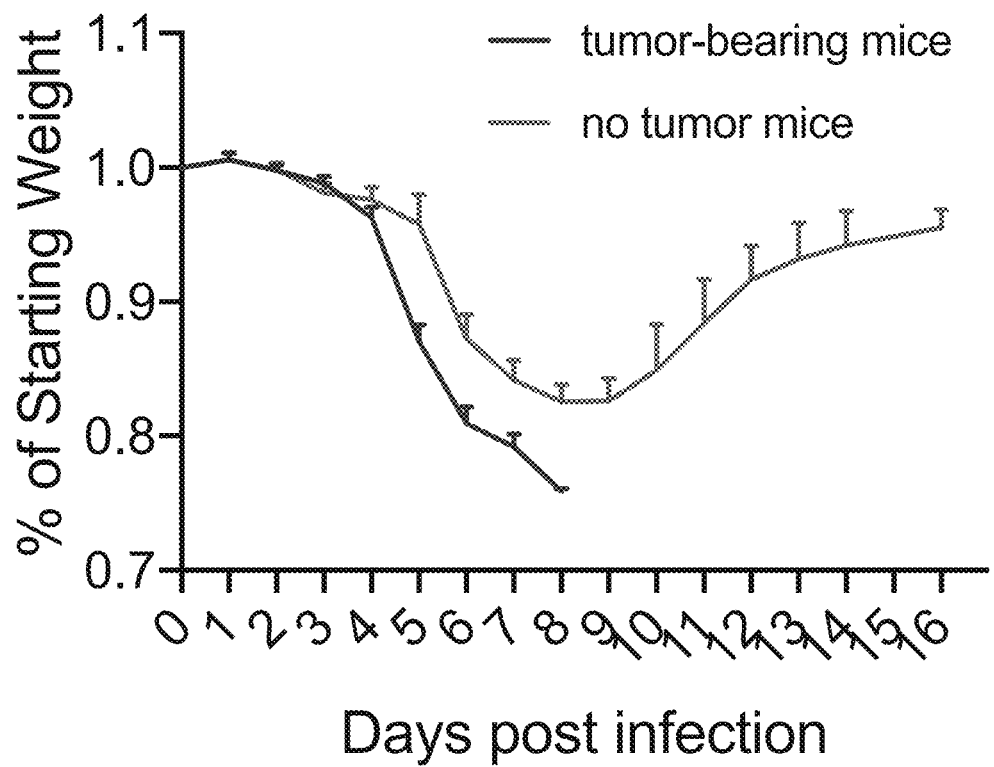
Figure 14C:
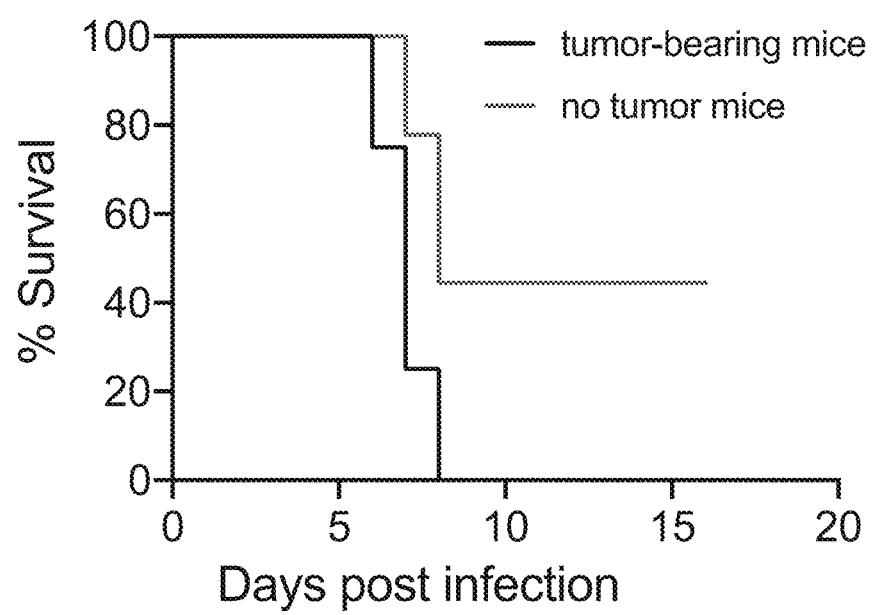

FIGS. 14A-14C illustrate BWL and survival of tumor-bearing mice with SLR14 treatment 5 hours before or after influenza virus i.n. infection. Tumor-bearing mice quickly lose body weight and have a poor survival after SARS-CoV-2 infection. FIG. 14A: Tumor-bearing mice (day 14) were intranasally (i.n.) infected with 8 k PFU SARS-CoV-2 in 50 µl PBS. FIG. 14B: Body weight change of the mice after infection. FIG. 14C: Survival of the mice after infection.

Figure 15A:
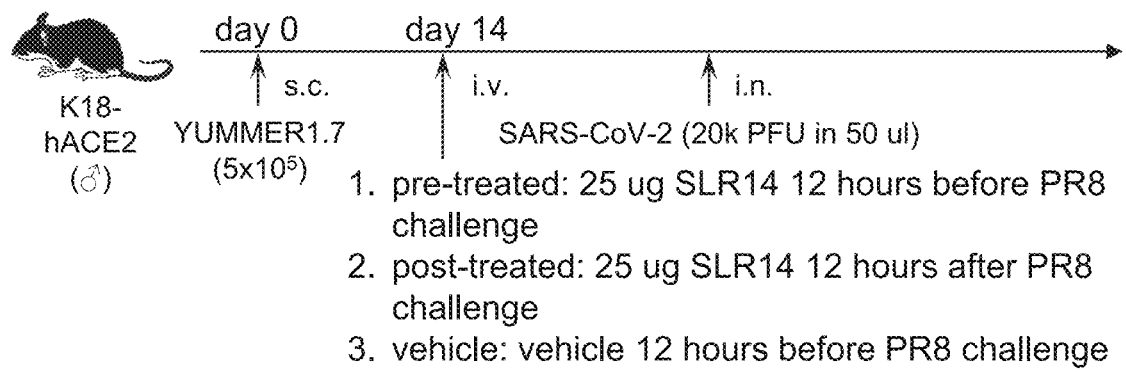
FIGS. 15A-15C illustrate BWL and survival of tumor-bearing mice after SARS-CoV2 i.n. infection. SLR14 pre-treatment protects tumor-bearing mice from SARS-CoV-2 infection.
Figure 15B:
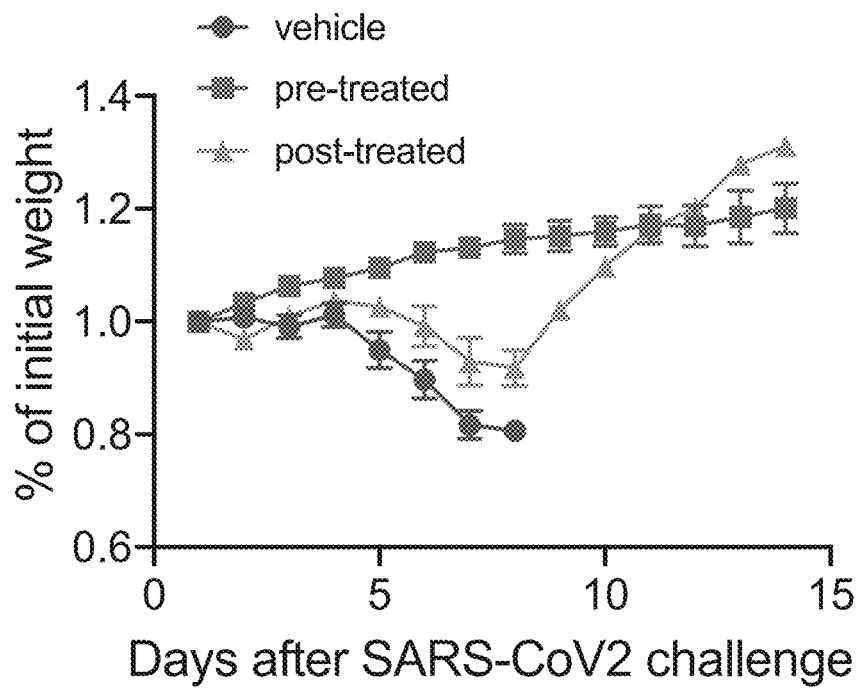
Figure 15C:
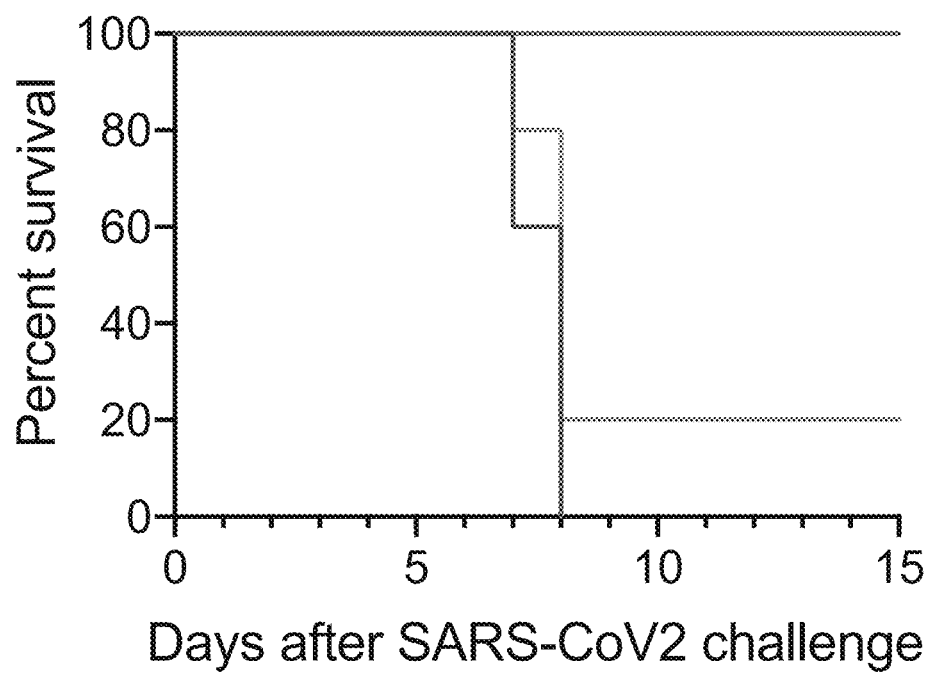

FIGS. 15A-15C illustrate BWL and survival of tumor-bearing mice after SARS-CoV2 i.n. infection. SLR14 pre-treatment protects tumor-bearing mice from SARS-CoV-2 infection. FIG. 15A: Tumor-bearing mice (day 14) were intravenously (i.v.) treated with 25 µg SLR14 12 hours before or after 20 k PFU SARS-CoV-2 intranasal (i.n.) infection. Vehicle-treated mice were used as control. FIG. 15B: Body weight change of the mice after infection. FIG. 15C: Survival of the mice after infection.

Figure 33A:
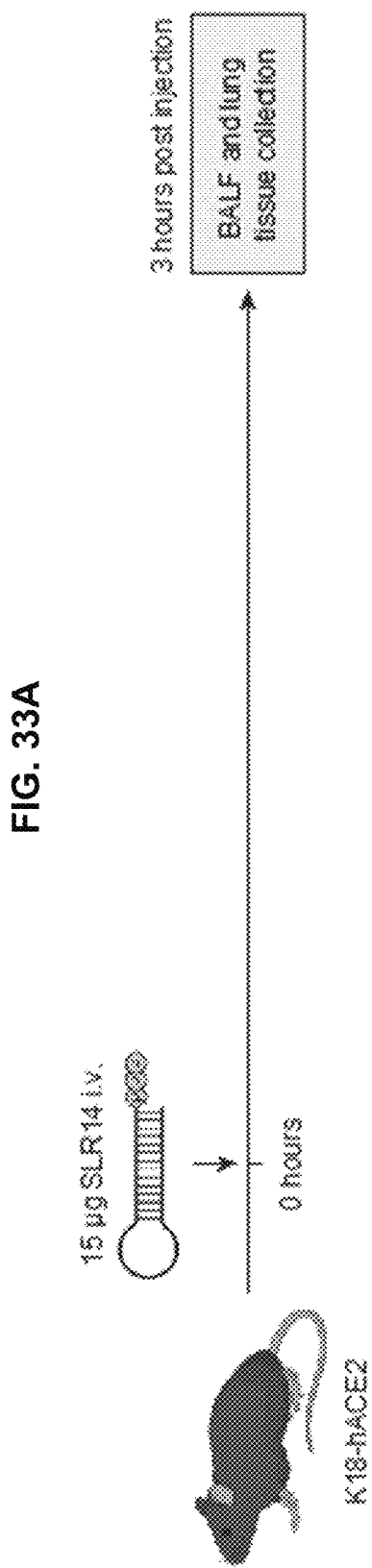
FIGS. 33A-33E illustrate the finding that intravenously delivered SLR14 rapidly induces local IFN-I production at the respiratory mucosa with little impact on IFN-III production.
Figure 33C:
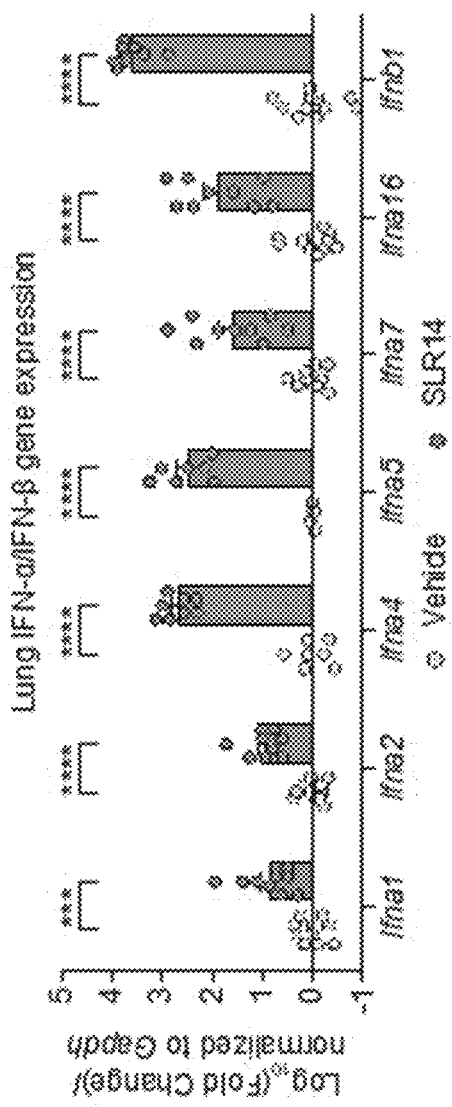
Figure 33B:
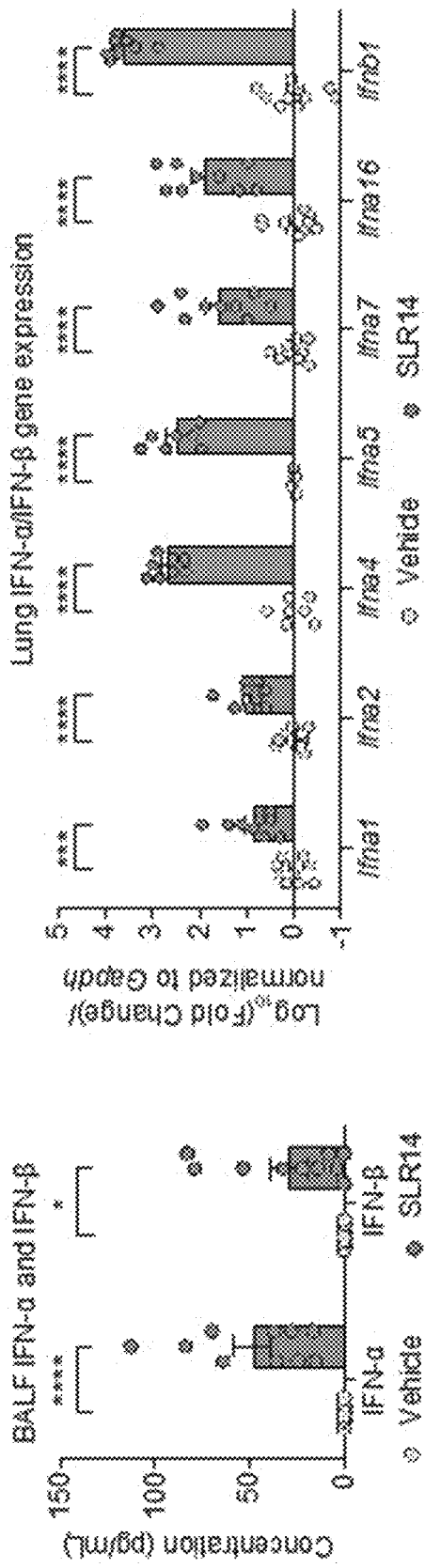
Figure 33E:
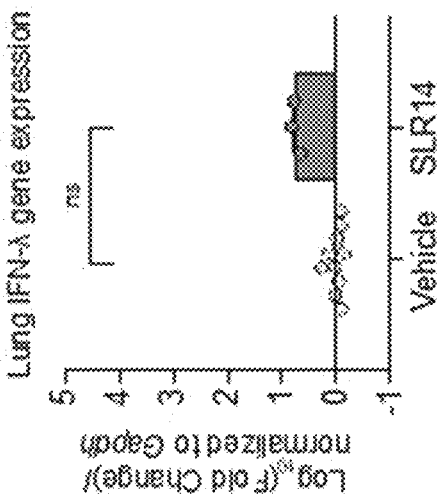
Figure 33D:
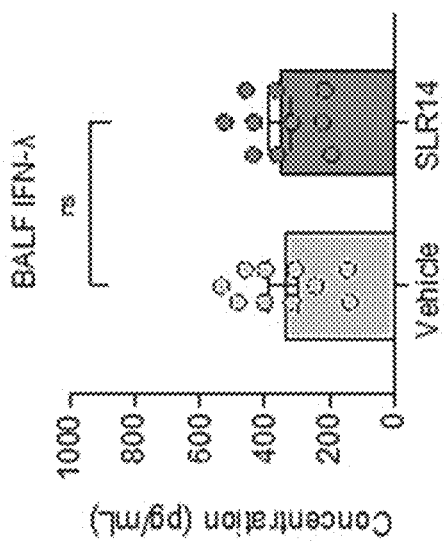

Example 8: SLR14-Mediated Protection Against SARS-CoV-2 Depends on IFN-I Signaling To determine the molecular pathway required for SLR14-mediated respiratory protection against SARS-CoV-2, whether SLR14 affects IFN-I and IFN-III responses in the respiratory tract was investigated (FIG. 33A). Shortly following a single intravenous injection of SLR14, robust levels of IFN-α and IFN-β in the bronchoalveolar lavage fluid (BALF) were detected (FIG. 33B). Consistently, substantially elevated expression levels of multiple IFN-I genes, including Ifna1, Ifna2, Ifna4, Ifna5, Ifna7, Ifna16, and Ifnb1, in lung tissues of SLR14-treated mice were found (FIG. 33C). In contrast, no induction of BALF IFN-III compared to vehicle controls by ELISA and only a mild elevation of Ifnl2,3 gene expression in the lung from SLR14-treated mice was found (FIGS. 33D-33E). These results demonstrate that in addition to systemic IFN-I responses, intravenously delivered SLR14 rapidly induces local IFN-I production at the respiratory mucosa.

Figure 17A:
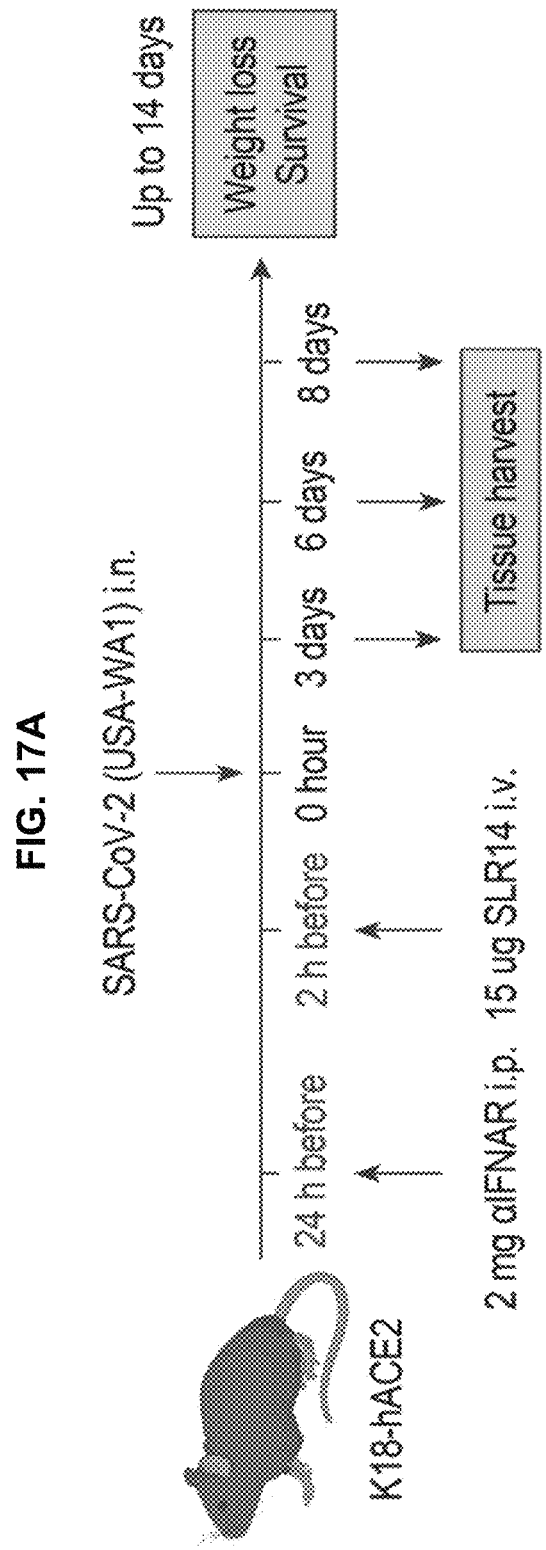
Figure 17B:
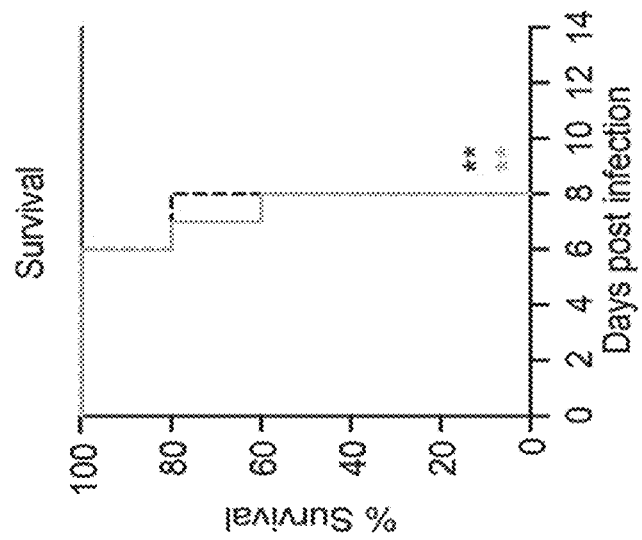
Figure 17C:
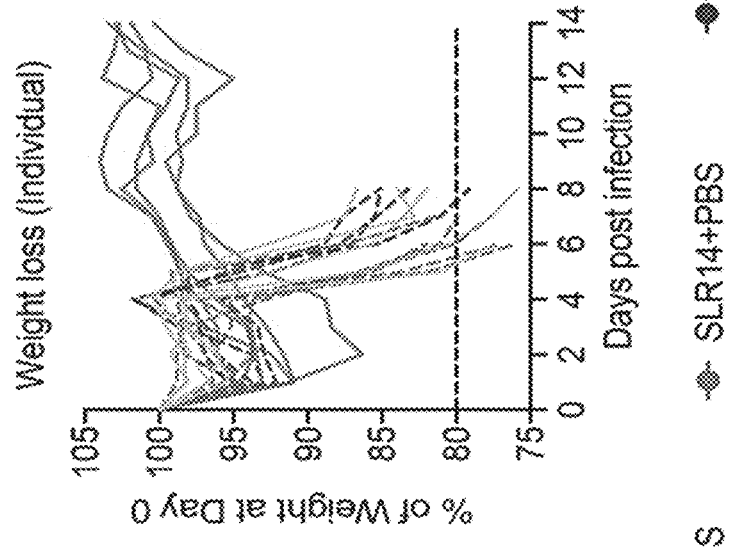
Figure 17D:
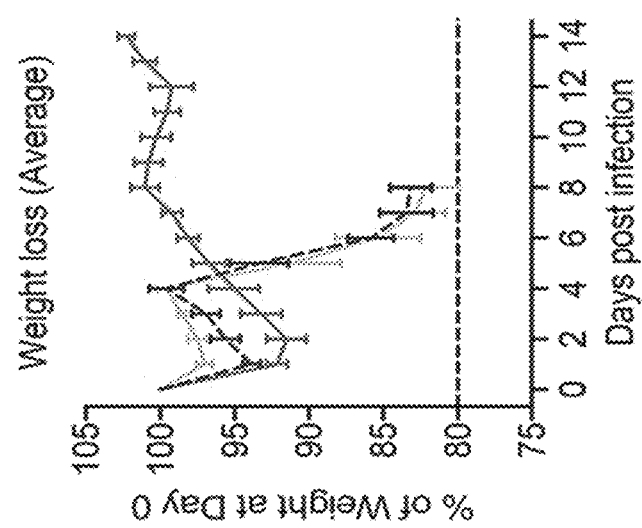

To determine the molecular pathway required for SLR14-mediated protection against SARS-CoV-2, the effect of IFN-I signaling blockade was investigated using neutralizing antibodies against the receptor for IFN-I, interferon-α/β receptor (IFNAR) (FIG. 17A). Similar to SLR14 treatment at 4 hours post infection, K18-hACE2 mice were completely protected from morbidity and mortality when treated with SLR14 2 hours prior to SARS-CoV-2 infection. However, mice that were additionally pre-treated with anti-IFNAR antibodies lost the protection provided by SLR14 and all succumbed to the infection by 8 DPI (FIGS. 17B-17D). These results indicated that SLR14-mediated disease protection depends on IFN-I signaling.

Viral infections of the lower respiratory tract are a leading cause of mortality in this disease context, whereas upper respiratory infection primarily contributes to viral transmission. To characterize the tissue sites that are protected by SLR14 and the contribution of IFN-I signaling to SLR14-mediated protection, the lung parenchyma, the trachea, and a nasal wash were collected to assess viral burden throughout the respiratory tract at 3, 6, and 8 DPI. The ability of SLR14 to suppress lung viral replication was prominent as early as 3 DPI and maintained throughout the course of infection up to 8 DPI. However, the reduction in the level of viral genomic RNA in lung tissues was completely abolished when mice were also pre-treated with anti-IFNAR antibodies (FIGS. 17E-17G). These findings were largely recapitulated in the trachea, although the overall viral titer was lower than that of the lung (FIGS. 17H-17J). A significant decrease in the level of genomic RNA was also observed in nasal washes from SLR14-treated mice at 8 DPI, although not at 3 or 6 DPI (FIGS. 21A-21D). The lack of an apparent early antiviral effect in the nasal cavity highlights the spatial compartmentalization of the respiratory mucosa and suggests intranasal SLR14 application as an alternative route of delivery to achieve optimal protection in the upper respiratory tract. These results indicated that SLR14 utilizes IFN-I signaling to mediate viral clearance in the lower respiratory tract, thereby preventing severe respiratory disease.

Figure 22A:
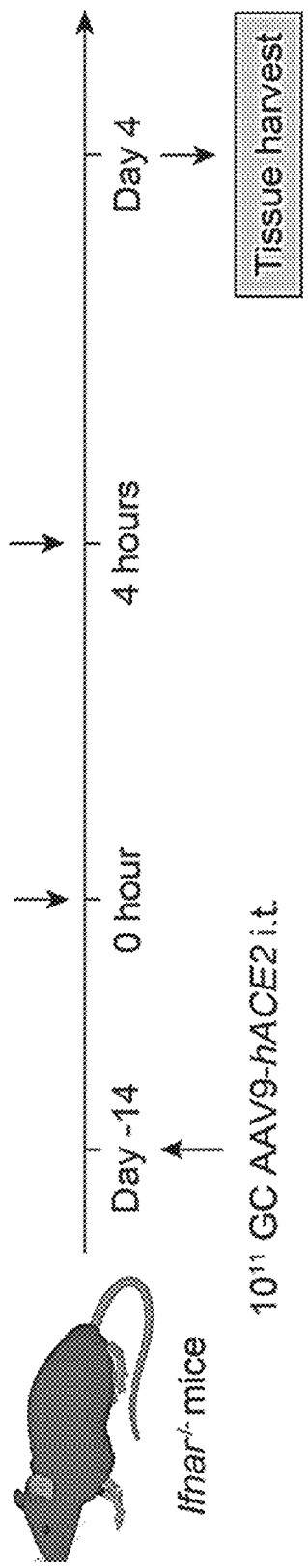
FIGS. 22A-22B illustrate the finding that genetic Ifnar deficiency abrogates SLR14-mediated antiviral activity.
Figure 22B:
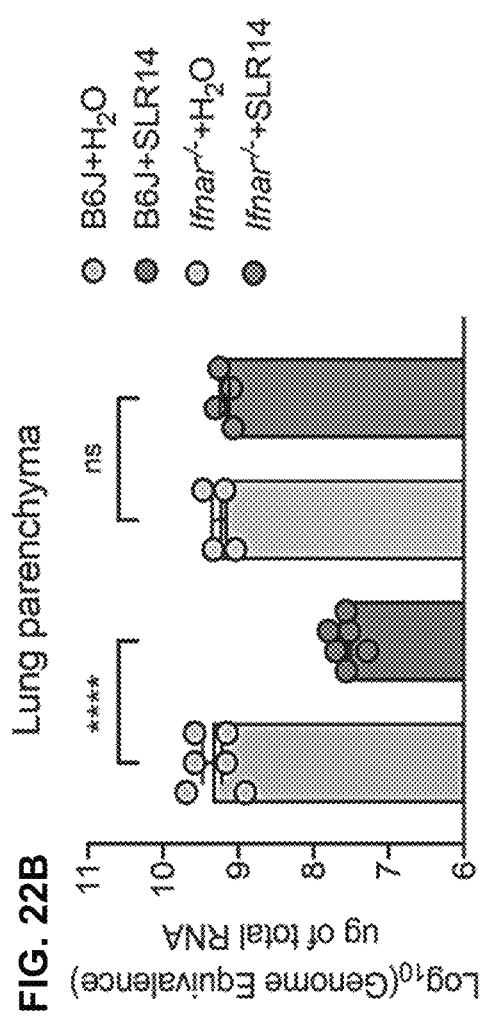

The role of IFN-I signaling in SLR14-mediated viral control was additionally assessed using IFNAR-deficient (Ifnar$^{-/-}$) mice. Laboratory mice are not susceptible to SARS-CoV-2 infection due to the inability of the virus to utilize the mouse orthologue of human ACE2 for viral entry. Therefore, C57BL/6J (B6J) or Ifnar$^{-/-}$ mice was first transduced with hACE2-expressing adeno-associated viruses (AAV-hACE2) through intratracheal delivery to sensitize them for SARS-CoV-2 infection (FIG. 22A). Two weeks post transduction, AAV-hACE2 B6J or Ifnar$^{-/-}$ mice were infected with SARS-CoV-2 and treated with SLR14 4 hours post infection. Consistent with experiments using anti-IF-NAR antibodies, AAV-hACE2 Ifnar$^{-/-}$ mice did not respond to SLR14 and maintained high levels of viral genomic RNA similar to that of untreated controls 4 DPI (FIG. 22B). In contrast, SLR14-treated AAV-hACE2 B6J mice had significantly reduced level of genomic RNA compared to untreated controls. Together, these results showed, by two separate approaches, that the SLR14-mediated antiviral resistance against SARS-CoV-2 requires IFNAR.

FIGS. 33A-33E illustrate the finding that intravenously delivered SLR14 rapidly induces local IFN-I production at the respiratory mucosa with little impact on IFN-III production. FIG. 33A: Experimental scheme: K18-hACE2 mice were intravenously administered with 15 μg SLR14 or vehicle. 3 hours post injection, BALF and lung tissues were collected for IFN ELISA and RT-qPCR. FIGS. 33B-33C: Measurement of IFN-I secretion in the BAL fluid by ELISA and various Ifna and Ifnb gene expression in the lung tissue by RT-qPCR from vehicle or SLR14 treated mice. FIGS. 33D-33E: Measurement of IFN-III secretion in the BAL fluid by ELISA and Ifnl gene expression in the lung tissue by RT-qPCR from vehicle or SLR14 treated mice. Mean s.e.m.; Statistical significance was calculated by two-way ANOVA followed by Bonferroni correction (FIGS. 33B-33C) or Student's t-test (FIGS. 33D-33E); *P≤0.05, P≤0.01, *P≤0.001, ****P≤0.0001. Data are pooled from or representative of two independent experiments.

Figure 37:
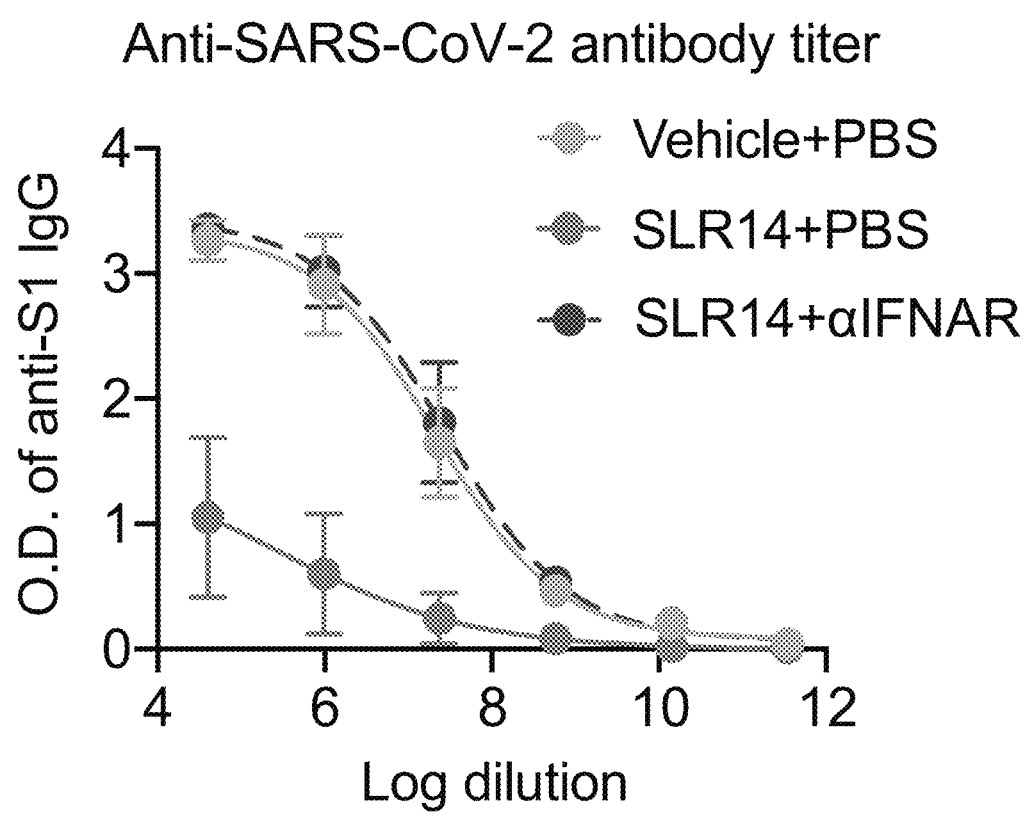
FIG. 37 illustrates the finding that SLR14 utilizes IFN-I signaling to suppress SARS-CoV-2 replication, which is evidenced by dramatically reduced titers of spike-specific antibodies developed in SLR14-treated mice. K18-hACE2 mice were intranasally infected with a sublethal dose of SARS-CoV-2. 2 hours before infection, 15 µg SLR14 or vehicle were intravenously administered. 24 hours before SLR14 injection, half of SLR14-treated mice was additionally given 2 mg anti-IFNAR antibodies. Sera were then collected from survivor mice 14 DPI and used for anti-SARS-CoV-2 S1 IgG measurement by ELISA. Mean±s.e.m.; Data are pooled from two independent experiments.

FIG. 37 illustrates the finding that SLR14 utilizes IFN-I signaling to suppress SARS-CoV-2 replication, which is evidenced by dramatically reduced titers of spike-specific antibodies developed in SLR14-treated mice. K18-hACE2 mice were intranasally infected with a sublethal dose of SARS-CoV-2. 2 hours before infection, 15 μg SLR14 or vehicle were intravenously administered. 24 hours before SLR14 injection, half of SLR14-treated mice was additionally given 2 mg anti-IFNAR antibodies. Sera were then collected from survivor mice 14 DPI and used for anti-SARS-CoV-2 S1 IgG measurement by ELISA. Mean±s.e.m.; Data are pooled from two independent experiments.

Example 9: SLR14 is Taken Up by Various Cell Types in the Lung

Figure 23C:
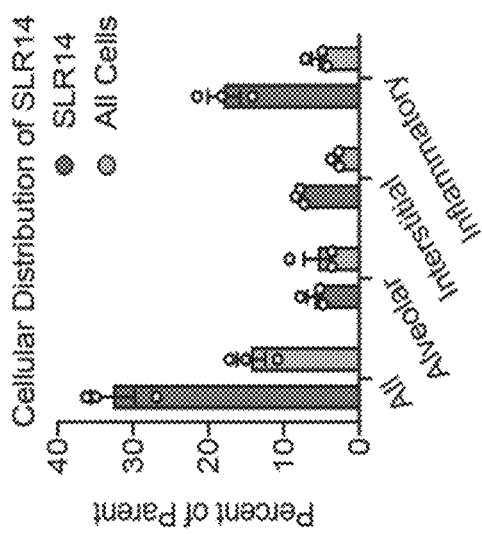
Figure 23E:
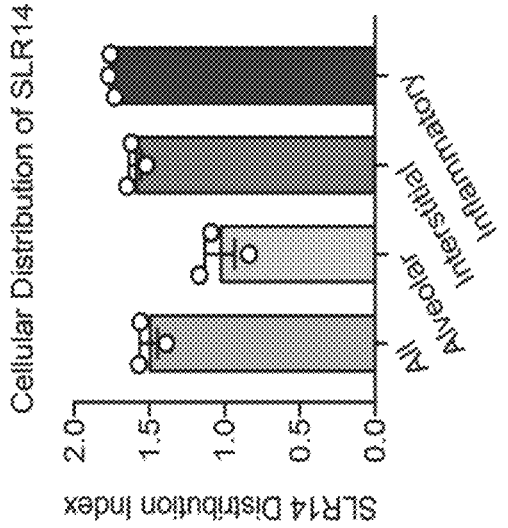
Figure 23B:
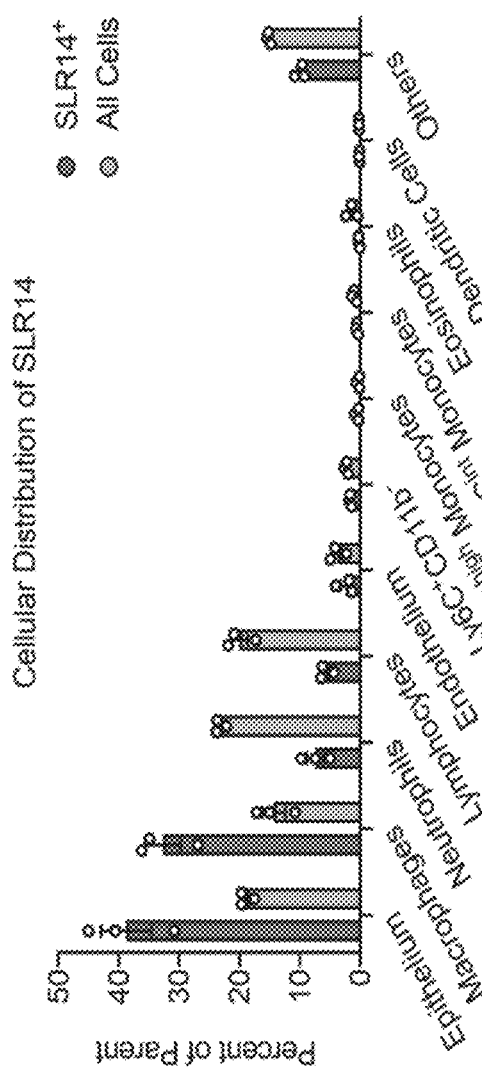
Figure 23D:
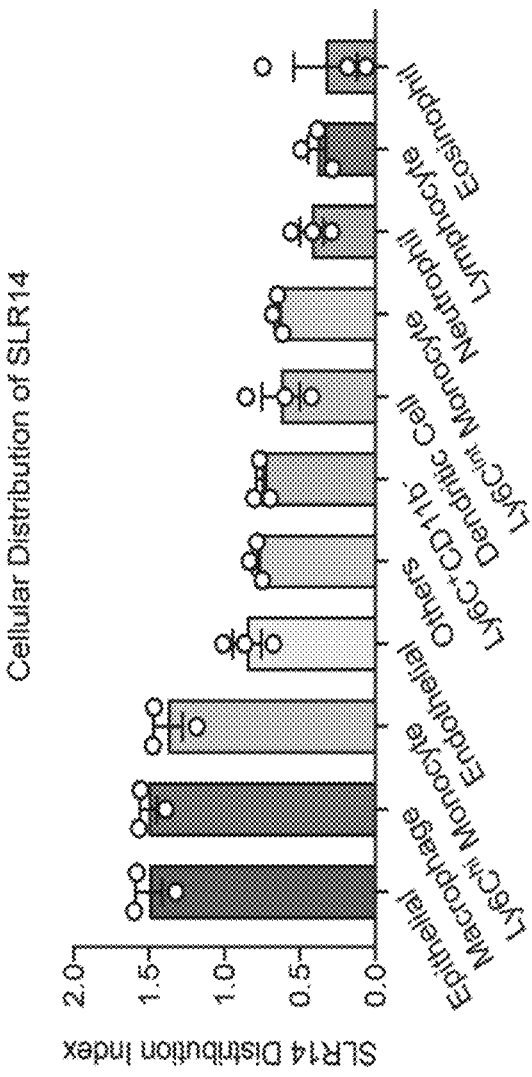

RIG-I is ubiquitously expressed in all cell types. To determine the cell type that is being targeted by PEI-complexed SLR14 following i.v. injection and responsible for producing an early source of IFN-I to mediate protection, Alexa Flour 647 (AF647)-conjugated SLR14 was injected into naïve K18-hACE2 mice, and lung tissues collected 4 hours post injection to assess cellular uptake of SLR14 by flow cytometry (FIG. 23A). Of the total SLR14$^+$ cells, SLR14 was found to be broadly distributed across multiple immune and non-immune cellular compartments (FIG. 23B). In particular, EpCAM$^+$ epithelial cells and CD64$^+$ macrophages accounted for the majority of SLR14 uptake (~70% of SLR14$^+$ cells). The composition of SLR14$^+$ macrophages was further analyzed and this population was found to be mainly CD11b$^+$Ly6C$^+$ monocyte-derived proinflammatory macrophages, although some SLR14$^+$ interstitial and alveolar macrophages were also found (FIG. 23C). A distribution index was additionally derived to account for cell type abundance and observed similar patterns of SLR14 uptake by epithelial cells and macrophages (FIGS. 23D-23E). Together, these results indicated that i.v. injected SLR14 is mainly taken up by lung epithelial cells and inflammatory macrophages, contributing to the rapid production of IFN-I and elicitation of local ISG response against SARS-CoV-2 infection.

Figure 18A:
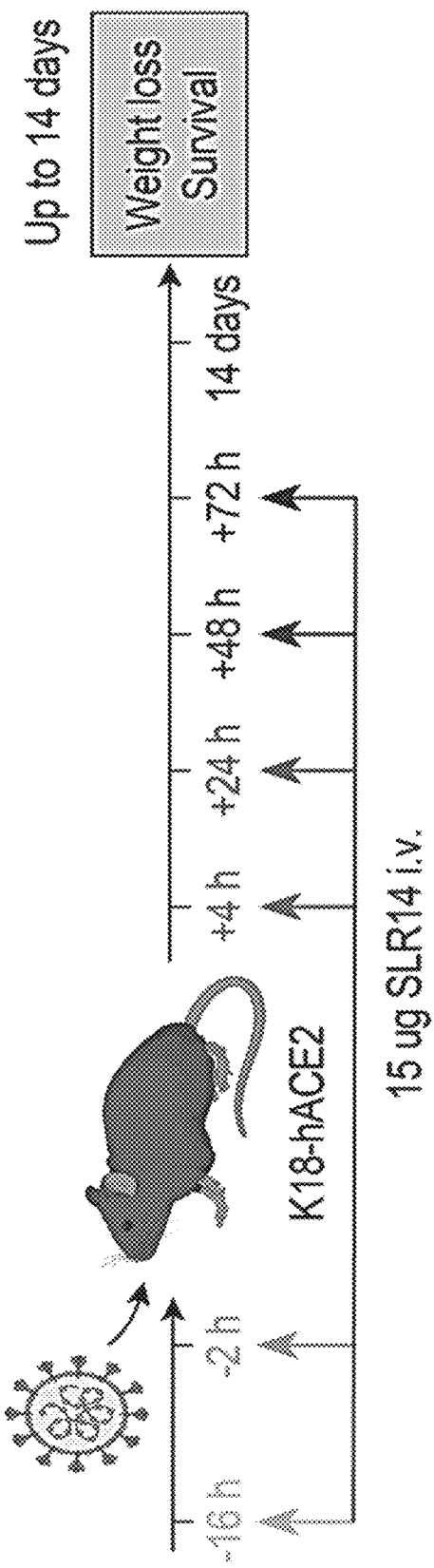
Figures 18E, 18F, 18G:
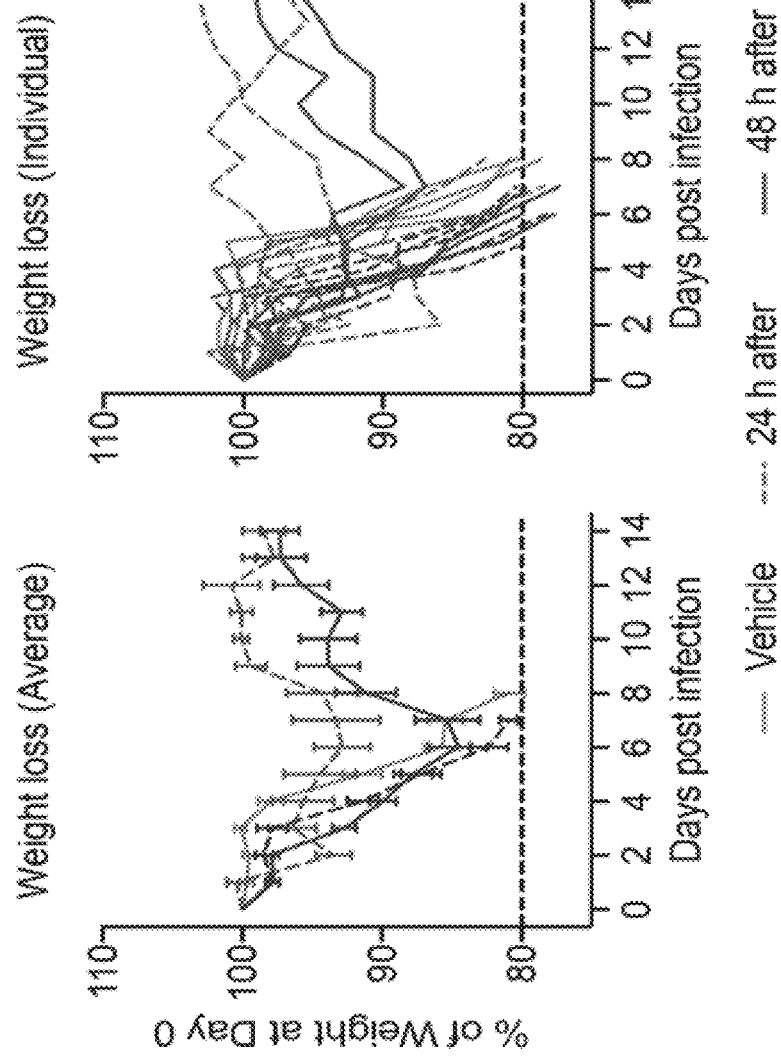

Example 10: SLR14 Treatment Timing Relative to SARS-CoV-2 Infection Determines Protective Activities Early and robust IFN-I production in response to infection with SARS-CoV-2 is essential for rapid control of viral replication, whereas IFN-I induced late during the infection may contribute to immunopathology and drive severe disease. Thus, the effect of treatment timing on the protective capacity of SLR14 was next examined. K18-hACE2 mice were treated with SLR14 at different timepoints relative to SARS-CoV-2 challenge (FIG. 18A). Prophylactic treatment of SLR14 either at 16 or 2 hours before infection protected mice from weight loss and clinical disease after SARS-CoV-2 infection (FIGS. 18B-18D). Similarly, treatment of SLR14 4 hours after infection as a post-exposure prophylaxis was also highly protective and largely prevented disease development. However, the efficacy of SLR14 became more dependent on treatment timing when administered therapeutically. Treatment at 24 or 48 hours post infection resulted in an intermediate level of protection (40% survival) with some level of morbidity and mortality being observed, while SLR14 lost its protective capacity when administered 72 hours post infection (FIGS. 18E-18G). These results corroborated the protective role of early IFN-I, and importantly, demonstrated that SLR14-based treatment can be broadly used as prophylaxis and early post-exposure prophylaxis against COVID-19.

Example 11: Therapeutic SLR14 Cures Persistent SARS-CoV-2 Infection in Immunodeficient Mice Through Induction of IFN-I There is a clinically unmet need for the development of an effective therapy to treat chronic SARS-CoV-2 infection in immunodeficient individuals and prevent further emergence of viral variants. AAV-hACE2-transduced Rag1$^{-/-}$ or Rag2$^{-/-}$ mice (which completely lack mature T and B cells, collectively referred to as Rag$^{-/-}$ mice) become chronically infected following SARS-CoV-2 infection, similar to what is seen in immunodeficient patients. These mice maintain stable levels of viral RNA and infectious virus for at least 14 DPI. This is in stark contrast to B6J mice, which clear the infection by 7 DPI and remain virus free thereafter. Given that convalescent plasma (CP) therapy has been implemented to treat immunocompromised patients with COVID-19, it was first validated whether persistently infected Rag$^{-/-}$ mice are a clinically relevant model in their response to CP therapy. To this end, sera were adoptively transferred from convalescent AAV-hACE2 B6J mice into persistently infected recipient AAV-hACE2 Rag$^{-/-}$ mice 7 DPI and measured lung viral titer 14 DPI (FIG. 24A). CP transfer resulted in significant reduction in genomic RNA and complete clearance of infectious virus in the lung, compared with PBS-treated SARS-CoV-2 infected AAV-hACE2 Rag$^{-/-}$ controls (FIGS. 24B-24C). These results indicate that Rag$^{-/-}$ mice is a suitable in vivo model of immunocompromised patients for preclinical testing of antiviral therapeutics, as they support persistent SARS-CoV-2 infection and derive benefits from CP therapy.

It was next examined whether SLR14 can be used as a therapeutic modality to treat persistent infection in Rag$^{-/-}$ mice. AAV-hACE2 Rag$^{-/-}$ mice were infected with SARS-CoV-2, treated with SLR14 7 DPI, and lung tissues collected 14 DPI to assess the viral burden (FIG. 19A). 1 day prior to SLR14 treatment, a subset of SLR14-treated AAV-hACE2 mice also received anti-IFNAR antibodies. SLR14 treatment led to a significant reduction in the level of genomic viral RNA in the lung (FIG. 19B). The ability of SLR14 in decreasing viral RNA was abolished when anti-IFNAR blocking antibody was given, suggesting SLR14 similarly utilizes IFN-I signaling to promote viral clearance in mice lacking the adaptive immune system. A striking difference was also observed in the infectious viral load in lung tissues from SLR14-treated mice compared to vehicle controls. Treatment with SLR14, but not vehicle, significantly reduced viral burden and resulted in complete clearance of infectious virus in 5 out of 7 AAV-hACE2 Rag$^{-/-}$ mice and reduction of viral titer in the remaining 2 (FIG. 19C). Moreover, SLR14-mediated protection required IFNAR signaling (FIG. 19C). These results showed that in the setting of complete T- and B-cell-deficiency, a single therapeutic SLR14 treatment, through the induction of IFN-I, is sufficient to cure persistent infection.

Figure 25:
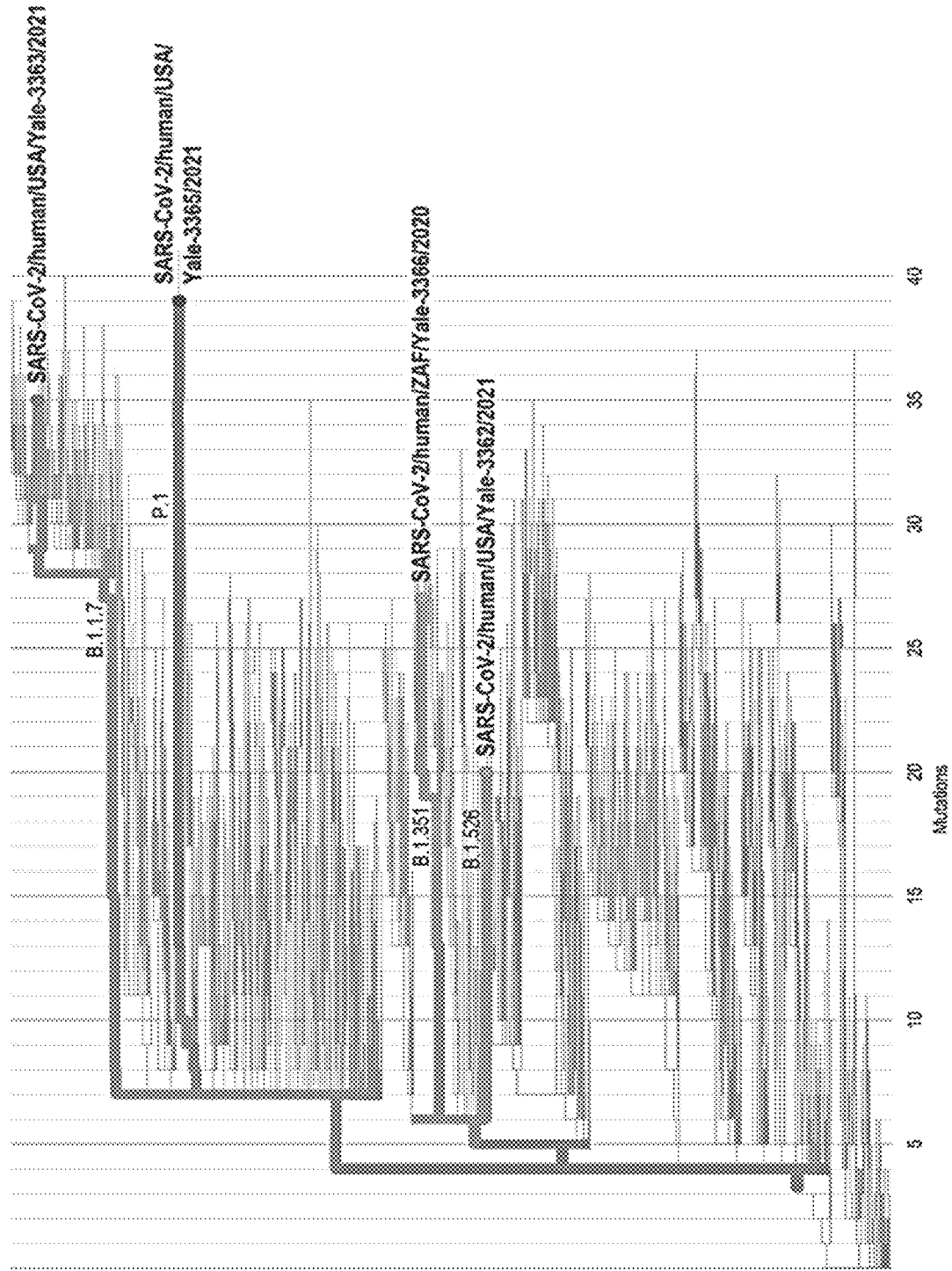
FIG. 25 illustrates maximum likelihood phylogeny SARS-CoV-2 genomes and the cultured viruses used in this study. NextClade (clades dot nextstrain dot org/) was used to generate a phylogenetic tree to show the evolutionary relations between the four cultured viruses and other SARS-CoV-2 lineages. Branches are colored by Nextstrain clade, with branch labels indicating the Pango lineages, and highlighted are the four cultured viruses used in this study.

Example 12: SLR14 Affords Broad Protection Against Immunologically Evasive SARS-CoV-2 Variants As SARS-CoV-2 variants continue to emerge and spread, antiviral therapeutics that confer broadly cross-reactive protection are urgently needed. Emerging evidence suggests that several SARS-CoV-2 variants have acquired mutations that confer elevated resistance to IFN-I treatment in cell culture. However, whether such altered properties in vitro translate into evasion of IFN-based therapy in vivo remains unclear. To this end, 4 clinically relevant SARS-CoV-2 VOC, including P.1, B.1.526, B.1.1.7, and B.1.351, were obtained and used to infect K18-hACE2 mice. The P.1, B.1.526, and B.1.1.7 variants were identified and isolated as part of the Yale SARS-CoV-2 Genomic Surveillance Initiatives, and the B.1.351 variant was obtained from BEI Resources Repository. All variants were confirmed to harbor signature mutations characteristic of their respective lineages and show correct placement in the phylogenetic tree built with public SARS-CoV-2 genomic sequences (Table 1, FIG. 25).

Figure 36A:
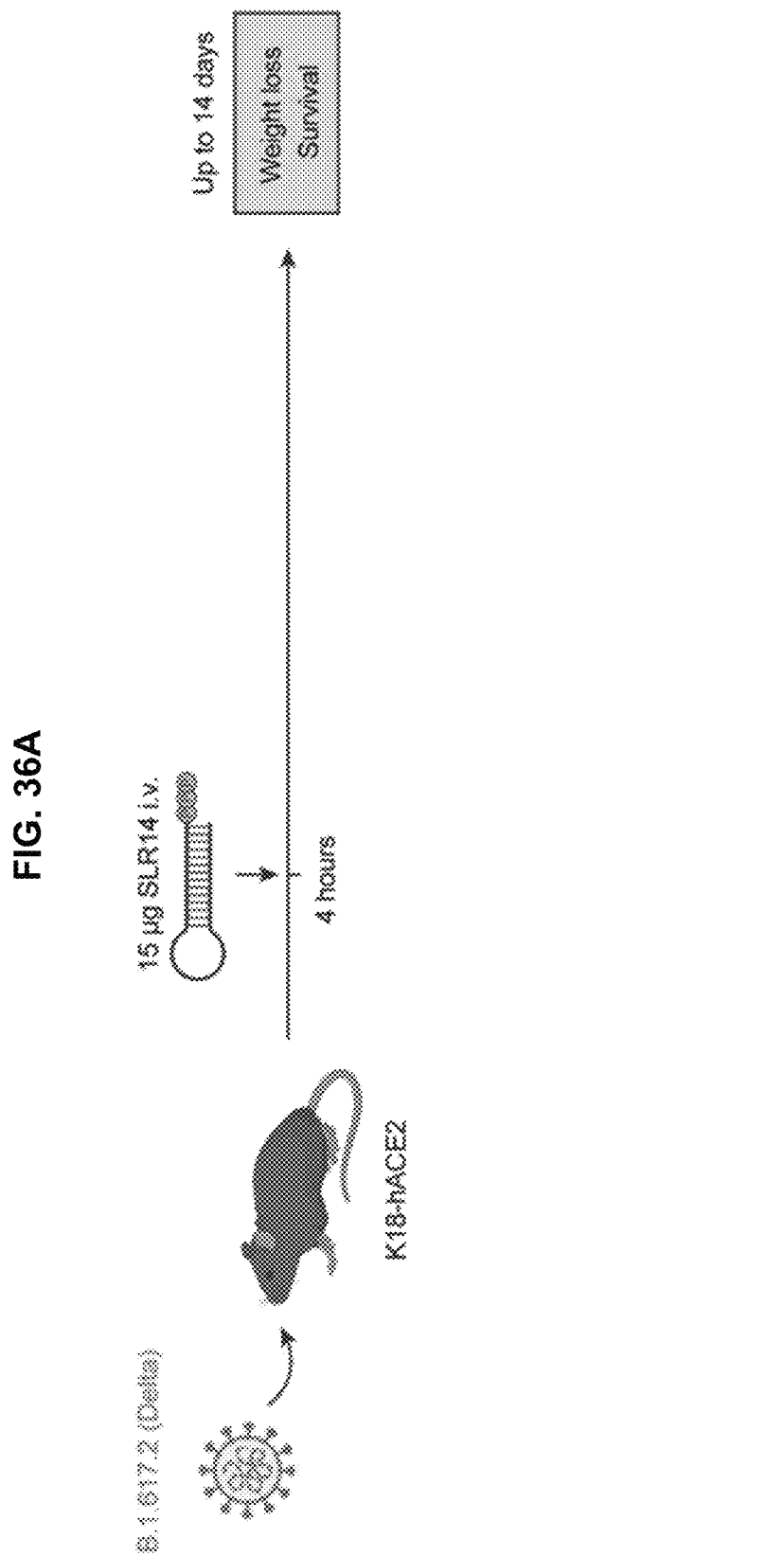

To examine whether SLR14 is protective against SARS-CoV-2 VOC, mice were infected with variants P.1, B.1.351, B.1.526, B.1.617.2, or B.1.1.7, and treated with SLR14 4 hours post infection (FIG. 20A). SLR14 afforded potent protection against the P.1 variant, almost completely preventing morbidity and mortality in the face of highly pathogenic infection, even when treated post-exposure prophylactically (FIGS. 20B-20D). Similarly, SLR14 fully prevented weight loss or any discernable disease following infection with B.1.526, which, in untreated mice, caused a less pathogenic infection compared to that of the ancestral strain or circulating variants (FIGS. 20E-20G). In addition, it was found that SLR14 was highly effective against B.1.617.2, protecting against weight loss in K18-hACE2 mice infected with a relatively low dose of virus (FIGS. 36B-36D). In contrast, vehicle-treated mice uniformly lost 10 to 20% of their starting body weight. Remarkably, even in the face of a high-dose infection, SLR14-treated mice were protected from clinical disease or death, whereas vehicle controls rapidly succumbed to the infection (FIGS. 36E-36G). Consistent with the reported resistance to IFN-I signaling in vitro, SLR14 treatment was less effective against infection with B.1.351 or B.1.1.7 in vivo, conferring approximately 40 to 50% net protection in K18-hACE2 mice (60% survival in SLR14-treated mice over 10 to 20% survival in vehicle controls) (FIGS. 20H-20M). Additional experiments with the B.1.1.7 variant confirmed its partial resistance to SLR14 treatment, irrespective of initial sizes of viral inoculum (FIGS. 26A-26F). Nevertheless, clear benefits were seen with prophylactic treatment of SLR14. These results indicate that SLR14 confers broad-coverage protection against antibody- and IFN-I-evasive variants.

Example 13

Figure 28A:
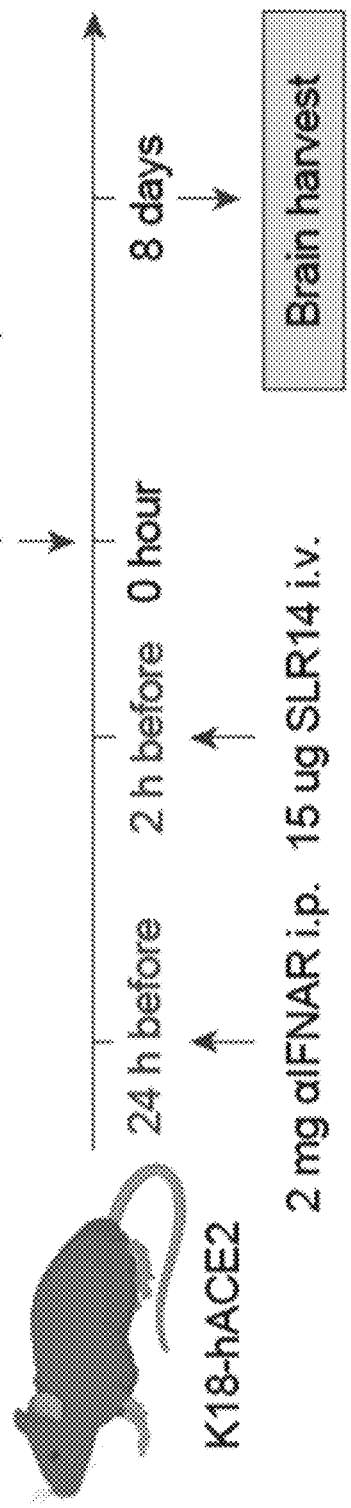
FIGS. 28A-28B illustrate the finding that SLR14 pretreatment protects K18-hACE2 mice from SARS-CoV-2 brain infection.
Figure 28B:
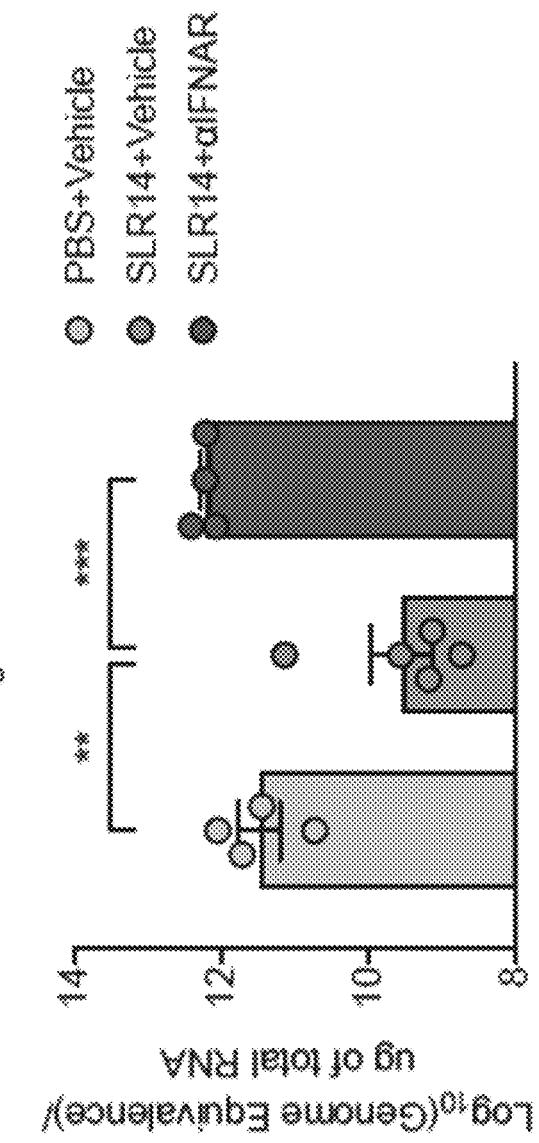

FIGS. 28A-28B illustrate the finding that SLR14 pretreatment protects K18-hACE2 mice from SARS-CoV-2 brain infection. FIG. 28A: Experimental scheme: K18-hACE2 mice were intranasally infected with $10^3$ PFU SARS-CoV-2 (2019n-CoV/USA_WA1/2020). 2 hours before infection, 15 µg SLR14 or vehicle were intravenously administered. 24 hours before SLR14 injection, half of SLR14-treated mice was additionally given 2 mg anti-IFNAR antibodies. Brain tissues were collected for virological analysis 8 DPI. FIG. 28B: Measurement of genomic viral RNA in the brain 8 DPI by RT-qPCR using the CDCN2 primer-probe set. Means±s.e.m.; Statistical significance was calculated by one-way ANOVA followed by Tukey correction (FIG. 28B); $*P \leq 0.05$, $P \leq 0.01$, $*P \leq 0.001$, $****P \leq 0.0001$.

FIGS. 29A-29C illustrate the finding that SLR14 exerts strong antiviral effect in an AAV-based mouse model of SARS-CoV-2. FIG. 29A: Experimental scheme: B6J mice were intratracheally administered with $10^{11}$ genome copies of AAV9-hACE2 and let rest for 2 weeks before intranasal infection with $10^6$ PFU SARS-CoV-2 (2019n-CoV/USA_WA1/2020). 15 µg SLR14 or vehicle were intravenously administered 4 hours post infection. Lung tissues were collected for virological analysis 4 DPI. FIGS. 29B-29C: Measurement of genomic viral RNA in the lung parenchyma 2 DPI (FIG. 29B) and 4 DPI (FIG. 29C) by RT-qPCR using the CDCN2 primer-probe set. Means±s.e.m.; Statistical significance was calculated by Students' t-test (FIGS. 29B-29C); $*P \leq 0.05$, $P \leq 0.01$, $*P \leq 0.001$, $****P \leq 0.0001$. Data are representative of two independent experiments.

Figure 30A:
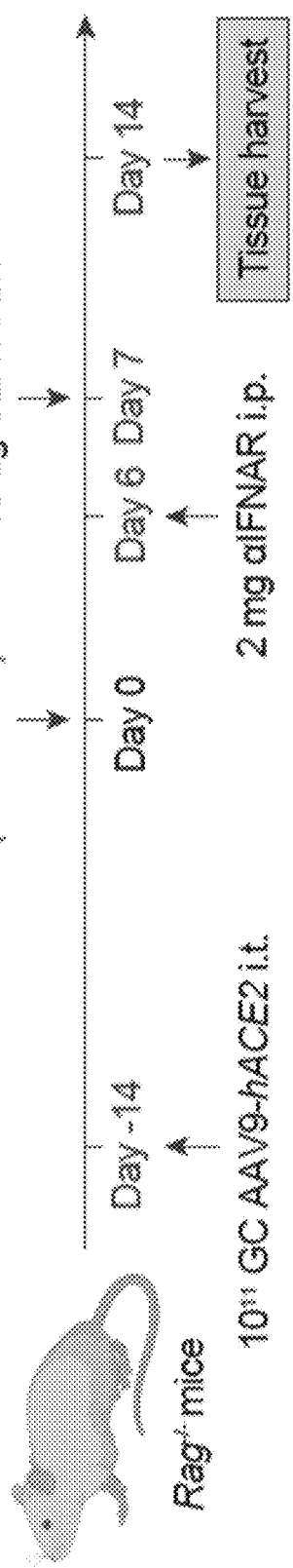
FIGS. 30A-30B illustrate the finding that SLR14 treatment in Rag$^{-/-}$ mice results in reduction of genomic viral RNA in the trachea.
Figure 30B:
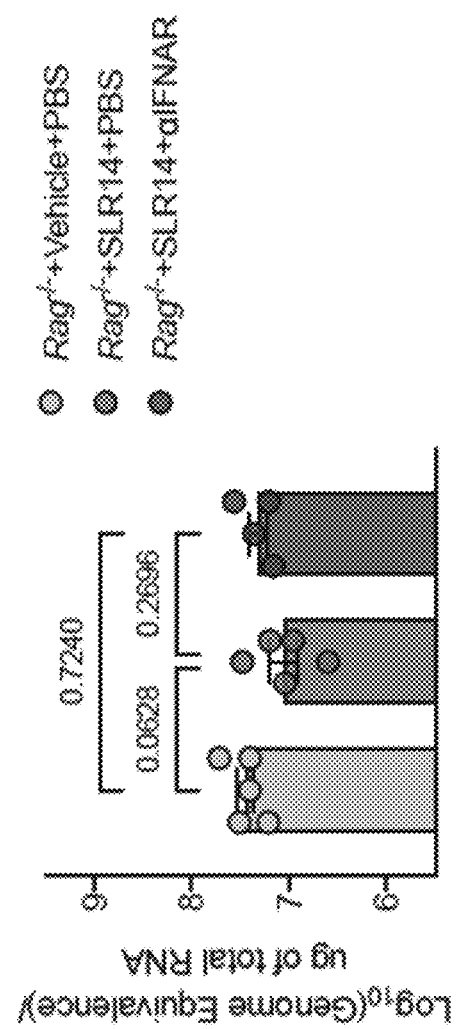

FIGS. 30A-30B illustrate the finding that SLR14 treatment in Rag$^{-/-}$ mice results in reduction of genomic viral RNA in the trachea. FIG. 30A: Experimental scheme: Rag$^{-/-}$ mice were intratracheally administered with $10^{11}$ genome copies of AAV9-hACE2 and let rest for 2 weeks before intranasal infection with $10^6$ PFU SARS-CoV-2 (2019n-CoV/USA_WA1/2020). 15 µg SLR14 or vehicle were intravenously administered 7 DPI. 24 hours before SLR14 injection, half of SLR14-treated mice was additionally given 2 mg anti-IFNAR antibodies. Trachea tissues were collected for virological analysis 14 DPI. FIG. 30B: Measurement of genomic viral RNA in the trachea 14 DPI by RT-qPCR. Mean s.e.m.; Statistical significance was calculated by one-way ANOVA followed by Tukey correction (FIG. 30B); *$P \leq 0.05$, $P \leq 0.01$, *$P \leq 0.001$, ****$P \leq 0.0001$. Data are pooled from two independent experiments.

FIGS. 31A-31C illustrate the finding that single-dose SLR14 reduces genomic viral RNA in Rag$^{-/-}$ mice chronically infected with VOCs. FIG. 31A: Experimental scheme: Rag$^{-/-}$ mice were intratracheally administered with $10^{11}$ genome copies of AAV9-hACE2 and let rest for 2 weeks before intranasal infection with B.1.1.7 or B.1.526. 15 µg SLR14 or vehicle were intravenously administered 7 DPI. Lung tissues were collected for virological analysis 14 DPI.

FIGS. 31B-31C: Measurement of genomic viral RNA in the lung from mice infected with B.1.1.7 (FIG. 31B) or B.1.526 (FIG. 31C) 14 DPI by RT-qPCR using the CDCN2 primer-probe set. Mean±s.e.m.; Statistical significance was calculated by Students' t-test (FIGS. 31B-31C); *$P \leq 0.05$, $P \leq 0.01$, *$P \leq 0.001$, ****$P \leq 0.0001$.

FIGS. 32A-32C illustrate the finding that mouse adapted SARS-CoV-2 demonstrates strong resistance to SLR14-mediated antiviral activity. FIG. 32A: Experimental scheme: Rag$^{-/-}$ mice were intratracheally administered with $10^{11}$ genome copies of AAV9-hACE2 and let rest for 2 weeks before intranasal infection with mouse-adapted SARS-CoV-2 MA10. 15 µg SLR14 or vehicle were intravenously administered 7 DPI. Lung tissues were collected for virological analysis 14 DPI. FIGS. 32B-32C: Measurement of genomic viral RNA and infectious virus titer in the lung from mice infected with MA10 14 DPI by RT-qPCR using the CDCN2 primer-probe set. Mean±s.e.m.; Statistical significance was calculated by Students' t-test (FIGS. 32B-32C); *$P \leq 0.05$, $P \leq 0.01$, *$P \leq 0.001$, ****$P \leq 0.0001$.

Example 14

The sudden arrival and devastating spread of COVID-19 have emphasized the importance of continuous efforts to develop broad-spectrum antiviral agents. Here, the in vivo efficacy of SLR14 was evaluated against viral replication throughout the respiratory tract and disease development in a mouse model of severe SARS-CoV-2 infection. SLR14 conferred considerable antiviral resistance in the lower respiratory tract and effectively prevented morbidity and mortality following infection with the ancestral virus. The effect of host factor, tissue compartment, and treatment timing in the protective capacity of SLR14 was examined, and the protective efficacy of SLR14 was found to depend on intact IFNAR signaling. Early SLR14 administration was shown to provide superior protection, while treatment as late as 48 hours post infection still afforded partial protection. The therapeutic potential for SLR14 wa further tested in chronically infected immunodeficient mice and a single dose of SLR14 was demonstrated to confer near-sterilizing immunity by the innate immune system alone, even in the absence of T and B cells. Finally, SLR14 was found to confer broad protection against all emerging SARS-CoV-2 variants.

The apparent protective role of early and regulated IFN-I suggests IFN-based therapies can be utilized for prevention and treatment of COVID-19. In a golden hamster model of SARS-CoV-2 infection, intranasal administration of commercially available universal IFN (IFNα A/D) reduced viral burden and attenuated pathology in the lung. Growing evidence also suggests that recombinant IFN-based intervention during the early stage of COVID-19 could provide desired clinical benefits in humans. In a retrospective multicenter cohort study of 446 COVID-19 patients, early administration of inhaled IFNα2b produced more favorable clinical responses compared to lopinavir/ritonavir (LPV/r) treatment alone and was associated with reduced in-hospital mortality. While results from recombinant IFN-based clinical trials are promising, one of the major disadvantages of this approach is its high cost, with the direct medical cost of IFN treatment regimen to range between $1,120 and $1,962 and PEG-IFN treatment regimen between $2,156 and $5,887. In addition, administration of recombinant IFN has been shown to induce neutralizing antibody response that could render the therapy ineffective. SLR14 addresses these challenges with, for example, drastically increased affordability due to its synthetic simplicity, small size, and manufacturability, and its ability to induce different members of the IFN-I family, including 10 IFN-α subtypes and an IFN-β, which maximizes the likelihood of downstream responses to be functional. In particular, the ability of SLR14 to elicit IFN-β is ideal as it enables early medical intervention for COVID-19 patients with pre-existing autoantibodies against one or multiple subtypes of IFN-α, who are particularly susceptible to prolonged viral replication and severe disease after infection with SARS-CoV-2.

The clinical efficacy of CP in patients with severe COVID-19 has not been thoroughly demonstrated, and its use in different stages of infection and disease remains experimental. Emergence of immune-evading variants from patients with immunosuppression of T cell and B cell arms indicate caution should be used for CP therapy. In these patients, the administered antibodies have little support from cytotoxic CD8 T cells or helper CD4 T cells, thereby reducing the chances of clearance and theoretically allowing for SARS-CoV-2 escape. Therefore, a novel therapeutic paradigm that treats persistent viral infection regardless of its effect on adaptive immunity will hold immense potential for this patient population. This study demonstrated that a single dose of SLR14 in mice lacking the adaptive immune system in the setting of chronic SARS-CoV-2 infection can induce near-sterilizing immunity. These results demonstrated that SLR14's utility extends beyond prophylactic antivirals, but also therapeutics that can be given to patients with immunocompromised conditions, providing an immediate solution to simultaneously cure chronic infection and suppress future emergence of immune-evasive variants. From an evolutionary perspective, such sterilizing protection induced exclusively through innate immune activation is analogous to antiviral mechanisms in metazoan organisms lacking adaptive immunity, which provides a basic, yet crucial, protective strategy against viral pathogens.

Vaccines remain the best approach to thwart the COVID-19 pandemic. However, with many countries lacking access to adequate vaccine doses, alternative strategies need to be developed and rapidly distributed to parts of the world severely impacted by these variants. Here, SLR14 was shown to potently prevented morbidity and mortality following infection with clinically relevant VOC, which have vastly different signature mutations and immune-evading capacity. The protective capacity of SLR14 was lower when administered against B.1.351 or B.1.1.7. Importantly, SLR14 still retained considerable residual antiviral capacity, which may be attributed by the speed, magnitude, and diversity of IFN-I responses induced by SLR14 that could collectively overcome viral resistance. Up until this point, B.1.1.7 has been recognized as a minimally immune-evasive variant based on both antibodies and T cell recognition. Here, this study provides the first set of in vivo evidence to indicate that B.1.1.7 exhibits signs of IFN-I evasion and responds only moderately to IFN-based therapy. Such innate immune evasion may underlie the rapid global spread of B.1.1.7. These results showcase SLR14's ability to not only be utilized as a therapeutic agent, but also an investigative tool for functional assessment of basic SARS-CoV-2 biology.

Several drugs have been approved by FDA under Emergency Use Authorization (EUA), including dexamethasone, remdesivir, monoclonal antibodies, tocilizumab, and baricitinib, to treat COVID-19. However, these therapeutics typically provide modest benefits at best and are limited to a subset of patients. While currently licensed vaccines demonstrate astounding protective efficacy against COVID-19, a new variant may develop in the future to significantly reduce efficacy. Further, there is a global shortage in vaccines with inequitable access in many lower income countries. The development, characterization, and ultimate deployment of an effective antiviral against SARS-CoV-2 can prevent substantial morbidity and mortality associated with COVID-19. In addition to its therapeutic potentials, SLR14 can be used as an invaluable investigative tool to advance the understanding of protective antiviral immunity against respiratory viruses, which will enable the rational design of next-generation antiviral therapeutics.

Figure 35A:
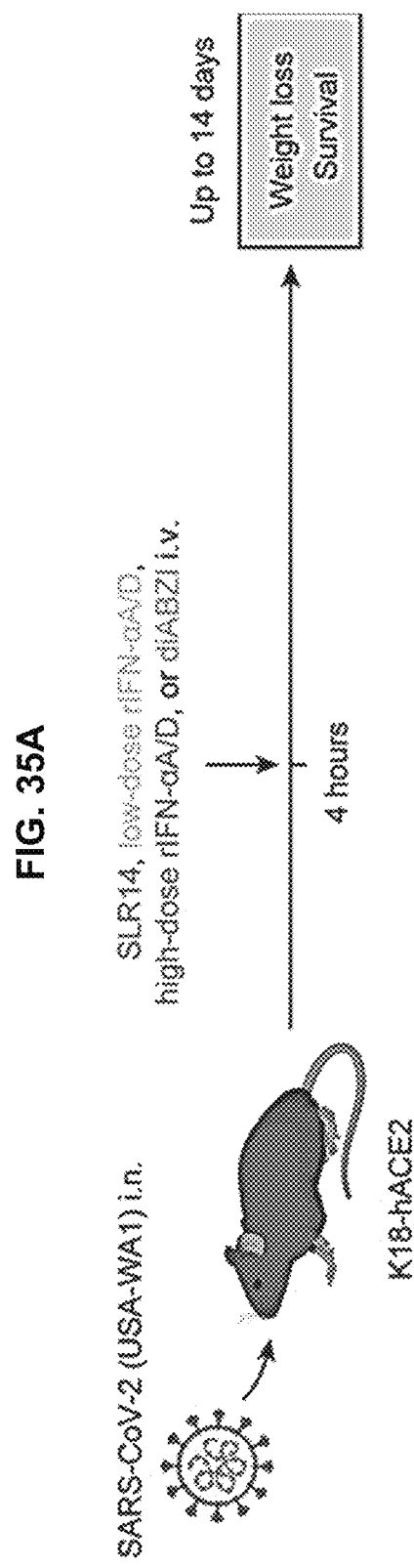
FIGS. 35A-35D illustrate the finding that SLR14 demonstrates superior protective capacity compared to other IFN-I-based antiviral strategies.
Figure 35D:
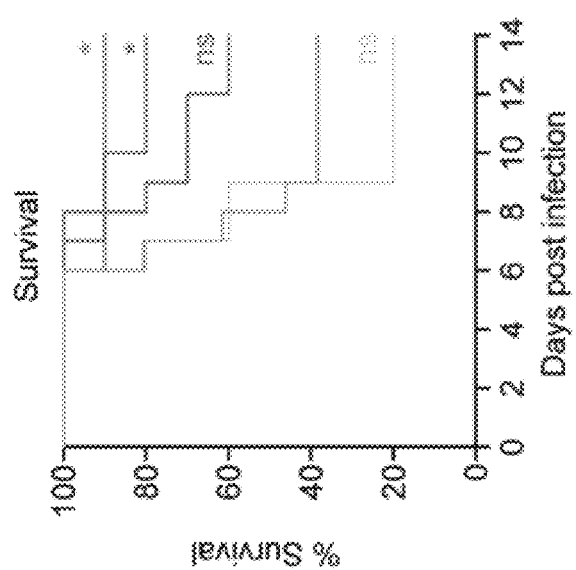
Figure 35C:
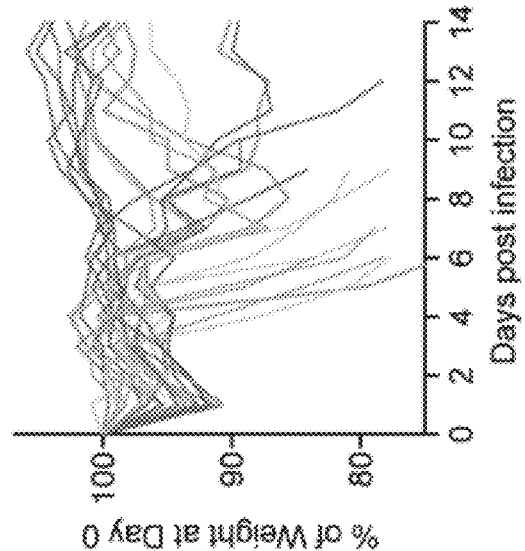
Figure 35B:
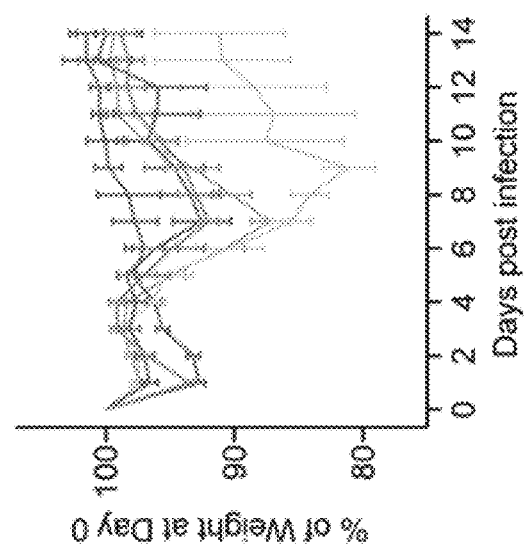

Example 15: SLR14 Demonstrates Superior Protective Capacity Compared to Other IFN-I-Based Antiviral Strategies To more thoroughly characterize the antiviral potency of SLR14 against SARS-CoV-2, the approach against recombinant IFN-I as well as IFN-I-inducing agents were benchmarked in vivo. A recombinant universal IFN-I (rIFN-αA/D) and a small-molecule agonist diABZI that activates STING (a critical component of the cytosolic DNA sensing pathway) were studied given their promising antiviral activities in preclinical studies (Hoagland et al., 2021; Humphries et al., 2021; Li et al., 2021b). Similar to SLR14 treatment, SARS-CoV-2-infected K18-hACE2 mice were treated intravenously with low doses rIFN-αA/D, high doses rIFN-αA/D, or diABZI 4 hours post infection and monitored their disease progression (FIG. 35A). Consistent with the initial observations, SLR14 largely prevented SARS-CoV-2 infection-induced weight loss and lethality (FIGS. 35B-D). rIFN-αA/D treatment resulted in variable but clear dose-dependent protective effects (FIGS. 35B-D). While high-dose rIFN-αA/D partially alleviated weight loss and lethality in treated K18-hACE2 mice, low-dose rIFN-αA/D failed to confer any protection. The protective capacity of systemic diABZI in preventing lethality was comparable to that of SLR14, although it did not prevent weight loss caused by the infection (FIGS. 35B-D). This was consistent with recent studies reporting diABZI as a highly protective antiviral agent against SARS-CoV-2 infection in mice, especially when given intranasally (Humphries et al., 2021; Li et al., 2021b). Together, these results demonstrate that SLR14 represents a superior antiviral strategy that protects against weight loss and death induced by SARS-CoV-2 infection in vivo.

FIGS. 35A-35D illustrate the finding that SLR14 demonstrates superior protective capacity compared to other IFN-I-based antiviral strategies. FIG. 35A: Experimental scheme: K18-hACE2 mice were intranasally infected with $5 \times 10^2$ PFU SARS-CoV-2 (2019n-CoV/USA_WA1/2020). 4 hours post infection, infected K18-hACE2 mice were intravenously treated with 15 μg SLR14, $2 \times 10^4$ U rIFN-αA/D (low-dose), $2 \times 10^5$ U rIFN-αA/D (high-dose), 20 μg diABZI, or vehicle. Weight loss and survival were monitored daily up to 14 DPI. Death was recorded when mice were found dead in the cage, moribund, or at 80% of original body weight. FIGS. 35B-35D: Weight loss and survival of K18-hACE2 mice from 1 to 14 DPI. Mean±s.e.m.; Statistical significance was calculated by log-rank Mantel-Cox test (FIG. 35D); *$P \le 0.05$, $P \le 0.01$, *$P \le 0.001$, ****$P \le 0.0001$. Data are pooled from two independent experiments.

TABLE 1

Amino acid changes identified in SARS-CoV-2 re-sequenced after virus isolation as compared to the reference genome (Accession MN908947). Listed are amino acid substitutions and deletions for each of the genes. Letters indicate amino acids, numbers indicate amino acid positions, asterisks indicate stop codon mutations, and dashes indicate deletions. Underlined mutations are lineage defining.

| GenBank accession | B.1.1.7 MZ202178 | B.1.351 MZ202314 | P.1 MZ202306 | B.1.526 MZ201303 |
|---|---|---|---|---|
| E |  | P71L |  |  |
| N | M1X | T205I | P80R | M1X |
|  | D3L |  | R203K | P199L |
|  | R203K |  | G204R | M234I |
|  | G204R |  |  |  |
|  | S235F |  |  |  |
| ORF1a | T1001I | T265I | S1188L | T265I |
|  | P1213L | K1655N | K1795Q | T2977I |
|  | A1708D | K3353R | G2941S | L3201P |
|  | I2230T | S3675- | S3675- | S3675- |
|  | M2259I | G3676- | G3676- | G3676- |
|  | S3675- | F3677- | F3677- | F3677- |
|  | G3676- |  |  |  |
|  | F3677- |  |  |  |
| ORF1b | P218L | P314L | P314L | P314L |
|  | P314L |  | A1219S | Q1011H |
|  | A1432V |  | E1264D | R1078C |
| ORF3a |  | Q57H | Q57H | P42L |
|  |  | W131L | S253P | Q57H |
|  |  | S171L |  |  |
| ORF7a |  | V93F |  |  |
| ORF8 | Q27* | R115L | E92K | T11I |
|  | R52I |  |  |  |
|  | K68* |  |  |  |
|  | Y73C |  |  |  |
| ORF9b |  |  | Q77E |  |
| S | H69- | L18F | L18F | L5F |
|  | V70- | D80A | T20N | T95I |
|  | Y144- | D215G | P26S | D253G |
|  | N501Y | L242H | D138Y | E484K |
|  | A570D | K417N | R190S | D614G |
|  | D614G | E484K | K417T | A701V |
|  | P681H | N501Y | E484K |  |
|  | T716I | D614G | N501Y |  |
|  | S982A | Q677H | D614G |  |
|  | D1118H | R682W | H655Y |  |
|  |  | A701V | T1027I |  |
|  |  | A243- | V1176F |  |
|  |  | L244- |  |  |
|  |  | H245- |  |  |

Abbreviations: E = envelope protein, N = nucleocapsid protein, ORF = open reading frame, S = spike protein.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A method for treating or ameliorating severe acute respiratory syndrome coronavirus 2 (SARS-CoV-2) infection in a subject, the method comprising administering to the subject a therapeutically effective amount of a RNA molecule comprising SLR-14-Tp
(5'-pppGGAUCGAUCGAUCGUUCGCGAUCGAUCGAUCC-3',
SEQ ID NO: 1), SLR-14-amino-Tp
(5'-pppGGAUCGAUCGAUCGUXCGCGAUCGAUCGAUCC-3', where
X = protected or deprotected 5'-Dimethoxytrityl-5-
[N-(trifluoroacetylaminohexyl)-3-acrylimido]-2'-
deoxy Uridine,3'-[(2-cyanoethyl)-
(N,N-diisopropyl)]-phosphoramidite (aminomodifier
C6dT), SEQ ID NO: 2), SLR-14-Dp
(5'-ppGGAUCGAUCGAUCGUUCGCGAUCGAUCGAUCC-3',
SEQ ID NO: 3),
or SLR-14-amino-Dp
(5'-ppGGAUCGAUCGAUCGUXCGCGAUCGAUCGAUCC-3', where
X = protected or deprotected aminomodifier C6dT,
SEQ ID NO: 4),.

wherein the SARS-CoV-2 comprises at least one variant strain selected from B.1.1.7 (Alpha), B.1.351 (Beta), P.1 (Gamma), B.1.617.2 (Delta), B.1.429/B.1.427 (Epsilon), B.1.617.1 (Kappa), B.1.525 (Eta), B.1.526 (Iota), P.3 (Theta), P.2 (Zeta), and B.1.1.529 (Omicron).

2. The method of claim 1, wherein the subject is a tumor-bearing subject.

3. The method of claim 1, wherein the subject is an immune-compromised or immunodeficient subject.

4. The method of claim 1, wherein the administering takes place before the subject is exposed to the virus.

5. The method of claim 1, wherein the administering takes place after the subject is exposed to the virus.

6. The method of claim 1, wherein the administering reduces, minimizes, or prevents viral replication in the subject.

7. The method of claim 1, wherein the administering reduces recovery time for, eliminates, or minimizes at least one complication from the viral infection.

8. The method of claim 7, wherein the at least one complication comprises at least one of weight loss, fever, cough, fatigue, muscle or body ache, nausea, vomiting, diarrhea, shortness of breath, loss of smell or taste, acute respiratory distress syndrome (ARDS), low blood oxygen levels, pneumonia, multi-organ failure, septic shock, heart failure, arrhythmias, heart inflammation, blood clots, and death.

9. The method of claim 1, wherein the SARS-CoV-2 comprises at least one variant strain selected from A.1-A.6, B.3-B.7, B.9, B.10, B.13-B.16, B.2, B.1 lineage, P.1, P.2, P.3, and R.1.

10. The method of claim 9, wherein the B.1 lineage comprises at least one of B.1, B.1.1, B.1.1.7, B.1.1.7 with E484K, B.1.2, B.1.5-B.1.72, B.1.9, B.1.13, B.1.22, B.1.26, B.1.37, B.1.3-B.1.66, B.1.177, B.1.243, B.1.313, B.1.351, B.1.427, B.1.429, B.1.525, B.1.526, B.1.526.1, B.1.526.2, B.1.617, B.1.617.1, B.1.617.2, B.1.617.3, B.1.619, B.1.620, and B.1.621.

11. The method of claim 1, wherein the subject suffers from long COVID.

12. The method of claim 1, wherein the RNA molecule comprises

```
SLR-14-Tp
(5'-pppGGAUCGAUCGAUCGUUCGCGAUCGAUCGAUCC-3',
SEQ ID NO: 1).
```

13. The method of claim 1, wherein the RNA molecule comprises SLR-14-amino-Tp (5'-pppG-GAUCGAUCGAUCGUXCGCGAUCGAUCGAUCC-3', where X=protected or deprotected aminomodifier C6dT, SEQ ID NO: 2).

14. The method of claim 1, wherein the RNA molecule comprises

```
SLR-14-Dp
(5'-ppGGAUCGAUCGAUCGUUCGCGAUCGAUCGAUCC-3',
SEQ ID NO: 3).
```

15. The method of claim 1, wherein the RNA molecule comprises SLR-14-amino-Dp (5'-ppG-GAUCGAUCGAUCGUXCGCGAUCGAUCGAUCC-3', where X=protected or deprotected aminomodifier C6dT, SEQ ID NO: 4).

* * * * *

SEQUENCE LISTING

```
<160> NUMBER OF SEQ ID NOS: 4

<210> SEQ ID NO 1
<211> LENGTH: 32
<212> TYPE: RNA
<213> ORGANISM: Artificial Sequence
<220> FEATURE:
<223> OTHER INFORMATION: Triphosphorylated at the 5' end.

<400> SEQUENCE: 1
ggaucgaucg aucguucgcg aucgaucgau cc                                32

<210> SEQ ID NO 2
<211> LENGTH: 32
<212> TYPE: RNA
<213> ORGANISM: Artificial Sequence
<220> FEATURE:
<223> OTHER INFORMATION: Triphosphorylated at the 5' end.
<220> FEATURE:
<221> NAME/KEY: modified_base
<222> LOCATION: (16)..(16)
<223> OTHER INFORMATION: u = aminomodifier C6dT

<400> SEQUENCE: 2
ggaucgaucg aucguucgcg aucgaucgau cc                                32

<210> SEQ ID NO 3
<211> LENGTH: 32
<212> TYPE: RNA
<213> ORGANISM: Artificial Sequence
<220> FEATURE:
<223> OTHER INFORMATION: Diphosphorylated at the 5' end.

<400> SEQUENCE: 3
ggaucgaucg aucguucgcg aucgaucgau cc                                32

<210> SEQ ID NO 4
<211> LENGTH: 32
<212> TYPE: RNA
<213> ORGANISM: Artificial Sequence
<220> FEATURE:
<223> OTHER INFORMATION: Diphosphorylated at the 5' end.
<220> FEATURE:
<221> NAME/KEY: modified_base
<222> LOCATION: (16)..(16)
<223> OTHER INFORMATION: u = aminomodifier C6dT

<400> SEQUENCE: 4
ggaucgaucg aucguucgcg aucgaucgau cc                                32
```